(12) United States Patent
Phillips et al.

(10) Patent No.: US 12,139,474 B2
(45) Date of Patent: *Nov. 12, 2024

(54) LPA RECEPTOR ANTAGONISTS AND USES THEREOF

(71) Applicant: Gilead Sciences, Inc., Foster City, CA (US)

(72) Inventors: Barton W. Phillips, San Mateo, CA (US); Doris T. Tang, Burlingame, CA (US); Chandrasekar Venkataramani, San Carlos, CA (US); Kin S. Yang, Foster City, CA (US); Anna Zagorska, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/322,890

(22) Filed: May 24, 2023

(65) Prior Publication Data

US 2024/0002367 A1 Jan. 4, 2024

Related U.S. Application Data

(63) Continuation of application No. 17/319,471, filed on May 13, 2021, now Pat. No. 11,702,407.

(60) Provisional application No. 63/034,190, filed on Jun. 3, 2020.

(51) Int. Cl.
| | | |
|---|---|---|
| C07D 403/10 | (2006.01) | |
| C07D 401/10 | (2006.01) | |
| C07D 401/14 | (2006.01) | |
| C07D 403/04 | (2006.01) | |
| C07D 413/04 | (2006.01) | |
| C07D 413/10 | (2006.01) | |
| C07D 413/14 | (2006.01) | |
| C07D 498/04 | (2006.01) | |

(52) U.S. Cl.
CPC ......... *C07D 403/10* (2013.01); *C07D 401/10* (2013.01); *C07D 401/14* (2013.01); *C07D 403/04* (2013.01); *C07D 413/04* (2013.01); *C07D 413/10* (2013.01); *C07D 413/14* (2013.01); *C07D 498/04* (2013.01)

(58) Field of Classification Search
CPC ................ C07D 403/10; C07D 401/10; C07D 401/14; C07D 403/04; C07D 413/04; C07D 413/10; C07D 413/14; C07D 498/04
See application file for complete search history.

(56) References Cited

U.S. PATENT DOCUMENTS

| | | |
|---|---|---|
| 10,662,172 B2 | 5/2020 | Shi et al. |
| 11,584,738 B2 | 2/2023 | Bestvater et al. |
| 11,702,407 B2 * | 7/2023 | Phillips ................ A61P 11/00 |
| | | 514/212.07 |
| 11,912,686 B2 | 2/2024 | Bestvater et al. |
| 2003/0092749 A1 | 5/2003 | Dombroski et al. |
| 2017/0360759 A1 | 12/2017 | Cheng et al. |

FOREIGN PATENT DOCUMENTS

| | | |
|---|---|---|
| JP | 2004526727 A | 9/2004 |
| WO | WO-2005012269 A1 | 2/2005 |
| WO | WO-2009135590 A1 | 11/2009 |
| WO | WO-2010068775 A2 | 6/2010 |
| WO | WO-2010077882 A2 | 7/2010 |
| WO | WO-2010077883 A2 | 7/2010 |
| WO | WO-2010141761 A2 | 12/2010 |
| WO | WO-2010141768 A2 | 12/2010 |
| WO | WO-2011017350 A2 | 2/2011 |
| WO | WO-2011037192 A1 | 3/2011 |
| WO | WO-2011041461 A2 | 4/2011 |
| WO | WO-2011041462 A2 | 4/2011 |
| WO | WO-2011041694 A2 | 4/2011 |
| WO | WO-2011041729 A2 | 4/2011 |
| WO | WO-2011053948 A1 | 5/2011 |
| WO | WO-2011159550 A2 | 12/2011 |
| WO | WO-2011159632 A1 | 12/2011 |
| WO | WO-2012039460 A1 | 3/2012 |
| WO | WO-2012078593 A2 | 6/2012 |
| WO | WO-2012078805 A1 | 6/2012 |
| WO | WO-2012100436 A1 | 8/2012 |
| WO | WO-2012138648 A1 | 10/2012 |
| WO | WO-2012138797 A1 | 10/2012 |
| WO | WO-2013/025733 A1 | 2/2013 |
| WO | WO-2013085824 A1 | 6/2013 |
| WO | WO-2013189862 A1 | 12/2013 |
| WO | WO-2013189864 A1 | 12/2013 |
| WO | WO-2013189865 A1 | 12/2013 |
| WO | WO-2014037303 A1 | 3/2014 |
| WO | WO-2014072486 A1 | 5/2014 |
| WO | WO-2014104372 A1 | 7/2014 |

(Continued)

OTHER PUBLICATIONS

International Search Report and Written Opinion dated Mar. 26, 2021 for Intl. Appl. No. PCT/US2020/060153.
International Search Report and Written Opinion dated Jul. 26, 2021 for Intl. Appl. No. PCT/US2021/032293.
International Search Report and Written Opinion dated Aug. 10, 2021 for Intl. Appl. No. PCT/US2021/032202.
Gallezot, J. et al. (2018) "Evaluation of the Lysophosphatidic Acid Receptor Type 1 Radioligand 11C-BMT-136088 for Lung Imaging in Rhesus Monkeys" The Journal of Nuclear Medicine, 59(2):327-333.
Cheng, P. et al. (2021) "Discovery of an Oxycyclohexyl Acid Lysophosphatidic Acid Receptor 1 (LPA1) Antagonist BMS-986278 for the Treatment of Pulmonary Fibrotic Diseases" J. Med. Chem., 64, 21, 15549-15581.

(Continued)

*Primary Examiner* — Laura L Stockton

(57) ABSTRACT

The present disclosure relates generally to compounds that bind to Lysophosphatidic Acid Receptor 1 (LPAR1) and act as antagonists of LPAR1. The disclosure further relates to the use of the compounds for the preparation of a medicament for the treatment of diseases and/or conditions through binding of LPAR1, including fibrosis and liver diseases such as non-alcoholic steatohepatitis (NASH).

4 Claims, No Drawings

(56) References Cited

FOREIGN PATENT DOCUMENTS

| | | |
|---|---|---|
| WO | WO-2014113485 A1 | 7/2014 |
| WO | WO-2014145873 A2 | 9/2014 |
| WO | WO-2015025164 A1 | 2/2015 |
| WO | WO-2015066456 A1 | 5/2015 |
| WO | WO-2015199234 A1 | 12/2015 |
| WO | WO-2017086430 A1 | 5/2017 |
| WO | WO-2017177004 A1 | 10/2017 |
| WO | WO-2017223016 A1 | 12/2017 |
| WO | WO-2019046239 A1 | 3/2019 |
| WO | WO-2019126084 A1 | 6/2019 |
| WO | WO-2019126085 A1 | 6/2019 |
| WO | WO-2019126086 A1 | 6/2019 |
| WO | WO-2019126087 A1 | 6/2019 |
| WO | WO-2019126089 A1 | 6/2019 |
| WO | WO-2019126090 A1 | 6/2019 |
| WO | WO-2019126093 A1 | 6/2019 |
| WO | WO-2019126094 A1 | 6/2019 |
| WO | WO-2019126098 A1 | 6/2019 |
| WO | WO-2019126099 A1 | 6/2019 |
| WO | WO-2019126103 A1 | 6/2019 |
| WO | WO-2020060914 A1 | 3/2020 |
| WO | WO-2020060915 A1 | 3/2020 |
| WO | WO-2020060916 A1 | 3/2020 |
| WO | WO-2020081410 A2 | 4/2020 |
| WO | WO-2020257135 A1 | 12/2020 |
| WO | WO-2020257138 A1 | 12/2020 |
| WO | WO-2020257139 A1 | 12/2020 |
| WO | WO-2021020429 A1 | 2/2021 |
| WO | WO-2021097039 A1 | 5/2021 |
| WO | WO-2021110805 A1 | 6/2021 |
| WO | WO-2021247217 A1 | 12/2021 |
| WO | WO-2022013378 A1 | 1/2022 |
| WO | WO-2022034568 A1 | 2/2022 |
| WO | WO-2022100623 A1 | 5/2022 |
| WO | WO-2022100624 A1 | 5/2022 |
| WO | WO-2022100625 A1 | 5/2022 |
| WO | WO-2022174882 A1 | 8/2022 |
| WO | WO-2022174883 A1 | 8/2022 |
| WO | WO-2022240879 A1 | 11/2022 |
| WO | WO-2022241023 A1 | 11/2022 |
| WO | WO-2023107938 A1 | 6/2023 |

OTHER PUBLICATIONS

Examination Report dated May 10, 2023 on Australian Application No. 2021282986.

Qian, et al. (2012) "Discovery of Highly Selective and Orally Active Lysophosphatidic Acid Receptor-1 Antagonists with Potent Activity on Human Lung Fibroblasts" J. Med. Chem., 55, 7920-7939.

* cited by examiner

LPA RECEPTOR ANTAGONISTS AND USES THEREOF

CROSS-REFERENCES TO RELATED APPLICATIONS

This Application is a Continuation of U.S. application Ser. No. 17/319,471 filed on May 13, 2021, which claims the benefit under 35 U.S.C. § 119 (e) of U.S. Provisional Application No. 63/034,190, filed on Jun. 3, 2020, which is hereby incorporated herein by reference in its entirety for all purposes.

FIELD

The present disclosure relates to compounds that bind to and act as antagonists of a lysophosphatidic acid (LPA) receptor, such as LPAR1. The disclosure further relates to the use of the compounds for the treatment and/or prophylaxis of diseases and/or conditions associated with one or more LPA receptors, e.g., an LPAR1 associated disease or condition.

BACKGROUND

Lysophosphatidic acids (mono-acyl-glycerol-3-phosphate, LPA) are a class of biologically active phospholipids that can be produced from lysophosphatidyl choline (LPC), e.g., by the enzyme autotaxin. A typical LPA has a glycerol, an ester-linked fatty acid at the sn-1 position, and a phosphate head group at the sn-3 position. LPA with various fatty acids have been identified, including palmitoyl LPA (16:0), stearoyl LPA (18:0), oleoyl LPA (18:1), linoleoyl LPA (18:2) and arachidonyl LPA (20:4). LPA exerts a wide range of cellular responses, such as proliferation, differentiation, survival, migration, adhesion, invasion, and morphogenesis through a family of rhodopsin-like G protein-coupled receptors (GPCRs). Six LPA receptors have been been characterized and were found to differ in their tissue distribution and downstream signaling pathways. These six LPA receptors are often referred to interchangeably as LPAR1-6 (gene) or LPA1-6 (protein). LPA receptor mediated signaling has been shown to influence many biological processes such as wound healing, immunity, carcinogenesis, angiogenesis and neurogenesis.

In vivo studies involving LPA receptor-deficient mice or certain tool compounds have suggested a potential of LPA receptors as possible drug targets in a variety of diseases including cancer, fibrosis, inflammation, pain, and cardiovascular diseases. More recently, LPAR1 antagonists have been studied clinically in connection with fibrotic disase states such as idiopathic pulmonary fibrosis (IPF) and systemic sclerosis.

A need remains for LPA antagonists with desirable selectivity, potency, metabolic stability, or reduced detrimental effects.

SUMMARY

The present disclosure provides compounds useful as inhibitors of Lysophosphatidic Acid Receptor 1 (LPAR1). The disclosure further relates to the use of the compounds for the treatment and/or prophylaxis of diseases and/or conditions through binding of LPAR1 by said compounds.

In one embodiment, provided herein is a compound of Formula (I),

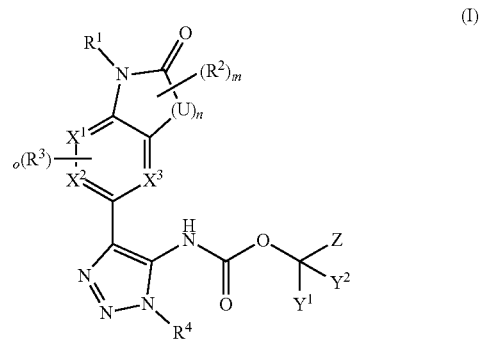

or a pharmaceutically acceptable salt thereof,
wherein:
$R^1$ is hydrogen or $C_{1-6}$ alkyl optionally substituted with 1 to 3 substituents, which can be the same or different, each independently selected from halogen, cyano, $C_{1-4}$ alkoxy, and $C_{3-10}$ cycloalkyl; or
$R^1$ is $C_{3-6}$ cycloalkyl optionally substituted with 1 to 3 substituents, which can be the same or different, each independently selected from halogen, cyano, $C_{1-4}$ alkoxy, and $C_{1-6}$ alkyl;
each $R^2$, which can be the same or different, is independently selected from hydrogen, halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $-N(R^{2A1})(R^{2A2})$, $-O-R^{2A1}$, $-S-R^{2A1}$, $-C(O)N(R^{2A1})(R^{2A2})$, $-NR^{2A1}C(O)R^{2A2}$, $-NR^{2A1}C(O)N(R^{2A2})(R^{2A3})$, $-S(O)_{0-2}R^{2A1}$, $-S(O)_2N(R^{2A1})(R^{2A2})$, and $-NR^{2A1}S(O)_2R^{2A2}$, wherein each $R^{2A1}$, $R^{2A2}$, and $R^{2A3}$ is independently hydrogen or $C_{1-6}$ alkyl, wherein each $R^2$ alkyl, cycloalkyl, heterocyclic, aryl, and heteroaryl is optionally substituted with 1 to 4 $R^{2B}$, which can be the same or different, wherein each $R^{2B}$ is independently $C_{1-4}$ alkyl, $C_{1-4}$ alkoxy, hydroxy, halogen, or cyano;
each $R^3$, which can be the same or different, is independently selected from deuterium, halogen, $C_{1-6}$ alkyl, $C_{3-10}$ cycloalkyl, or $C_{1-4}$ alkoxy, wherein each $C_{1-6}$ alkyl and $C_{3-10}$ cycloalkyl, is optionally substituted with 1 to 3 halogens;
$R^4$ is $C_{1-6}$ alkyl optionally substituted with 1 to 3 substituents, which can be the same or different, each independently selected from halogen, cyano, $C_{1-4}$ alkoxy, $-C(O)N(R^{4A1})$, and $-N(R^{4A1})(R^{4A2})$, wherein each $R^{4A1}$ and $R^{4A2}$ is independently H, $C_{1-6}$ alkyl, or $C_{3-10}$ cycloalkyl; or
$R^4$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents, which can be the same or different, each independently selected from halogen, cyano, $C_{1-4}$ alkyl and $C_{1-4}$ alkoxy;
m is 0, 1, 2, 3, or 4;
n is 0, 1, 2, or 3;
is 0, 1, 2, or 3;
each of $X^1$, $X^2$, and $X^3$ is independently selected from CH and N;

each U is independently —CH=, —CH$_2$—, —N=, —NH—, or —O—;

each $Y^1$ and $Y^2$ is independently hydrogen, deuterium, or C$_{1-6}$ alkyl optionally substituted with 1 to 3 substituents, which can be the same or different, each independently selected from deuterium, halogen, cyano, C$_{2-3}$ alkynyl, C$_{1-4}$ alkoxy, and —C(O)NH—(C$_{1-4}$H$_{3-9}$); and Z is C$_{1-8}$ alkyl, C$_{1-6}$ alkoxy, C$_{3-6}$ cycloalkyl, C$_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, each independently selected from halogen, cyano, C$_{1-4}$ alkyl, C$_{1-4}$ alkoxy, and C$_{3-6}$ cycloalkyl, wherein the C$_{1-4}$ alkyl is optionally substituted with 1 to 3 substituents, which can be the same or different, each selected from C$_{1-4}$ alkoxy and halogen; or $Y^1$ and Z together with the carbon to which they are attached form C$_{3-6}$ cycloalkyl, C$_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents, which can be the same or different, each independently selected from cyano, C$_{1-4}$ alkyl, C$_{1-4}$ alkoxy, C$_{6-10}$ aryl and halogen, wherein the C$_{1-4}$ alkyl is optionally substituted with 1 to 3 substituents, which can be the same or different, each independently selected from C$_{1-4}$ alkoxy and halogen, and wherein the C$_{6-10}$ aryl is optionally substituted with 1 to 3 substituents, which can be the same or different, each independently selected from C$_{1-4}$ alkyl, C$_{1-4}$ alkoxy, and halogen, and $Y^2$ is hydrogen or deuterium.

In some embodiments, provided herein are pharmaceutical compositions comprising a compound provided herein, or pharmaceutically acceptable salt thereof, and a pharmaceutically acceptable excipient or carrier. In some embodiments, the pharmaceutical compositions comprise a therapeutically effective amount of a compound provided herein, or pharmaceutically acceptable salt thereof, and a pharmaceutically acceptable excipient or carrier.

In some embodiments, the pharmaceutical compositions provided herein further comprise one or more (e.g., one, two, three, four, one or two, one to three, or one to four) additional therapeutic agents, or pharmaceutically acceptable salts thereof. In some embodiments, the pharmaceutical compositions further comprise a therapeutically effective amount of the one or more (e.g., one, two, three, four, one or two, one to three, or one to four) additional therapeutic agents, or pharmaceutically acceptable salts thereof.

In some embodiments, the present disclosure provides methods of inhibiting LPAR1 activity in a subject in need thereof, comprising administering to the subject a therapeutically effective amount of a compound provided herein (e.g., a compound of Formula (I), (Ia), (II), (IIa), (IIIa)-(IIIg), (VIa)-(Vj)), or pharmaceutically acceptable salt thereof, or a pharmaceutical composition provided herein.

In some embodiments, the present disclosure provides methods of treating a patient having an LPAR1 mediated condition, comprising administering to the patient a therapeutically effective amount of a compound provided herein (e.g., a compound of Formula (I), (Ia), (II), (IIa), (IIIa)-(IIIg), (VIa)-(Vj)), or pharmaceutically acceptable salt thereof, or a pharmaceutical composition provided herein.

DETAILED DESCRIPTION

The present disclosure relates to LPA receptor antagonists, such as antagonists of LPAR1. The disclosure also relates to compositions and methods relating to LPAR1 antagonists and the use of such compounds for treatment and/or prophylaxis of LPAR1-mediated diseases and conditions. The disclosure also relates to compositions and methods of treating and/or preventing liver disease including an LPAR1 antagonist in combination with one or more additional therapeutic agents.

It is commonly believed that patients with certain LPAR1-mediated diseases, such as cancer, fibrosis, inflammation, pain, and cardiovascular diseases, or liver diseases including non-alcoholic fatty liver disease (NAFLD) and non-alcoholic steatohepatitis (NASH) can benefit from the treatment with an LPAR1 antagonist and optionally one or more additional therapeutic agents.

Definitions and General Parameters

The description below is made with the understanding that the present disclosure is to be considered as an exemplification of the claimed subject matter and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present specification, the following terms and phrases are generally intended to have the meanings as set forth below, except to the extent that the context in which they are used indicates otherwise.

A dash ("—") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, $R^a$ in the below structure can be attached to any of the five carbon ring atoms or $R^a$ can replace the hydrogen attached to the nitrogen ring atom:

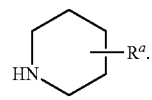

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (e.g., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula (I), (Ia), (II), (IIa), (IIIa)-(IIIg), (VIa)-(Vj). Also included are the specific Compounds 1 to 32 provided herehin (e.g., Examples 1-33).

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), or 1 to 3 carbon atoms (i.e., $C_{1-3}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amino" refers to the group —$NR^yR^z$ wherein $R^y$ and $R^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Fused" refers to a ring which is bound to an adjacent ring. In some embodiments the fused ring system is a heterocyclyl. In some embodiments the fused ring system is a oxabicyclohexanyl. In some embodiments the fused ring system is

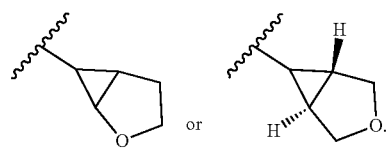 [SMILES: *C1C2CCOC12 ; "or" ; *C1[C@@H]2COC[C@@H]12]

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems. In some embodiments the bridged ring is a bicyclopentanyl (bicycle [1.1.1]pentanyl]) or bicyclooctanyl (bicycle[2.2.2]octanyl). In some embodiments, the bridge ring is

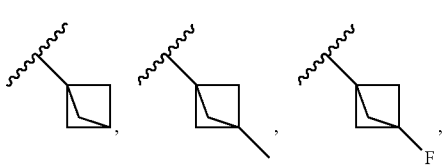

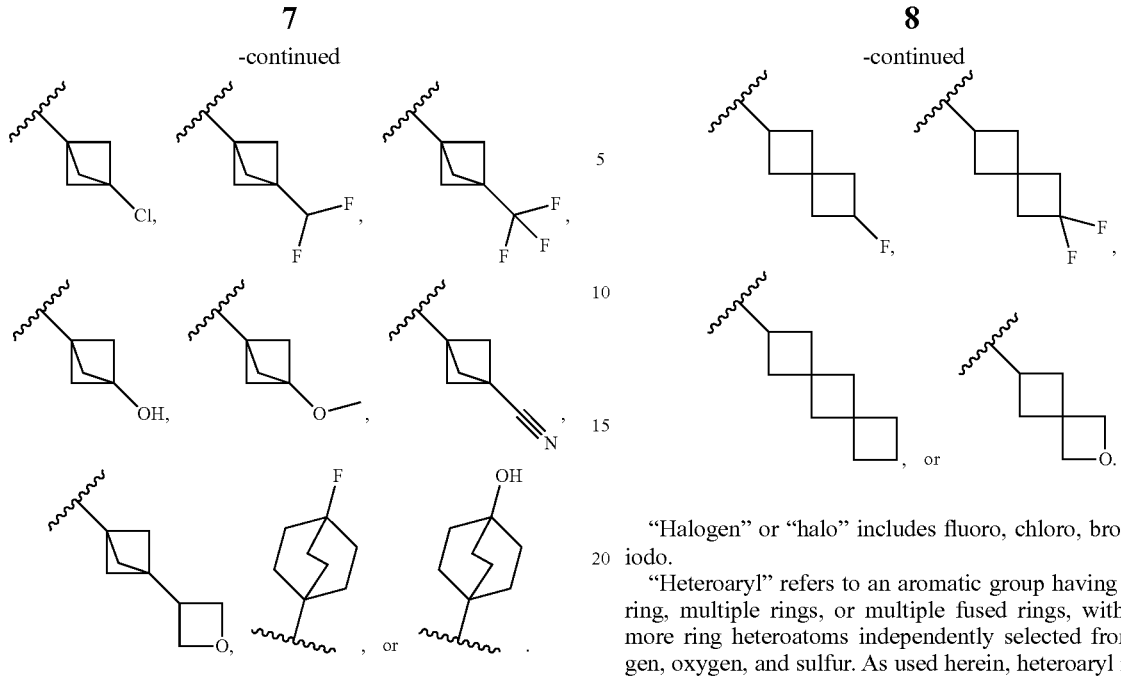

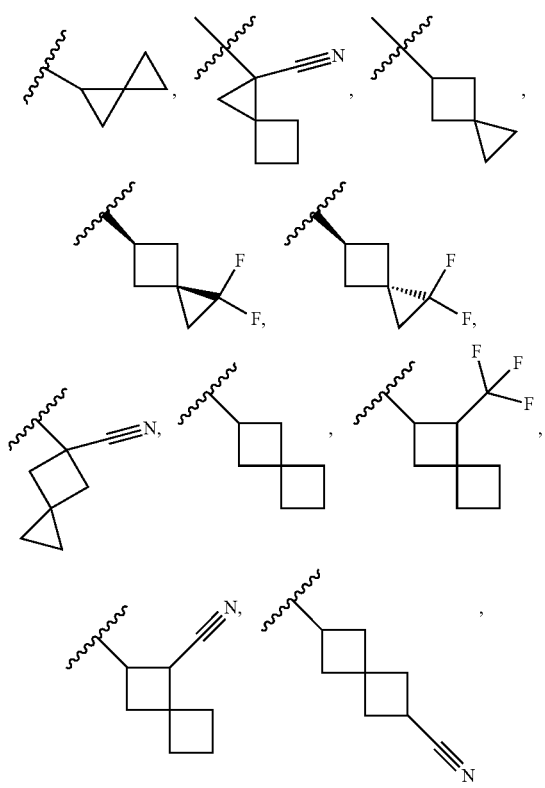

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. In some embodiments the spiro substituent is a spiropentanyl (spiro[a.b]pentanyl), spirohexanyl, spiroheptanyl, or spirodecanyl. In some embodiments the spiro substituent is "Halogen" or "halo" includes fluoro, chloro, bromo, and iodo.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the terms "heterocycle", "heterocyclyl", and "heterocyclic ring" are used interchangeably.

"Hydroxy" or "hydroxyl" refers to the group —OH.

"Oxo" refers to the group (=O) or (O).

"Sulfonyl" refers to the group —S(O)$_2$R$^c$, where R$^c$ is alkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH$_2$ group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, amino, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, amino, alkoxy, halo, oxo, and hydroxyl; "substituted heterocyclyl" refers to a heterocyclyl group having one or more substituents including alkyl, amino, haloalkyl, heterocyclyl, cycloalkyl, aryl, heteroaryl, alkoxy, halo, oxo, and hydroxyl; "substituted aryl" refers to an aryl group having one or more substituents including halo, alkyl, amino, haloalkyl, cycloalkyl, heterocyclyl, heteroaryl, alkoxy, and cyano; "substituted heteroaryl" refers to an heteroaryl group having one or more substituents including halo, amino, alkyl, haloalkyl, cycloalkyl, aryl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

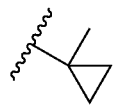

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. The compounds of the present disclosure can be in the form of a pharmaceutically acceptable salt. The term "pharmaceutically acceptable salts" refers to salts prepared from pharmaceutically acceptable non-toxic bases or acids, including inorganic bases or acids and organic bases or acids. In case the compounds of the present disclosure contain one or more acidic or basic groups, the disclosure also comprises their corresponding pharmaceutically or toxicologically acceptable salts, in particular their pharmaceutically utilizable salts. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine, amino acids, or other bases known to persons skilled in the art. The compounds of the present disclosure which contain one or more basic groups, i.e. groups which can be protonated, can be present and can be used according to the disclosure in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to persons skilled in the art.

If the compounds of the present disclosure simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts.

The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts. Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. Journal of Pharmaceutical Science, January 1977 vol. 66, No. 1, and other sources.

Furthermore, compounds disclosed herein may be subject to tautomerism. Where tautomerism, e.g., keto-enol tautomerism, of compounds or their prodrugs may occur, the individual forms, like, e.g., the keto and enol form, are each within the scope of the disclosure as well as their mixtures in any ratio. The same applies for stereoisomers, like, e.g., enantiomers, cis/trans isomers, diastereomers, conformers, and the like.

The term "protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. The term "deprotecting" refers to removing the protecting group.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

Further the compounds of the present disclosure may be present in the form of solvates, such as those which include as solvate water, or pharmaceutically acceptable solvates, such as alcohols, in particular ethanol. A "solvate" is formed by the interaction of a solvent and a compound.

In certain embodiments, provided are optical isomers, racemates, or other mixtures thereof of the compounds described herein or a pharmaceutically acceptable salt or a mixture thereof. If desired, isomers can be separated by methods well known in the art, e.g. by liquid chromatography. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high-pressure liquid chromatography (HPLC) column.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another. "Diastereomers" are stereoisomers that have at least two asymmetric atoms, but which are not mirror-images of each other.

Compounds disclosed herein and their pharmaceutically acceptable salts may, in some embodiments, include an asymmetric center and may thus give rise to enantiomers, diastereomers, and other stereoisomeric forms that may be defined, in terms of absolute stereochemistry, as (R)- or (S)- or, as (D)- or (L)- for amino acids. Some embodiments include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphoros, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

The disclosure also includes "deuterated analogs" of compounds disclosed herein, in which from 1 to n hydrogens attached to a carbon atom is/are replaced by deuterium, in which n is the number of hydrogens in the molecule. Such compounds may exhibit increased resistance to metabolism and thus be useful for increasing the half-life of any compound of Formula (I) when administered to a mammal, e.g., a human. See, e.g., Foster, "Deuterium Isotope Effects in Studies of Drug Metabolism," Trends Pharmacol. Sci. 5(12): 524-527 (1984). Such compounds are synthesized by means well known in the art, for example by employing starting materials in which one or more hydrogens have been replaced by deuterium.

Deuterium labelled or substituted therapeutic compounds of the disclosure may have beneficial DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Furthermore, the present disclosure provides pharmaceutical compositions comprising a compound of the present disclosure, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure can encompass any composition made by admixing at least one compound of the present disclosure and a pharmaceutically acceptable carrier.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G. S. Banker & C. T. Rhodes, Eds.).

"IC$_{50}$" or "EC$_{50}$" refers to the inhibitory concentration required to achieve 50% of the maximum desired effect. In many cases here the maximum desired effect is the inhibition of LPA induced LPAR1 activation. This term is obtained using an in vitro assay, such as a calcium mobilization assay, evaluating the concentration-dependent inhibition of LPA induced LPAR1 activity.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, the term "treatment" or "treating" means administering a compound or pharmaceutically acceptable salt of Formula (I), (Ia), (II), (IIa), (IIIa)-(IIIg), (VIa)-(Vj) for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving thedisease, that is, causing the regression of clinical symptoms or the severity thereof.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to LPAR1 antagonists. The therapeutically effective amount may vary depending on the subject, and disease or condition being treated, the weight and age of the subject, the severity of the disease or condition, and the manner of administering, which can readily be determined by one or ordinary skill in the art.

LIST OF ABBREVIATIONS AND ACRONYMS

| Abbreviation | Meaning |
| --- | --- |
| ACN or MeCN | Acetonitrile |
| aq. | Aqueous |
| Bn | Benzyl |

-continued

| Abbreviation | Meaning |
|---|---|
| COPD | Chronic Obstructive Pulmonary Disease |
| DCM | Dichloromethane |
| DIEA | N,N-Diisopropylethylamine |
| DMF | N,N-Dimethylformamide |
| DMSO | Dimethylsulfoxide |
| DPPA | Diphenylphosphoryl azide |
| EA | Ethyl acetate |
| EDTA | Ethylenediaminetetraacetic acid |
| ESI | Electronspray Ionization |
| Et | Ethyl |
| Et$_2$O | Diethyl ether |
| EtOAc | Ethyl acetate |
| h or hr(s) | Hour(s) |
| HBSS | Hanks' Balanced Salt solution |
| HCC | Hepatocellular carcinoma |
| HPLC | High performance liquid chromatography |
| LCMS or LC/MS | Liquid Chromatography Mass Spectrometry |
| LPA | Lysophosphatidic acid |
| LPC | Lysophosphatidylcholine |
| Me | Methyl |
| MeOH | Methanol |
| MS | Mass Spectrometry |
| m/z | Mass-to-charge ratio |
| NADPH | Dihydronicotinamide-adenine dinucleotide phosphate |
| NAFLD | Non-alcoholic fattyl liver disease |
| NASH | Non-alcoholic steatohepatitis |
| NMR | Nuclear Magnetic Resonance spectroscopy |
| PBC | Primary Biliary Cirrhosis |
| PE | Petroleum ether |
| PSC | Primary Sclerosing Choleangitis |
| rpm | Revolutions per minute |
| RT or rt | Room temperature |
| sat. | Saturated |
| TEMPO | 2,2,6,6-Tetramethylpiperidine 1-oxyl |
| TFA | Trifluoroacetic acid |
| THF | Tetrahydrofuran |
| T3P | Propanephosphonic acid anhydride |

As used herein, an "LPAR1 antagonist" refers to any agent that is capable of binding and inhibiting LPAR1. LPAR1, also known as LPA$_1$, is a GPCR that binds the lipid signaling molecule lysophosphatidic acid (LPA). Exemplary reference sequences for LPAR1 include the NCBI Reference Sequences NP_001392 (human protein), NP_001277415 (mouse protein), NM_001401 (human mRNA), and NM_001290486 (mouse mRNA). LPAR1 antagonists can act as competitive inhibitors of full or partial LPAR1 agonists, or as inverse agonists. The activity of an LPAR antagonist may be measured by methods known in the art, such as those described and cited in Castelino et al., 2010 Arthritis Rheum. 2011 May; 63(5): 1405-1415 or Swaney et al., J Pharmacol Exp Ther. 2011 March; 336(3):693-700.

As used herein, an "ACC inhibitor" refers to any agent that is capable of binding and inhibiting Acetyl-CoA carboxylase (ACC). ACC inhibitors can act as inhibitors or partial inhibitors of ACC. The agent can be a chemical compound or biological molecule (e.g., a protein or antibody). The activity of an ACC inhibitor can be measured by methods known in the art, such as those described and cited in U.S. Pat. No. 8,969,557 and/or in U.S. Pat. No. 10,208,063, both of which are incorporated herein by reference in their entirety.

As referred to herein, an "ASK1 inhibitor" can be any agent that is capable of inactivating an apoptosis signal regulating kinase 1 (ASK1) protein. The agent can be a chemical compound or biological molecule (e.g., a protein or antibody). The ASK1 protein activity can be measured by several different methods. For example, the activity of an ASK1 protein can be determined based on the ability of the ASK1 protein to phosphorylate a substrate protein. Methods for identifying an ASK1 inhibitor are known (see, e.g., U.S. 2007/0276050). Exemplary ASK1 substrate proteins include MAPKK3, MAPKK4, MAPKK6, MAPKK7, or fragments thereof. The ASK1 protein activity can also be measured by the phosphorylation level of the ASK1 protein, for example, the phosphorylation level of a threonine residue in the ASK1 protein corresponding to threonine 838 (T838) of a human full-length ASK1 protein or threonine 845 (T845) of a mouse full-length ASK1 protein. For example, where the ASK1 protein comprises a full-length human ASK1 protein sequence, an ASK1 inhibitor may attenuate phosphorylation of T838 in the full-length human ASK1 protein sequence. A site-specific antibody against human ASK1 T838 or mouse ASK1 T845 may be used to detect the phosphohorylation level.

As used herein, a "FXR agonist" refers to any agent that is capable of binding and activating farnesoid X receptor (FXR) which can be referred to as bile acid receptor (BAR) or NR1H4 (nuclear receptor subfamily 1, group H, member 4) receptor. FXR agonists can act as agonists or partial agonists of FXR. The agent can be a chemical compound or biological molecule (e.g., a protein or antibody). The activity of an FXR agonist can be measured by several different methods, e.g., in an in vitro assay using the fluorescence resonance energy transfer (FRET) cell free assay as described in Pellicciari, et al. Journal of Medicinal Chemistry, 2002 vol. 15, No. 45:3569-72.

Compounds

In one embodiment, provided herein is a compound of Formula (I),

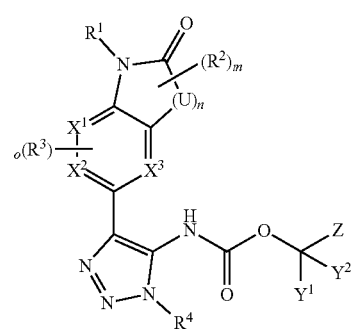

or a pharmaceutically acceptable salt thereof, wherein:

R$^1$ is hydrogen or C$_{1-6}$ alkyl optionally substituted with 1 to 3 substituents, which can be the same or different, each independently selected from halogen, cyano, C$_{1-4}$ alkoxy, and C$_{3-10}$ cycloalkyl; or R$^1$ is C$_{3-6}$ cycloalkyl optionally substituted with 1 to 3 substituents, which can be the same or different, each independently selected from halogen, cyano, C$_{1-4}$ alkoxy, and C$_{1-6}$ alkyl;

each R$^2$, which can be the same or different, is independently selected from hydrogen, halogen, cyano, oxo, C$_{1-4}$ alkyl, C$_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, —N(R$^{241}$)(R$^{242}$), —O—R$^{241}$, —S—R$^{241}$, —C(O)N(R$^{241}$)(R$^{242}$), —NR$^{241}$C(O)

$R^{242}$, —$NR^{241}C(O)N(R^{242})(R^{243})$, —$S(O)_{0-2}R^{241}$, —$S(O)_2N(R^{241})(R^{242})$, and —$NR^{241}S(O)_2R^{242}$, wherein each $R^{241}$, $R^{242}$, and $R^{243}$ is independently hydrogen or $C_{1-6}$ alkyl, wherein each $R^2$ alkyl, cycloalkyl, heterocyclic, aryl, and heteroaryl is optionally substituted with 1 to 4 $R^{2B}$, which can be the same or different, wherein each $R^{2B}$ is independently $C_{1-4}$ alkyl, $C_{1-4}$ alkoxy, hydroxy, halogen, or cyano;

each $R^3$, which can be the same or different, is independently selected from deuterium, halogen, $C_{1-6}$ alkyl, $C_{3-10}$ cycloalkyl, or $C_{1-4}$ alkoxy, wherein each $C_{1-6}$ alkyl and $C_{3-10}$ cycloalkyl, is optionally substituted with 1 to 3 halogens;

$R^4$ is $C_{1-6}$ alkyl optionally substituted with 1 to 3 substituents, which can be the same or different, each independently selected from halogen, cyano, $C_{1-4}$ alkoxy, —$C(O)N(R^{441})$, and —$N(R^{441})(R^{442})$, wherein each $R^{441}$ and $R^{442}$ is independently H, $C_{1-6}$ alkyl, or $C_{3-10}$ cycloalkyl; or $R^4$ is $C_{3-6}$ cycloalkyl or 3 to 6 membered heterocyclyl having 1 or 2 heteroatoms independently selected from nitrogen, oxygen, and sulfur, wherein the cycloalkyl or heterocyclyl are optionally substituted with 1 to 3 substituents, which can be the same or different, each independently selected from halogen, cyano, $C_{1-4}$ alkyl and $C_{1-4}$ alkoxy;

m is 0, 1, 2, 3, or 4;
n is 0, 1, 2, or 3;
is 0, 1, 2, or 3;
each of $X^1$, $X^2$, and $X^3$ is independently selected from CH and N;
each U is independently —CH=, —CH$_2$—, —N=, —NH—, or —O—;
each $Y^1$ and $Y^2$ is independently hydrogen, deuterium, or $C_{1-6}$ alkyl optionally substituted with 1 to 3 substituents, which can be the same or different, each independently selected from deuterium, halogen, cyano, $C_{2-3}$ alkynyl, $C_{1-4}$ alkoxy, and —$C(O)NH$—$(C_{1-4}H_{3-9})$; and
Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, each independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, each selected from $C_{1-4}$ alkoxy and halogen;
or
$Y^1$ and Z together with the carbon to which they are attached form $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the cycloalkyl, aryl, heterocyclyl, or heteroaryl are each optionally substituted with 1 to 3 substituents, which can be the same or different, each independently selected from cyano, $C_{1-4}$ alkyl, $C_{1-4}$ alkoxy, $C_{6-10}$ aryl and halogen, wherein the $C_{1-4}$ alkyl is optionally substituted with 1 to 3 substituents, which can be the same or different, each independently selected from $C_{1-4}$ alkoxy and halogen, and wherein the $C_{6-10}$ aryl is optionally substituted with 1 to 3 substituents, which can be the same or different, each independently selected from $C_{1-4}$ alkyl, $C_{1-4}$ alkoxy, and halogen, and $Y^2$ is hydrogen or deuterium.

In some embodiments, the compound of Formula (I), or pharmaceutically acceptable salt thereof, is a compound of Formula (Ia)

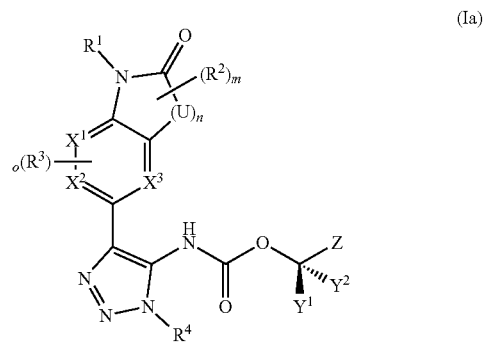

(Ia)

or pharmaceutically acceptable salt thereof.

In some embodiments of the compound of Formula (I) or (Ia), $R^1$ is hydrogen.

In some embodiments of the compound of Formula (I) or (Ia), $R^4$ is $C_{1-3}$ alkyl optionally substituted with 1 to 3 substituents, which can be the same or different, independently selected from —CN and —F. In some embodiments of the compound of Formula (I) or (Ia), $R^4$ is —$CH_3$.

In some embodiments, the compound of Formula (I), or pharmaceutically acceptable salt thereof, is a compound of Formula (II):

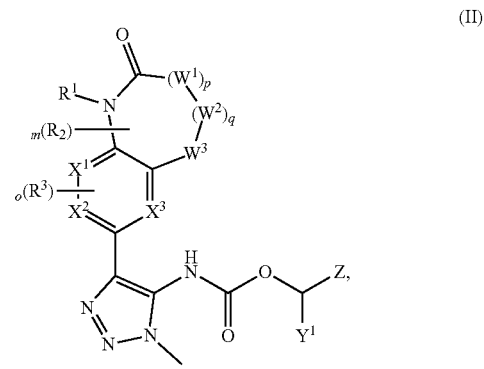

(II)

or pharmaceutically acceptable salt thereof;
wherein:
  $R^1$ is hydrogen;
  each $R^2$ is independently selected from deuterium, cyano, hydroxy, halogen, $C_{1-6}$ alkyl, $C_{3-10}$ cycloalkyl, or $C_{1-4}$ alkoxy, wherein the $C_{1-6}$ alkyl or $C_{3-10}$ cycloalkyl, is optionally substituted with 1 to 3 halogens;
  $W^1$ is —$CH_2$—;
  $W^2$ is —CH=, —$CH_2$—, or —O—;
  $W^3$ is —CH=, —$CH_2$—, —O—, or —NH—; and
  p and q are each independently 0 or 1.

In some embodiments, the compound of Formula (I), (Ia), or (II), or pharmaceutically acceptable salt thereof, is a compound of Formula (IIa):

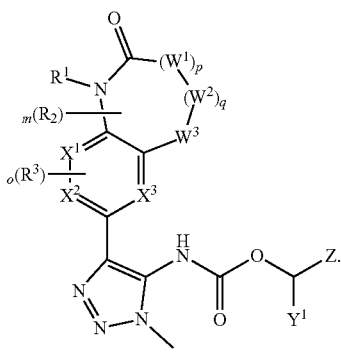

(IIa)

In some embodiments of the compound of Formula (I), (Ia), (II), or (IIa), p is 0 and q is 0. In some embodiments of the compound of Formula (I), (Ia), (II), or (IIa), p is 0 and q is 1. In some embodiments of the compound of Formula (I), (Ia), (II), or (IIa), p is 1 and q is 1.

In some embodiments, the compound of Formula (I), (Ia), (II), or (IIa), or pharmaceutically acceptable salt thereof, is a compound of Formula (IIIa):

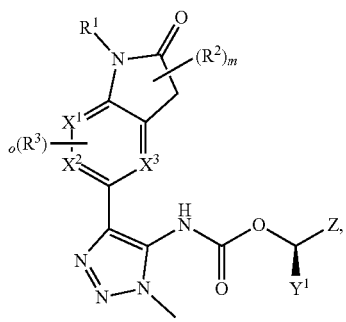

(IIIa)

or pharmaceutically acceptable salt thereof;
wherein:
  m is 0, 1, or 2; and
  is 0, 1, 2, or 3.

In some embodiments, the compound of Formula (I), (Ia), (II), or (IIa), or pharmaceutically acceptable salt thereof, is a compound of Formula (IIIb):

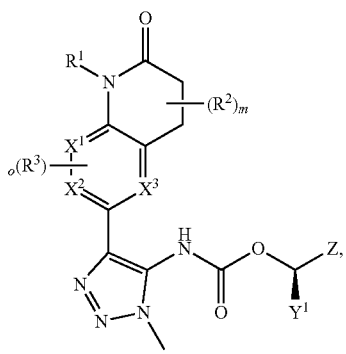

(IIIb)

or pharmaceutically acceptable salt thereof;
wherein:
  m is 0, 1, 2, 3, or 4; and
  is 0, 1, 2, or 3.

In some embodiments, the compound of Formula (I), (Ia), (II), or (IIa), or pharmaceutically acceptable salt thereof, is a compound of Formula (IIIc):

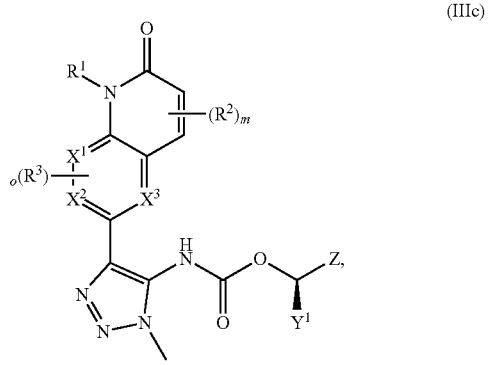

(IIIc)

or pharmaceutically acceptable salt thereof;
wherein:
  m is 0, 1 or 2; and
  is 0, 1, 2, or 3.

In some embodiments, the compound of Formula (I), (Ia), (II), or (IIa), or pharmaceutically acceptable salt thereof, is a compound of Formula (IIId):

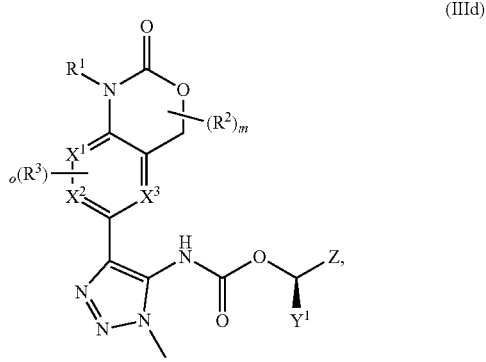

(IIId)

or pharmaceutically acceptable salt thereof;
wherein:
  m is 0, 1, or 2; and
  is 0, 1, 2, or 3.

In some embodiments, the compound of Formula (I), (Ia), (II), or (IIa), or pharmaceutically acceptable salt thereof, is a compound of Formula (IIIe):

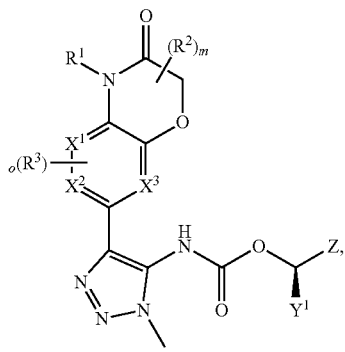

(IIIe)

or pharmaceutically acceptable salt thereof;
wherein:
 m is 0, 1, or 2; and
 is 0, 1, 2, or 3.

In some embodiments, the compound of Formula (I), (Ia), (II), or (IIa), or pharmaceutically acceptable salt thereof, is a compound of Formula (IIIf):

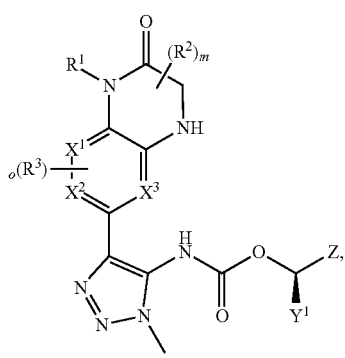

(IIIf)

or pharmaceutically acceptable salt thereof;
wherein:
 m is 0, 1, 2, or 3; and
 is 0, 1, 2, or 3.

In some embodiments, the compound of Formula (I), (Ia), (II), or (IIa), or pharmaceutically acceptable salt thereof, is a compound of Formula (IIIg):

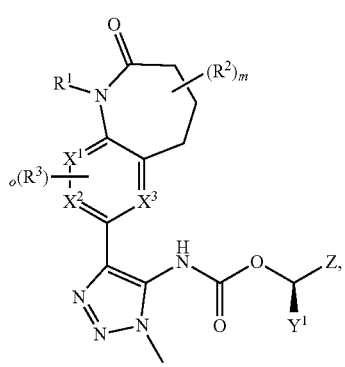

(IIIg)

or pharmaceutically acceptable salt thereof;
wherein:
 m is 0, 1, 2, 3, or 4; and
 is 0, 1, 2, or 3.

In some embodiments, the compound of Formula (I), (Ia), (II), or (IIa), or pharmaceutically acceptable salt thereof, is a compound of Formula (IVa):

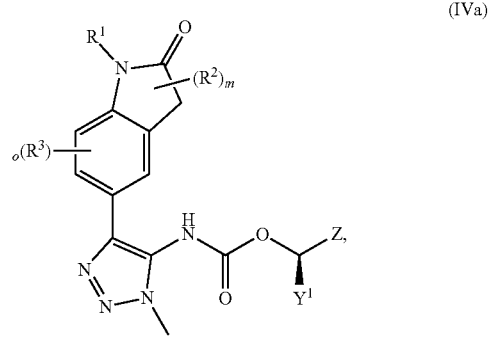

(IVa)

or pharmaceutically acceptable salt thereof;
wherein
 m is 0, 1, or 2; and
 is 0, 1, 2, or 3.

In some embodiments, the compound of Formula (I), (Ia), (II), or (IIa), or pharmaceutically acceptable salt thereof, is a compound of Formula (IVb):

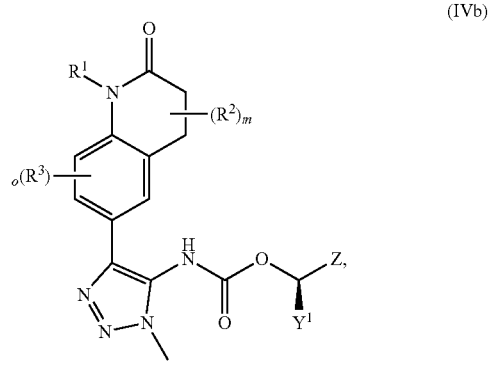

(IVb)

or pharmaceutically acceptable salt thereof;
wherein
 m is 0, 1, 2, 3, or 4; and
 is 0, 1, 2, or 3.

In some embodiments, the compound of Formula (I), (Ia), (II), or (IIa), or pharmaceutically acceptable salt thereof, is a compound of Formula (IVc):

(IVc)

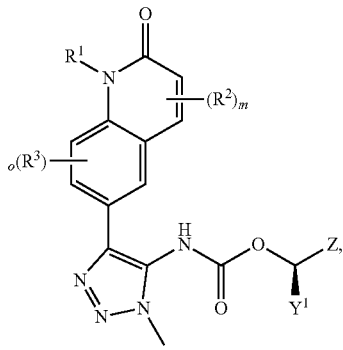

or pharmaceutically acceptable salt thereof;
wherein
  m is 0, 1, or 2; and
  is 0, 1, 2, or 3.

In some embodiments, the compound of Formula (I), (Ia), (II), or (IIa), or pharmaceutically acceptable salt thereof, is a compound of Formula (IVd):

(IVd)

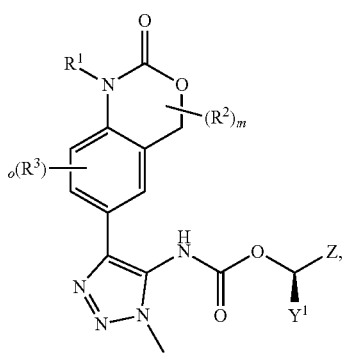

or pharmaceutically acceptable salt thereof;
wherein
  m is 0, 1, or 2; and
  is 0, 1, 2, or 3.

In some embodiments, the compound of Formula (I), (Ia), (II), or (IIa), or pharmaceutically acceptable salt thereof, is a compound of Formula (IVe):

(IVe)

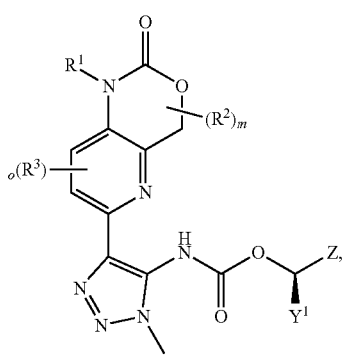

or pharmaceutically acceptable salt thereof;
wherein
  m is 0, 1, or 2; and
  o is 0, 1, or 2.

In some embodiments, the compound of Formula (I), (Ia), (II), or (IIa), or pharmaceutically acceptable salt thereof, is a compound of Formula (IVf):

(IVf)

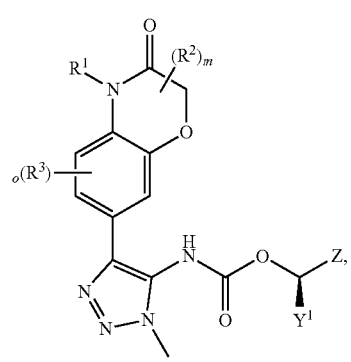

or pharmaceutically acceptable salt thereof;
wherein
  m is 0, 1, or 2; and
  is 0, 1, 2, or 3.

In some embodiments, the compound of Formula (I), (Ia), (II), or (IIa), or pharmaceutically acceptable salt thereof, is a compound of Formula (IVg):

(IVg)

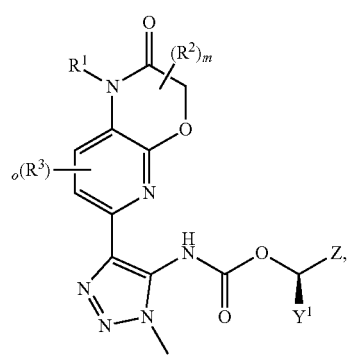

or pharmaceutically acceptable salt thereof;
wherein
  m is 0, 1, or 2; and
  o is 0, 1, or 2.

In some embodiments, the compound of Formula (I), (Ia), (II), or (IIa), or pharmaceutically acceptable salt thereof, is a compound of Formula (IVh):

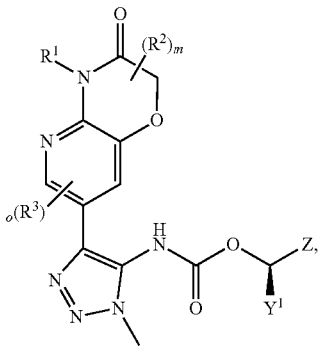

(IVh)

or pharamaceutically acceptable salt thereof;
wherein
m is 0, 1, or 2; and
o is 0, 1, or 2.

In some embodiments, the compound of Formula (I), (Ia), (II), or (IIa), or pharmaceutically acceptable salt thereof, is a compound of Formula (IVi):

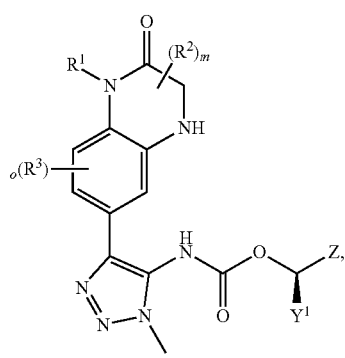

(IVi)

or pharmaceutically acceptable salt thereof;
wherein
m is 0, 1, or 2;
is 0, 1, 2, or 3.

In some embodiments, the compound of Formula (I), (Ia), (II), or (IIa), or pharmaceutically acceptable salt thereof, is a compound of Formula (IVj):

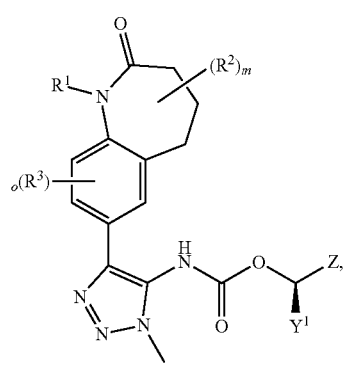

(IVj)

or pharmaceutically acceptable salt thereof;
wherein
m is 0, 1, 2, 3, or 4; and
is 0, 1, 2, or 3.

In some embodiments of the compound of Formula (IIIa)-(IIIg) or (IVa)-(IVj), or pharmaceutically acceptable salt thereof, m is 0, 1, or 2. In some embodiments of the compound of Formula (IIIa)-(IIIg) or (IVa)-(IVj), or pharmaceutically acceptable salt thereof, o is 0 or 1. In some embodiments of the compound of Formula (IIIa)-(IIIg) or (IVa)-(IVj), or pharmaceutically acceptable salt thereof, m is 0 and o is 0. In some embodiments of the compound of Formula (IIIa)-(IIIg) or (IVa)-(IVj), or pharmaceutically acceptable salt thereof, m is 1 and o is 0. In some embodiments of the compound of Formula (IIIa)-(IIIg) or (IVa)-(IVj), or pharmaceutically acceptable salt thereof, m is 2 and o is 0. In some embodiments of the compound of Formula (IIIa)-(IIIg) or (IVa)-(IVj), or pharmaceutically acceptable salt thereof, m is 0 and o is 1.

In some embodiments of the compound of Formula (I), (Ia), (II), (IIa), (IIIa)-(IIIg) or (IVa)-(IVj), or pharmaceutically acceptable salt thereof, each $R^2$, which can be the same or different, is independently selected from hydrogen, halogen, cyano, oxo, $C_{1-4}$ alkyl, $C_{3-10}$ cycloalkyl, 3 to 10 membered heterocyclyl having 1 to 4 heteroatoms independently selected from nitrogen, oxygen, and sulfur, 6 to 10 membered aryl, 5 to 10 membered heteroaryl having 1 to 4 heteroatoms independently selected from nitrogen, oxygen, or sulfur, $-N(R^{2A1})(R^{2A2})$, $-O-R^{2A1}$, $-S-R^{2A1}$, $-C(O)N(R^{2A1})(R^{2A2})$, $-NR^{2A1}C(O)R^{2A2}$, $-NR^{2A1}C(O)N(R^{2A2})(R^{2A2})$, $-S(O)_{0-2}R^{2A1}$, $-S(O)_2N(R^{2A1})(R^{2A2})$, and $-NR^{2A1}S(O)_2R^{2A2}$, wherein each $R^{2A1}$, $R^{2A2}$, and $R^{2A3}$ is independently hydrogen or $C_{1-6}$ alkyl, wherein each $R^2$ alkyl, cycloalkyl, heterocyclic, aryl, and heteroaryl is optionally substituted with 1 to 4 $R^{2B}$, which can be the same or different, wherein each $R^{2B}$ is independently $C_{1-4}$ alkyl, $C_{1-4}$ alkoxy, hydroxy, halogen, or cyano. In some embodiments of the compound of Formula (I), (Ia), (II), (IIa), (IIIa)-(IIIg) or (IVa)-(IVj), or pharmaceutically acceptable salt thereof, each $R^2$, which can be the same or different, is independently $C_{1-4}$ alkyl, 6 to 10 membered aryl, $C_{1-4}$ alkoxy, or halogen, wherein each $C_{1-4}$ alkyl is optionally substituted with 1 to 4 halogen. In some embodiments of the compound of Formula (I), (Ia), (II), (IIa), (IIIa)-(IIIg) or (IVa)-(IVj), or pharmaceutically acceptable salt thereof, each $R^2$, which can be the same or different, is independently selected from $C_{1-4}$ alkyl, $C_{1-4}$ alkoxy, and halogen. In some embodiments of the compound of Formula (I), (Ia), (II), (IIa), (IIIa)-(IIIg) or (IVa)-(IVj), or pharmaceutically acceptable salt thereof, each $R^2$, which can be the same or different, is independently $-CH_3$, $-CF_3$, $-C_2H5$, phenyl, or $-F$. In some embodiments of the compound of Formula (I), (Ia), (II), (IIa), (IIIa)-(IIIg) or (IVa)-(IVj), or pharmaceutically acceptable salt thereof, each $R^2$ is halogen. In some embodiments of the compound of Formula (I), (Ia), (II), (IIa), (IIIa)-(IIIg) or (IVa)-(IVj), or pharmaceutically acceptable salt thereof, each $R^2$ is $-F$.

In some embodiments of the compound of Formula (I), (Ia), (II), (IIa), (IIIa)-(IIIg) or (IVa)-(IVj), or pharmaceutically acceptable salt thereof, each $R^3$, which can be the same or different, is independently selected from deuterium, halogen, $C_{1-6}$ alkyl, $C_{3-10}$ cycloalkyl, or $C_{1-4}$ alkoxy, wherein each $C_{1-6}$ alkyl and $C_{3-10}$ cycloalkyl, is optionally substituted with 1 to 3 halogens. In some embodiments of the compound of Formula (I), (Ia), (II), (IIa), (IIIa)-(IIIg) or (IVa)-(IVj), or pharmaceutically acceptable salt thereof, each $R^3$ is halogen. In some embodiments of the compound of Formula (I), (Ia), (II), (IIa), (IIIa)-(IIIg) or (IVa)-(IVj), or pharmaceutically acceptable salt thereof, each $R^3$ is $-F$.

In some embodiments of the compound of Formula (I), (Ia), (II), (IIa), (IIIa)-(IIIg) or (IVa)-(IVj), or pharmaceutically acceptable salt thereof, $Y^1$ is hydrogen, deuterium, or $C_{1-6}$ alkyl optionally substituted with 1 to 3 substituents, which can be the same or different, each independently selected from deuterium, halogen, cyano, $C_{2-3}$ alkynyl, $C_{1-4}$ alkoxy, and —C(O)NH—($C_{1-4}H_{3-9}$). In some embodiments of the compound of Formula (I), (Ia), (II), (IIa), (IIIa)-(IIIg) or (IVa)-(IVj), or pharmaceutically acceptable salt thereof, $Y_1$ is $C_{1-4}$ alkyl optionally substituted with 1 to 3 substituents, which can be the same or different, each independently selected from halogen, cyano, and $C_{1-4}$ alkoxy. In some embodiments of the compound of Formula (I), (Ia), (II), (IIa), (IIIa)-(IIIg) or (IVa)-(IVj), or pharmaceutically acceptable salt thereof, $Y_1$ is methyl optionally substituted with 1 to 3 susbstituents, which can be the same or different, each independently selected from —F, —Cl, —CN, and —O—$CH_3$. In some embodiments of the compound of Formula (I), (Ia), (II), (IIa), (IIIa)-(IIIg) or (IVa)-(IVj), or pharmaceutically acceptable salt thereof, $Y_1$ is —$CH_3$ or —$CH_2F$.

In some embodiments of the compound of Formula (I), (Ia), (II), (IIa), (IIIa)-(IIIg) or (IVa)-(IVj), or pharmaceutically acceptable salt thereof, Z is $C_{1-8}$ alkyl, $C_{1-6}$ alkoxy, $C_{3-6}$ cycloalkyl, $C_{6-12}$ aryl, 3 to 12 membered heterocyclyl having 1 to 4 heteroatoms independently selected from nitrogen, oxygen, and sulfur, or 5 to 12 membered heteroaryl having 1 to 4 heteroatoms independently selected from nitrogen, oxygen, and sulfur, wherein the alkyl, alkoxy, cycloalkyl, aryl, heterocyclyl, or heteroaryl are each optionally substituted with 1 to 3 substituents, which can be the same or different, each independently selected from halogen, cyano, $C_{1-4}$ alkyl, $C_{1-4}$ alkoxy, and $C_{3-6}$ cycloalkyl, wherein the $C_{1-4}$ alkyl is optionally substituted with 1 to 3 substituents, which can be the same or different, each selected from $C_{1-4}$ alkoxy and halogen. In some embodiments of the compound of Formula (I), (Ia), (II), (IIa), (IIIa)-(IIIg) or (IVa)-(IVj), or pharmaceutically acceptable salt thereof, Z is phenyl, optionally substituted with 1 to 3 sustituents, which can be the same or different, each independently selected from halogen and $C_{1-4}$ alkyl. In some embodiments of the compound of Formula (I), (Ia), (II), (IIa), (IIIa)-(IIIg) or (IVa)-(IVj), or pharmaceutically acceptable salt thereof, Z is phenyl, optionally substituted with 1 to 3 substituents, which can be the same or different, each independently selected from —F and —Cl. In some embodiments of the compound of Formula (I), (Ia), (II), (IIa), (IIIa)-(IIIg) or (IVa)-(IVj), or pharmaceutically acceptable salt thereof, Z

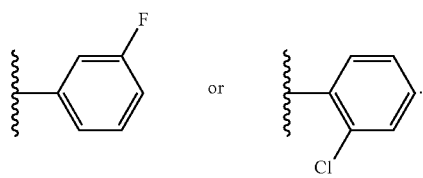 [SMILES: *c1cccc(F)c1 ; *c1ccccc1Cl]

In some embodiments of the compound of Formula (I), (Ia), (II), (IIa), (IIIa)-(IIIg) or (IVa)-(IVj), or pharmaceutically acceptable salt thereof, Z is 5 or 6 membered heteroaryl having 1-3 heteroatoms independently selected from nitrogen, oxygen, and sulfur, wherein the heteroaryl is optionally substituted with 1 to 3 substituents, which can be the same or different, independently selected from halogen and $C_{1-4}$ alkyl. In some embodiments of the compound of Formula (I), (Ia), (II), (IIa), (IIIa)-(IIIg) or (IVa)-(IVj), or pharmaceutically acceptable salt thereof, Z is pyridyl, optionally substituted with 1 to 3 substituents, which can be the same or different, each independently selected from —F, —Cl, —Br, and —$CH_3$. In some embodiments of the compound of Formula (I), (Ia), (II), (IIa), (IIIa)-(IIIg) or (IVa)-(IVj), or pharmaceutically acceptable salt thereof, Z is

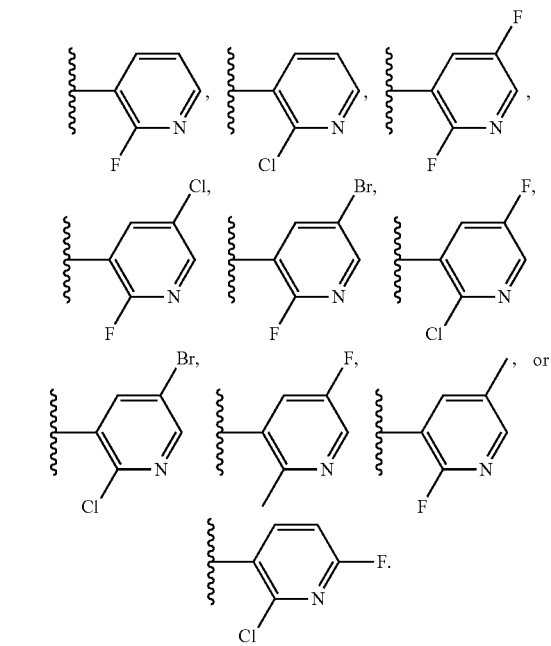

In some embodiments of the compound of Formula (I), (Ia), (II), (IIa), (IIIa)-(IIIg) or (IVa)-(IVj), or pharmaceutically acceptable salt thereof $Y_1$ is —$CH_3$, and Z is

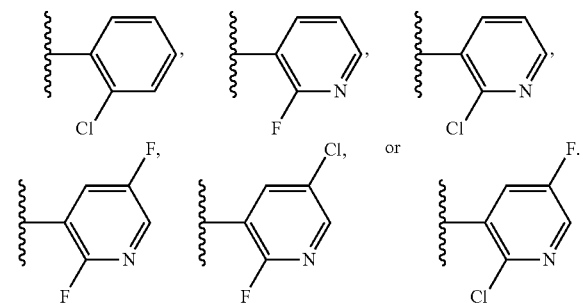

In some embodiments of the compound of Formula (I), (Ia), (II), (IIa), (IIIa)-(IIIg) or (IVa)-(IVj), or pharmaceutically acceptable salt thereof $Y_1$ is —$CH_3$, and Z is

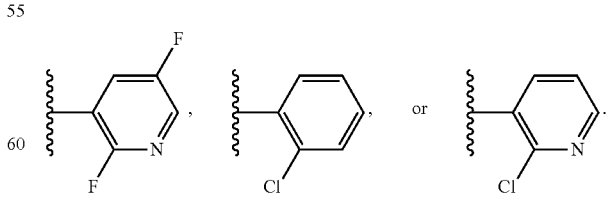

In some embodiments the compound of Formula (I), (Ia), (II), (IIa), (IIIa)-(IIIg) or (IVa)-(IVj), or pharmaceutically acceptable salt thereof, is selected from the group consisting of:

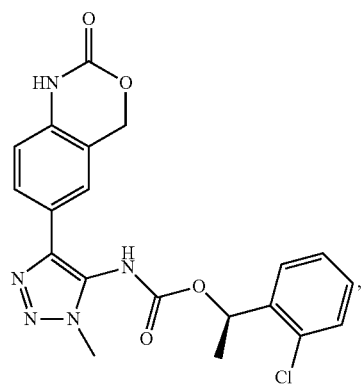
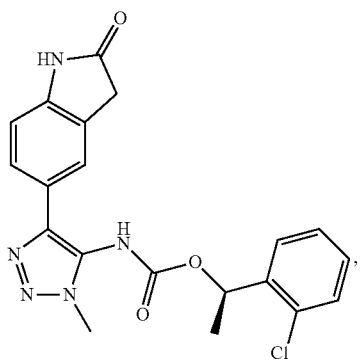
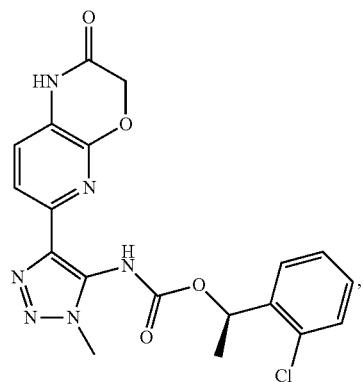
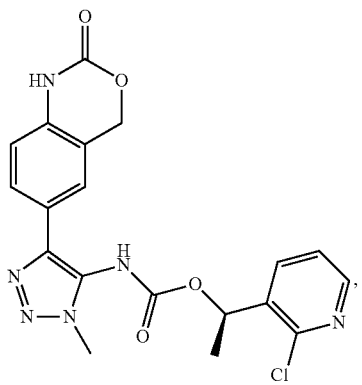
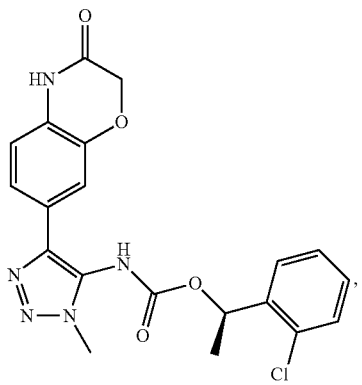

31
-continued
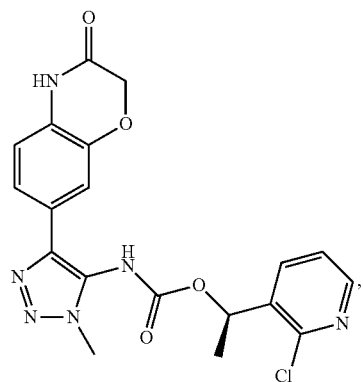
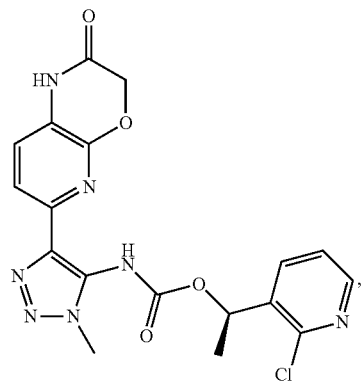
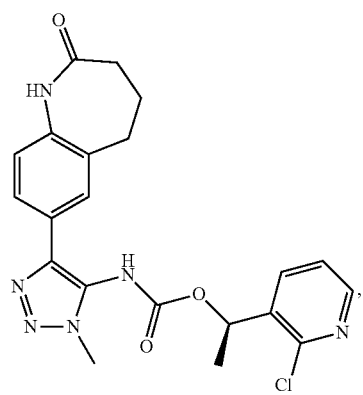
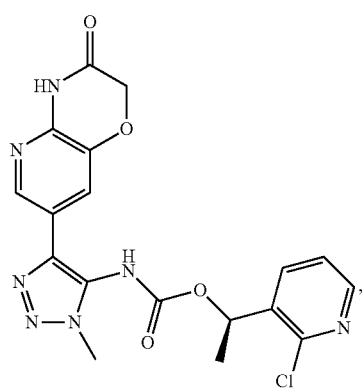
32
-continued
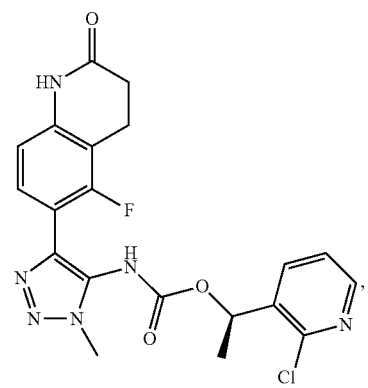
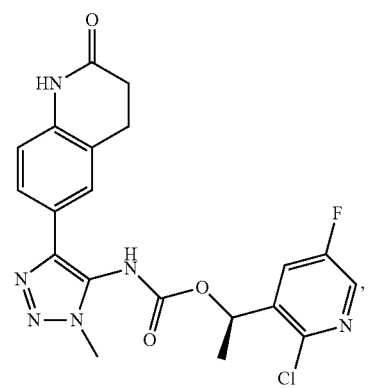
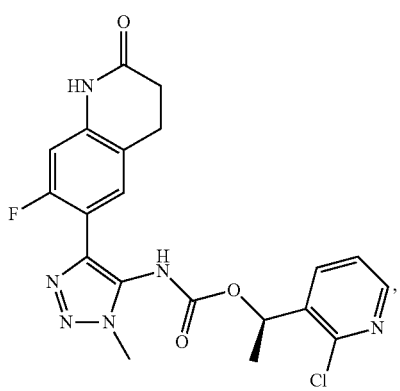
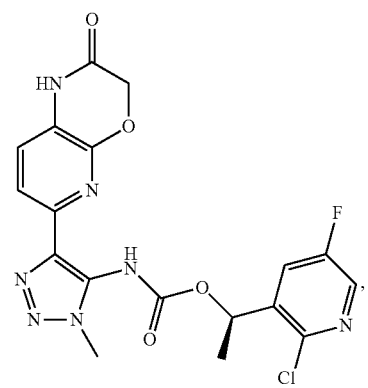

33
-continued
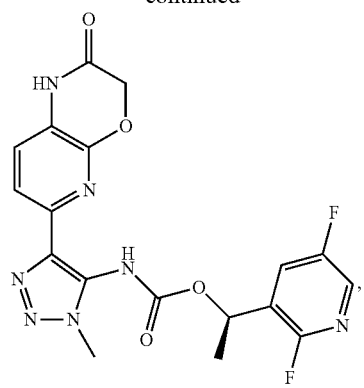
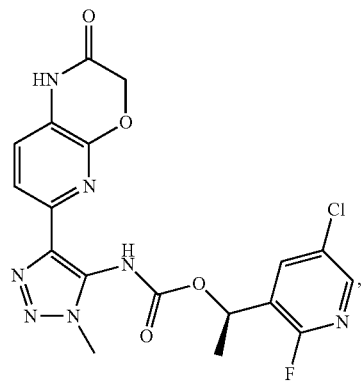
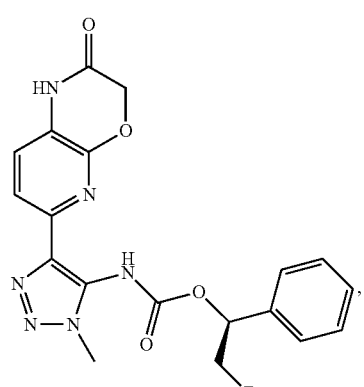
34
-continued
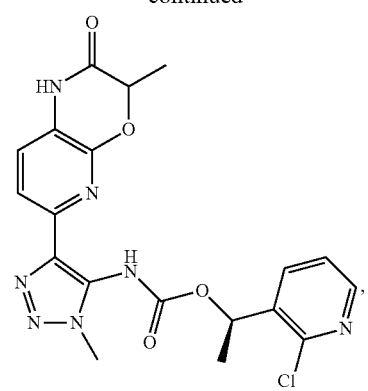
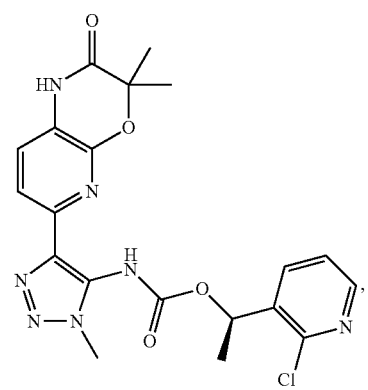
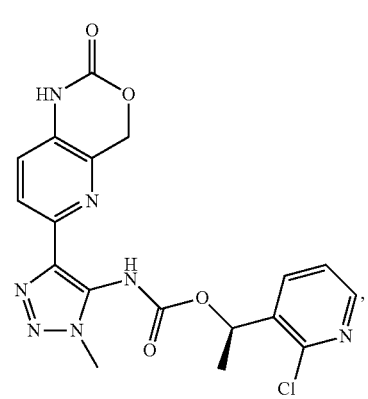
and -continued

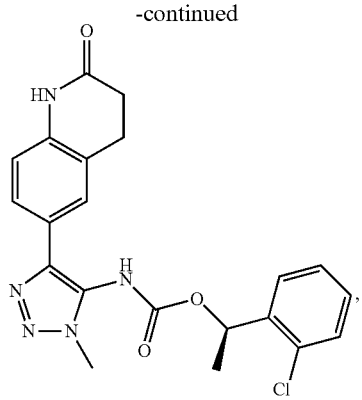

or pharmaceutically acceptable salt thereof.

In some embodiments the compound of Formula (I), (Ia), (II), (IIa), (IIIa)-(IIIg) or (IVa)-(IVj), or pharmaceutically acceptable salt thereof, is selected from the group consisting of:

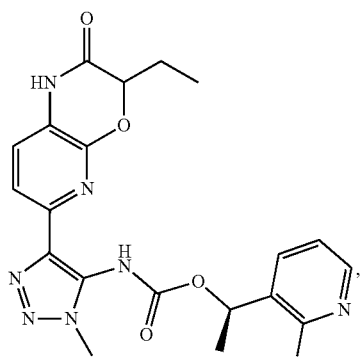

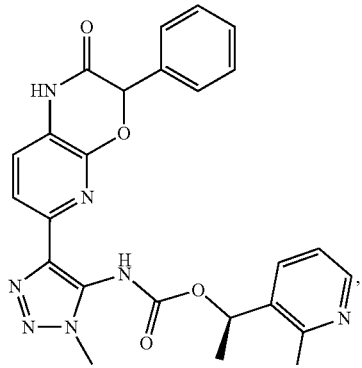

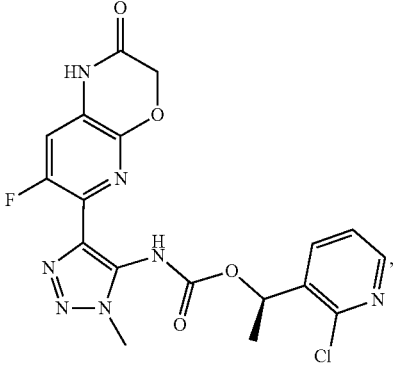

-continued

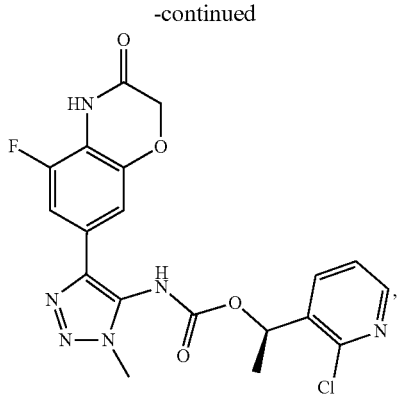

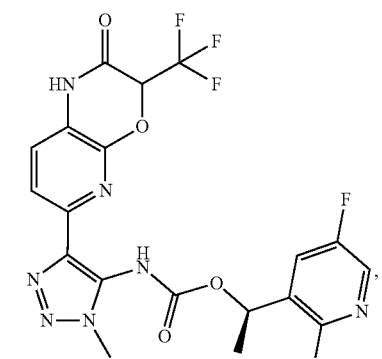

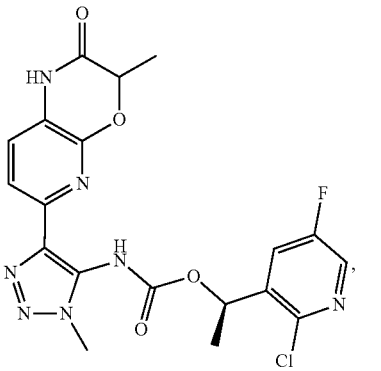

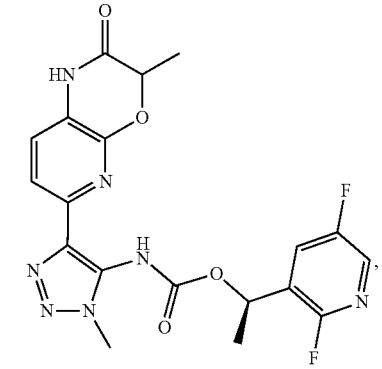

, and or a pharmaceutically acceptable salt thereof.

In some embodiments, the compound of Formula (I), (Ia), (II), (IIa), (IIIa)-(IIIg), or (IVa)-(IVj), or pharmaceutically acceptable salt thereof, is:

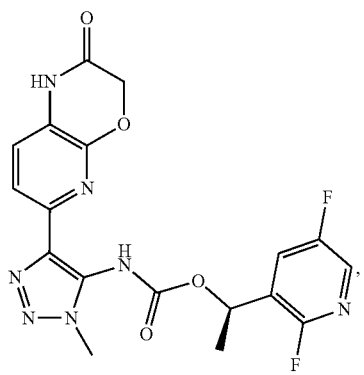 [SMILES: C[C@@H](OC(=O)Nc1c(-c2ccc3c(n2)OCC(=O)N3)nnn1C)c1cc(F)cnc1F]

or pharmaceutically acceptable salt thereof.

In some embodiments, the compound of Formula (I), (Ia), (II), (IIa), (IIIa)-(IIIg), or (IVa)-(IVj), or pharmaceutically acceptable salt thereof, is:

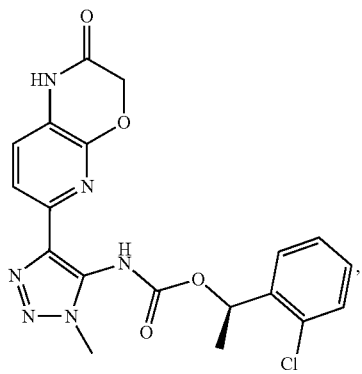 [SMILES: C[C@@H](OC(=O)Nc1c(-c2ccc3c(n2)OCC(=O)N3)nnn1C)c1ccccc1Cl]

or pharmaceutically acceptable salt thereof.

In some embodiments, the compound of Formula (I), (Ia), (II), (IIa), (IIIa)-(IIIg), or (IVa)-(IVj), or pharmaceutically acceptable salt thereof, is:

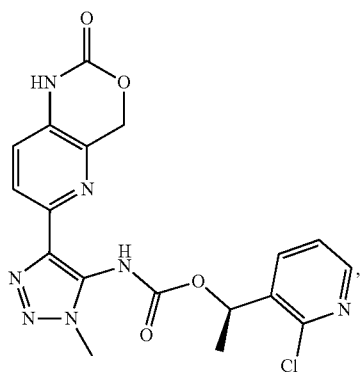 [SMILES: C[C@@H](OC(=O)Nc1c(-c2ccc3c(n2)COC(=O)N3)nnn1C)c1cccnc1Cl]

or pharmaceutically acceptable salt thereof.

In some embodiments, the compound of Formula (I), (Ia), (II), (IIa), (IIIa)-(IIIg), or (IVa)-(IVj), or pharmaceutically acceptable salt thereof, is:

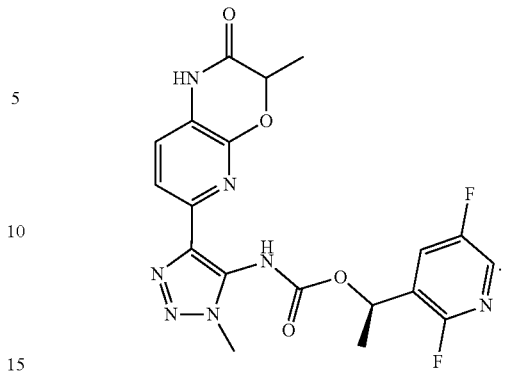

or pharmaceutically acceptable salt thereof.

Pharmaceutical Compositions and Modes of Administration

Furthermore, the present disclosure provides pharmaceutical compositions comprising at least one compound of the present disclosure, or a prodrug compound thereof, or a pharmaceutically acceptable salt or solvate thereof as active ingredient together with a pharmaceutically acceptable carrier.

The pharmaceutical composition of the present disclosure may additionally comprise one or more other compounds as active ingredients like a prodrug compound or other enzyme inhibitors.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

In some embodiments, the compounds of the present disclosure may also be used as salts with various countercations to yield an orally available formulation.

The compounds of the present disclosure may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present disclosure. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In some embodiments, compounds of the present disclosure are administered orally.

Kits

Provided herein are also kits that include a compound of the disclosure, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Treatment Methods and Uses

The disclosure further relates to the use of compounds disclosed herein for the treatment and/or prophylaxis of diseases and/or conditions through binding of LPAR1 by said compounds. Further, the present disclosure relates to the use of said compounds for the preparation of a medicament for the treatment and/or prophylaxis of diseases and/or conditions through binding of LPAR1 by said compounds.

Medicaments as referred to herein may be prepared by conventional processes, including the combination of a compound according to the present disclosure and a pharmaceutically acceptable carrier.

In some embodiments, provided herein is a method of treating and/or preventing an LPAR1-mediated disease or condition in a patient in need thereof, comprising administering to the patient a therapeutically effective amount of a compound of Formula (I), (Ia), (II), (IIa), (IIIa)-(IIIg), or (IVa)-(IVj), or a pharmaceutically acceptable salt thereof, or a composition comprising a compound of Formula (I), (Ia), (II), (IIa), (IIIa)-(IIIg), or (IVa)-(IVj), or a pharmaceutically acceptable salt thereof.

In some embodiments, the LPAR1-mediated disease or condition includes those wherein an absolute or relative excess of LPA is present and/or observed.

In some embodiments, the LPAR1-mediated disease or condition includes fibrosis, wound healing, cancer, pain, respiratory disorders, allergic disorders, nervous system disorders, cardiovascular disorders, or inflammatory disorders.

In some embodiments, the LPAR1-mediated disease or condition includes fibrosis. In some embodiments, fibrosis includes pulmonary fibrosis, renal fibrosis, hepatic fibrosis, ocular fibrosis, or cardiac fibrosis.

In some embodiments, the LPAR1-mediated disease or condition includes pulmonary fibrosis. In some embodiments, pulmonary fibrosis includes idiopathic pulmonary fibrosis (IPF). In some embodiments pulmonary fibrosis includes Progressive Fibrotic interstitial lung disease (PF-ILD). In some embodiments, pulmonary fibrosis includes pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced).

In some embodiments, the LPAR1-mediated disease or condition includes renal fibrosis. In some embodiments, renal fibrosis includes chronic nephropathies associated with injury/ibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; gut fibrosis, e.g., scleroderma, and radiation induced gut fibrosis.

In some embodiments, the LPAR1-mediated disease or condition includes liver fibrosis. In some embodiments, liver fibrosis includes liver cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis.

In some embodiments, the LPAR1-mediated disease or condition includes head and neck fibrosis, e.g., radiation induced.

In some embodiments, the LPAR1-mediated disease or condition includes corneal scarring, e.g., due to LASIK (laser-assisted in situ keratomileusis), corneal transplantation, or trabeculectomy. In some embodiments, a compound of Formula (I), (Ia), (II), (IIa), (IIIa)-(IIIg), or (IVa)-(IVj), or a pharmaceutically acceptable salt thereof, is used to improve the corneal sensitivity decrease caused by corneal operations such as LASIK or cataract operation, corneal sensitivity decrease caused by corneal degeneration, and dry eye symptom caused thereby. In some embodiments, a compound of Formula (I), (Ia), (II), (IIa), (IIIa)-(IIIg), or (IVa)-(IVj), or a pharmaceutically acceptable salt thereof, is used in the treatment or prevention of ocular inflammation and allergic conjunctivitis, vernal keratoconjunctivitis, and papillary conjunctivitis. In some embodiments, a compound of Formula (I), (Ia), (II), (IIa), (IIIa)-(IIIg), or (IVa)-(IVj), or a pharmaceutically acceptable salt thereof, is used in the treatment or prevention of Sjogren disease or inflammatory disease with dry eyes.

In some embodiments, the LPAR1-mediated disease or condition includes another fibrotic condition, such as hypertrophic scarring and keloids, e.g., burn induced or surgical, sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In some embodiments, the LPAR1-mediated disease or condition includes pain. In some embodiments, pain includes neuropathic pain. In some embodiments, pain includes acute pain. In some embodiments, pain includes chronic pain.

In some embodiments, the LPAR1-mediated disease or condition includes cancer. In some embodiments, cancer includes ovarian cancer, colon cancer, prostate cancer, breast cancer, melanoma, head and neck cancer, bowel cancer (colorectal cancer), and thyroid cancer. In some embodiments, cancer includes solid tumors, such as (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases. In some embodiments, cancer includes, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hair) cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastema, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive, neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, the LPAR1-mediated disease or condition includes a respiratory or allergic disorder. In some embodiments, the respiratory or allergic disorder includes asthma, peribronchiolar fibrosis, obliterative bronchiolitis, and chronic obstructive pulmonary disease (COPD). In some embodiments, the COPD includes chronic bronchitis or emphysema, pulmonary hypertension, interstitial lung fibrosis and/or airway inflamrnation, and cystic fibrosis. In some embodiments, the respiratory disease includes adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-mduced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, and hypoxia.

In some embodiments, the LPAR1-mediated disease or condition includes a nervous system disorder. In some embodiments, the nervous system disorder includes Alzheimer's Disease, cerebral edema, cerebral ischemia, stroke, multiple sclerosis, neuropathies, Parkinson's Disease, a nervous condition found after blunt or surgical trauma (including post-surgical cognitive dysfunction and spinal cord or bram stem injury), as well as the neurological aspects of disorders such as degenerative disk disease and sciatica.

In some embodiments, the LPAR1-mediated disease or condition includes a cardiovascular disorder. In some embodiments, the cardiovascular disorder includes arrhythmia (atrial or ventricular or both); atherosclerosis and its sequelae; angina; cardiac rhythm disturbances; myocardial ischemia; myocardial infarction; cardiac or vascular aneurysm; vasculitis; stroke; peripheral obstructive arteriopathy of a limb, an organ, or a tissue; reperfusion injury following ischemia of the brain, heart or other organ or tissue; endotoxic, surgical, or traumatic shock; hypertension; valvular heart disease; heart failure; abnormal blood pressure; shock;

vasoconstriction (including that associated with migraines); vascular abnormality, and a cardiovascular insufficiency limited to a single organ or tissue.

In some embodiments, the LPAR1-mediated disease or condition includes lung fibrosis, kidney fibrosis, liver fibrosis, scarring, asthma, rhinitis, chronic obstructive pulmonary disease (COPD), pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions.

In some embodiments, the LPAR1-mediated disease or condition is a liver disease. In some embodiments, the liver disease is hepatitis C, liver cancer, familial combined hyperlipidemia, non-alcoholic fatty liver disease (NAFLD), progressive familial intrahepatic cholestasis, primary biliary cirrhosis (PBC), or (PSC). In some embodiments, the liver disease is PSC. In some embodiments the liver disease comprises portal hypertension. In some embodiments, liver cancer comprises hepatocellular carcinoma (HCC), cholangiocarcinoma, angiosarcoma, or hemangiosarcoma. In some embodiments, liver cancer comprises HCC. In some embodiments, NAFLD comprises steatosis. In some embodiments, NAFLD comprises NASH. In some embodiments, NAFLD or NASH comprises liver fibrosis. In some embodiments, NAFLD or NASH comprises liver cirrhosis. In some embodiments, the NAFLD or NASH comprises compensated liver cirrhosis. In some embodiments, the NAFLD or NASH comprises decompensated liver fibrosis. In some embodiments, the NAFLD comprises HCC. In some embodiments, the liver disease is NASH.

In some embodiments, provided herein is a method of treating and/or preventing NAFLD or NASH in a patient in need thereof, comprising administering to the patient a therapeutically effective amount of a compound of Formula (I), (Ia), (II), (IIa), (IIIa)-(IIIg), or (IVa)-(IVj), or pharmaceutically acceptable salt thereof, or a composition comprising a compound of (I), (Ia), (II), (IIa), (IIIa)-(IIIg), or (IVa)-(IVj), or pharmaceutically acceptable salt thereof. In some embodiments, NAFLD or NASH comprise liver fibrosis. In some embodiments, NAFLD or NASH comprise liver cirrhosis. In some embodiments, liver cirrhosis is compensated liver cirrhosis. In some embodiments, liver cirrhosis is decompensated liver cirrhosis. In some embodiments NAFLD or NASH comprise HCC.

In some embodiments, provided herein is a method of preventing a liver disease or condition in a patient in need thereof, comprising administering to the patient a therapeutically effective amount of a compound of Formula (I), (Ia), (II), (IIa), (IIIa)-(IIIg), or (IVa)-(IVj), or pharmaceutically acceptable salt thereof, or a composition comprising a compound of (I), (Ia), (II), (IIa), (IIIa)-(IIIg), or (IVa)-(IVj), or pharmaceutically acceptable salt thereof. In some embodiments, the liver disease or condition is liver fibrosis. In some embodiments, the liver disease or condition is liver cirrhosis. In some embodiments, liver cirrhosis is compensated liver cirrhosis. In some embodiments, liver cirrhosis is decompensated liver cirrhosis. In some embodiments, the liver disease or condition is HCC.

In some embodiments, the present disclosure relates to the use of compounds according to Formula (I), (Ia), (II), (IIa), (IIIa)-(IIIg), or (IVa)-(IVj), or pharmaceutically acceptable salts thereof, in the preparation of a medicament for the prophylaxis and/or treatment of an LPAR1-mediated disease or condition disclosed herein.

Dosage

The effective dosage of active ingredient employed may vary depending on the particular compound employed, the mode of administration, the condition being treated and the severity of the condition being treated. Such dosage may be ascertained readily by a person skilled in the art.

When treating or preventing an LPAR1 mediated disease or condition for which compounds of the present disclosure are indicated, generally satisfactory results are obtained when the compounds of the present disclosure are administered at a daily dosage of from about 0.1 milligram to about 300 milligram per kilogram of animal body weight. In some embodiments, the compounds of the present disclosure are given as a single daily dose or in divided doses two to six times a day, or in sustained release form. For most large mammals, the total daily dosage is from about 1 milligram to about 1000 milligrams, or from about 1 milligram to about 50 milligrams. In the case of a 70 kg adult human, the total daily dose will generally be from about 0.1 milligrams to about 200 milligrams. This dosage regimen may be adjusted to provide the optimal therapeutic response. In some embodiments, the total daily dosage is from about 1 milligram to about 900 milligrams, about 1 milligram to about 800 milligrams, about 1 milligram to about 700 milligrams, about 1 milligram to about 600 milligrams, about 1 milligram to about 400 milligrams, about 1 milligram to about 300 milligrams, about 1 milligram to about 200 milligrams, about 1 milligram to about 100 milligrams, about 1 milligram to about 50 milligrams, about 1 milligram to about 20 milligram, or about 1 milligram to about 10 milligrams.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are frequently alternated with resting periods of about 1 to 28 days, commonly about 7 days or about 14 days, between cycles. The treatment cycles, in other embodiments, may also be continuous.

In some embodiments, the methods provided herein comprise administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Combinations

In some embodiments, a compound of Formula (I), (Ia), (II), (IIa), (IIIa)-(IIIg), or (IVa)-(IVj), provided herein, or pharmaceutically acceptable salt thereof, is administered in combination with one or more additional therapeutic agents to treat or prevent a disease or condition disclosed herein. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the pharmaceutical compositions provided herein have a compound of Formula (I), (Ia), (II), (IIa), (IIIa)-(IIIg), or (IVa)-(IVj) provided herein, or pharmaceutically acceptable salt thereof, and one or more additional therapeutic agents. In some embodiments, the one or more additional therapeutic agents are one, two, three, or four additional therapeutic agents. In some embodiments, the one or more additional therapeutic agents are one additional therapeutic agent. In some embodiments, the one or more additional therapeutic agents are two additional therapeutic agents. In some embodiments, the one or more additional therapeutic agents are three additional therapeutic agents. In some embodiments, the one or more additional therapeutic agents are four additional therapeutic agents.

In some embodiments, the one or more additional therapeutic agents are selected from a(n) angiotensin converting enzyme (ACE) inhibitor, Adenosine A3 receptor agonist, Adiponectin receptor agonist, AKT protein kinase inhibitor, AMP kinase activator, AMP-activated protein kinase (AMPK) activator, Amylin receptor agonist, Angiotensin II AT-1 receptor antagonist, Androgen receptor agonist, Apoptosis signal-regulating kinase 1 (ASK1) inhibitor, ATP citrate lyase inhibitor, Apolipoprotein C3 (APOC3) antagonist, Autophagy protein modulator, Autotaxin inhibitors, Ax1 tyrosine kinase receptor inhibitor, Bax protein stimulator, Bioactive lipid, Calcitonin agonist, Cannabinoid receptor modulator, Caspase inhibitor, Caspase-3 stimulator, Cathepsin inhibitor (e.g., cathepsin B inhibitor), Caveolin 1 inhibitor, CCR2 chemokine antagonist, CCR3 chemokine antagonist, CCR5 chemokine antagonist, CD3 antagonist, Chloride channel stimulator, cholesterol solubilizer, CNR1 inhibitor, Cyclin D1 inhibitor, Cytochrome P450 7A1 inhibitor, Cytochrome P450 2E1 (CYP2E1) inhibitor, Diacylglycerol O acyltransferase 1 inhibitor (DGAT1) inhibitor, Diacylglycerol O acyltransferase 1 inhibitor (DGAT2) inhibitor, CXCR4 chemokine antagonist, Dipeptidyl peptidase IV inhibitor, Endosialin modulator, Endothelial nitric oxide synthase stimulator, Eotaxin ligand inhibitor, Extracellular matrix protein modulator, Farnesoid X receptor agonist, Fatty acid synthase inhibitors, FGF1 receptor agonist, Fibroblast activation protein (FAP) inhibitor, Fibroblast growth factor receptor ligands (e.g., FGF-15, FGF-19, FGF-21), Fish oil, Galectin-3 inhibitor, Glucagon receptor agonist, Glucagon-like peptide 1 receptor agonist, Glucocorticoid receptor antagonist, Glucose 6-phosphate 1-dehydrogenase inhibitor, Glutaminase inhibitor, Glutathione precursor, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, HMG CoA reductase inhibitor, 11β-Hydroxysteroid dehydrogenase (11β-HSD1) inhibitor, Hypoxia inducible factor-2 alpha inhibitor, IL-1β antagonist, IL-6 receptor agonist, IL-10 agonist, IL-11 antagonist, IL-17 antagonist, Ileal sodium bile acid cotransporter inhibitor, Insulin sensitizer, Insulin ligand agonist, Insulin receptor agonist, integrin modulator, Integrin antagonist intereukin-1 receptor-associated kinase 4 (IRAK4) inhibitor, Jak2 tyrosine kinase inhibitor, Ketohexokinase (KHK) inhibitors, Klotho beta stimulator, leptin, leptin analog, 5-Lipoxygenase inhibitor, Lipoprotein lipase inhibitor, Liver X receptor, LPL gene stimulator, Lysophosphatidate-1 receptor (LPAR-1) antagonist, Lysyl oxidase homolog 2 (LOXL2) inhibitor, LXR inverse agonist, Macrophage mannose receptor 1 modulator, Matrix metalloproteinase (MMPs) inhibitor, MCH receptor-1 antagonist, MEKK-5 protein kinase inhibitor, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21 (miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin-1 stimulator, NADPH oxidase inhibitor (NOX), Nicotinic acid receptor 1 agonist, P2X7 purinoceptor modulator, P2Y13 purinoceptor stimulator, PDE 3 inhibitor, PDE 4 inhibitor, PDE 5 inhibitor, PDGF receptor beta modulator, Peptidyl-prolyl cis-trans isomerase A inhibitor, Phenylalanine hydroxylase stimulator, Phospholipase C inhibitor, PPAR alpha agonist, PPAR gamma agonist, PPAR delta agonist, PPAR gamma modulator, PPAR alpha/delta agonist, PPAR alpha/gamma/delta agonist, Protease-activated receptor-2 antagonist, Protein kinase modulator, Rho associated protein kinase 2 (ROCK2) inhibitor, Snitrosoglutathione reductase (GSNOR) enzyme inhibitor, Sodium glucose transporter-2 (SGLT2) inhibitor, SREBP transcription factor inhibitor, STAT-1 inhibitor, STAT-3 modulator, Stearoyl CoA desaturase-1 inhibitor, Snitrosoglutathione reductase (GSNOR) enzyme inhibitor, Suppressor of cytokine signalling-1 stimulator, Suppressor of cytokine signalling-3 stimulator, Spleen tyorosine kinase (SYK) inhibitor, Transforming growth factor β (TGF-β), TGF-β antagonist (e.g., TGF-β1 antagonist, TGF-β2 antagonist, TGF-β3 antagonist, latent TGF β complex modulator), TGF-β receptor antagonist, Transforming growth factor β activated Kinase 1 (TAK1), Thyroid hormone receptor beta agonist, Toll-like receptor (TLR)-4 antagonist, Transglutaminase inhibitor, Tumor necrosis factor alpha (TNFα) ligand inhibitor, Tumor Progression Locus 2 (Tpl2) kinase inhibitor, Tyrosine kinase receptor modulator, GPCR modulator, nuclear hormone receptor modulator, WNT modulators, YAP/TAZ modulator, and Zonulin inhibitor.

Non-limiting examples of the one or more additional therapeutic agents include:

ACE inhibitors, such as enalapril;

Acetyl CoA carboxylase (ACC) inhibitors, such as NDI-010976 (firsocostat), DRM-01, gemcabene, PF-05175157, QLT-091382 or PF-05221304;

Acetyl CoA carboxylase/Diacylglycerol O acyltransferase 2 inhibitors, such as PF-07055341;

Acetaldehyde dehydrogenase inhibitors, such as ADX-629;

Adenosine receptor agonists, such as CF-102 (namodenoson), CF-101, CF-502, or CGS21680;

Adiponectin receptor agonists, such as ADP-355 or ADP-399;

Amylin/calcitonin receptor agonists, such as KBP-042 or KBP-089;

AMP activated protein kinase stimulators, such as PXL-770 or O-304;

AMP kinase activators/ATP citrate lyase inhibitors, such as as bempedoic acid (ETC-1002, ESP-55016);

AMP activated protein kinase/Endothelial nitric oxide synthase/NAD-dependent deacetylase sirtuin-1 stimulators, such as NS-0200 (leucine+metformin+sildenafil);

Androgen receptor agonists, such as LPCN-1144;

Angiotensin II AT-1 receptor antagonists, such as irbesartan;

Angiopoietin-related protein-3 inhibitors, such as IONIS-ANGPTL3-LRx;

Autotaxin inhibitors, such as PAT-505, PAT-048, GLPG-1690, X-165, PF-8380, AM-063, or BBT-877;

Ax1 tyrosine kinase receptor inhibitors, such as bemcentinib (BGB-324, R-428);

Bax protein stimulators, such as CBL-514;

Bioactive lipids, such as DS-102;

Cannabinoid receptor type 1 (CNR1) inhibitors, such as namacizumab, GWP-42004, REV-200, or CRB-4001;
Caspase inhibitors, such as emricasan;
Pan cathepsin B inhibitors, such as VBY-376;
Pan cathepsin inhibitors, such as VBY-825;
CCR2/CCR5 chemokine antagonists, such as cenicriviroc, maraviroc, CCX-872, or WXSH-0213;
CCR2 chemokine antagonists, such as propagermanium;
CCR2 chemokine/Angiotensin II AT-1 receptor antagonists, such as DMX-200, or DMX-250;
CCR2/CCR5 chemokine antagonists and FXR agonists, such as LJC-242 (tropifexor+cenivriviroc); CCR3 chemokine antagonists, such as bertilimumab;
Chloride channel stimulators, such as cobiprostone, or lubiprostone;
CD3 antagonists, such as NI-0401 (foralumab);
CXCR4 chemokine antagonists, such as AD-214;
Diglyceride acyltransferase 1 (DGAT1) inhibitors, such as GSK-3008356;
Diacylglycerol O acyltransferase 1 (DGAT1)/Cytochrome P450 2E1 inhibitors (CYP2E1), such as SNP-610;
Diglyceride acyltransferase 2 (DGAT2) inhibitors, such as IONIS-DGAT2Rx, or PF-06865571;
Dipeptidyl peptidase IV inhibitors, such as linagliptin or evogliptin;
Eotaxin ligand inhibitors, such as bertilimumab or CM-101;
Extracellular matrix protein modulators, such as CNX-024;
Farnesoid X receptor (FXR) agonists, such as AGN-242266, AGN-242256, EP-024297, RDX-023, BWL-200, AKN-083, EDP-305, GNF-5120, GS-9674, LMB-763, obeticholic acid, Px-102, Px-103, M790, M780, M450, M-480, MET-409, PX20606, EYP-001, TERN-101, TC-100, INT-2228;
Farnesoid X receptor (FXR)/G-protein coupled bile acid receptor 1 (TGR5) agonists, such as INT-767;
Fatty acid synthase inhibitors, such as TVB-2640;
FGF receptor agonists/Klotho beta stimulators, such as BFKB-8488A (RG-7992);
Fibroblast growth factor 19 (rhFGF19)/cytochrome P450 (CYP)7A1 inhibitors, such as NGM-282;
Fibroblast growth factor 21 (FGF-21) ligand, such as BMS-986171, BI089-100, B-1344, or BMS-986036;
Fibroblast growth factor 21 (FGF-21)/glucagon like peptide 1 (GLP-1) agonists, such as YH-25723 (YH-25724; YH-22241) or AKR-001;
Fish oil compositions, such as icosapent ethyl (Vascepa®);
Galectin-3 inhibitors, such as GR-MD-02, GB-1107 (Gal-300), or GB1211 (Gal-400);
Glucagon-like peptide 1 receptor (GLP1R) agonists, such as AC-3174, liraglutide, cotadutide (MEDI-0382), exenatide, SAR-425899, LY-3305677, HM-15211, YH-25723, YH-GLP1, RPC-8844, PB-718, or semaglutide;
Glucocorticoid receptor antagonists, such as CORT-118335 (miricorilant);
Glucose 6-phosphate 1-dehydrogenase inhibitors, such as ST001;
G-protein coupled bile acid receptor 1 (TGR5) agonists, such as RDX-009 or INT-777;
Heat shock protein 47 (HSP47) inhibitors, such as ND-L02-s0201;
HMG CoA reductase inhibitors, such as atorvastatin, fluvastatin, pitavastatin, pravastatin, rosuvastatin, or simvastatin;
Hypoxia inducible factor-2 alpha inhibitors, such as PT-2567;
IL-10 agonists, such as peg-ilodecakin;
Ileal sodium bile acid cotransporter inhibitors, such as odevixibat (A-4250), volixibat potassium ethanolate hydrate (SHP-262), GSK2330672, CJ-14199, or elobixibat (A-3309);
Insulin sensitizers, such as, KBP-042, MSDC-0602K, MSDC-5514, Px-102, RG-125 (AZD4076), VVP-100X, CB-4211, or ETI-101;
Insulin ligand/dsInsulin receptor agonists, such as ORMD-0801;
Integrin antagonists, such as IDL-2965;
IL-6 receptor agonists, such as KM-2702;
Ketohexokinase (KHK) inhibitors, such as PF-06835919;
beta Klotho (KLB)—FGF1c agonist, such as MK-3655 (NGM-313);
5-Lipoxygenase inhibitors, such as tipelukast (MN-001), DS-102 (AF-102);
Lipoprotein lipase inhibitors, such as CAT-2003;
LPL gene stimulators, such as alipogene tiparvovec;
Liver X receptor (LXR) modulators, such as PX-L603, PX-L493, BMS-852927, T-0901317, GW-3965, or SR-9238;
Lysophosphatidate-1 receptor antagonists, such as BMT-053011, UD-009 (CP-2090), AR-479, ITMN-10534, BMS-986020, or KI-16198;
Lysyl oxidase homolog 2 inhibitors, such as simtuzumab or PXS-5382A (PXS-5338);
Macrophage mannose receptor 1 modulators, such as tilmanocept-Cy3 (technetium Tc 99m tilmanocept);
Membrane copper amine oxidase (VAP-1) inhibitors, such as TERN-201;
MEKK-5 protein kinase (ASK-1) inhibitors, such as GS-4997, SRT-015, or GS-444217, GST-HG-151;
MCH receptor-1 antagonists, such as CSTI-100 (ALB-127158);
Methionine aminopeptidase-2 inhibitors, such as ZGN-839, ZGN-839, or ZN-1345;
Methyl CpG binding protein 2 modulators, such as mercaptamine;
Mitochondrial uncouplers, such as 2,4-dinitrophenol or HU6;
Mixed lineage kinase-3 inhibitors, such as URMC-099-C;
Myelin basic protein stimulators, such as olesoxime;
NADPH oxidase ¼ inhibitors, such as GKT-831 or APX-311;
Nicotinic acid receptor 1 agonists, such as ARI-3037MO;
Nitazoxinide;
NACHT LRR PYD domain protein 3 (NLRP3) inhibitors, such as KDDF-201406-03, NBC-6, IFM-514, or JT-194 (JT-349);
Nuclear receptor modulators, such as DUR-928 (DV-928);
P2X7 purinoceptor modulators, such as SGM-1019;
P2Y13 purinoceptor stimulators, such as CER-209;
PDE 3/4 inhibitors, such as tipelukast (MN-001);
PDE 5 inhibitors, such as sildenafil or MSTM-102;
PDGF receptor beta modulators, such as BOT-191 or BOT-509;
Peptidyl-prolyl cis-trans isomerase inhibitors, such as CRV-431 (CPI-432-32), NVP-018, or NV-556 (NVP-025);

Phenylalanine hydroxylase stimulators, such as HepaStem;

PPAR agonists (including PPAR alpha agonists, PPAR alpha/delta agonists, PPAR alpha/delta/gamma agonists, PPAR delta agonists), such as elafibranor (GFT-505), MBX-8025, deuterated pioglitazone R-enantiomer, pioglitazone, DRX-065, saroglitazar, or IVA-337; PPAR alpha agonists, such as aluminum clofibrate, bezafibrate, ciprofibrate, choline fenofibrate, clinofibrate, clofibrate, clofibride, fenofibrate, gemfibrozil, pemafibrate, ronifibrate, simfibrate, an omega-3 fatty acid (fish oil, e.g., icosapent ethyl (Vascepa®), or docosahexaenoic acid), pirinixic acid, GW409544, AZ 242, LY518674, NS-220, AVE8134, BMS-711939, aleglitazar, muraglitzar, or saroglitazar;

PPAR alpha/delta agonists such as elafibranor;

PPAR alpha/delta/gamma agonists such as lanifibranor;

PPAR delta agonists such as seladelpar;

Protease-activated receptor-2 antagonists, such as PZ-235;

Protein kinase modulators, such as CNX-014;

Rho associated protein kinase (ROCK) inhibitors, such as REDX-10178 (REDX-10325) or KD-025;

Semicarbazide-Sensitive Amine Oxidase/Vascular Adhesion Protein-1 (SSAO/VAP-1) Inhibitors, such as PXS-4728A;

S-nitrosoglutathione reductase (GSNOR) enzyme inhibitors, such as SL-891;

Sodium glucose transporter-2 (SGLT2) inhibitors, such as ipragliflozin, remogliflozin etabonate, ertugliflozin, dapagliflozin, tofogliflozin, or sotagliflozin;

SREBP transcription factor inhibitors, such as CAT-2003 or MDV-4463;

Stearoyl CoA desaturase-1 inhibitors, such as aramchol;

Thyroid hormone receptor (THR) beta agonists, such as resmetriom (MGL-3196), MGL-3745, or VK-2809;

TLR-2/TLR-4 antagonists, such as VB-201 (CI-201);

TLR-4 antagonists, such as JKB-121;

Tyrosine kinase receptor modulators, such as CNX-025 or GFE-2137 (repurposed nitazoxanide);

GPCR modulators, such as CNX-023;

Nuclear hormone receptor modulators, such as Px-102;

Xanthine oxidase/Urate anion exchanger 1 (URAT1) inhibitors, such as RLBN-1001, RLBN-1127; and Zonulin Inhibitors, such as lorazotide acetate (INN-202).

In some embodiments, the one or more additional therapeutic agents are selected from A-4250, AC-3174, acetylsalicylic acid, AK-20, alipogene tiparvovec, AMX-342, AN-3015, aramchol, ARI-3037MO, ASP-8232, AZD-2693, bertilimumab, Betaine anhydrous, BI-1467335, BMS-986036, BMS-986171, BMT-053011, BOT-191, BTT-1023, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, fluasterone (ST-002), FT-4101, GKT-831, GNF-5120, GRI-0621, GR-MD-02, GS-300, GS-4997, GS-9674, HTD-1801, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, LC-280140, linagliptin, liraglutide, LJN-452 (tropifexor), LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-160, norursodeoxycholic acid, NVP-022, 0-304, obeticholic acid (OCA), 25HC3S, olesoxime, PAT-505, PAT-048, PBI-4547, pegilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), RPI-500, saroglitazar, semaglutide, simtuzumab, solithromycin, sotagliflozin, statins (atorvastatin, fluvastatin, pitavastatin, pravastatin, rosuvastatin, simvastatin), symbiotic, TCM-606F, TEV-45478, TQA-3526, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, XRx-117, ZGN-839, ZG-5216, ZSYM-008, and ZYSM-007.

In some embodients, the methods and pharmaceutical compositions provided herein include a therapeutically effective amount of an Apoptosis Signal-Regulating Kinase 1 (ASK1) inhibitor and a therapeutically effective amount of an LPAR1 antagonist, wherein the LPAR1 antagonist is a compound of Formula (I), (Ia), (II), (IIa), (IIIa)-(IIIg), or (IVa)-(IVj), provided herein or pharmaceutically acceptable salt thereof.

In some embodiments of the methods and pharmaceutical compositions disclosed herein, the ASK1 inhibitor is GS-4997 (selonsertib, SEL).

ASK1 inhibitors can be synthesized and characterized using methods known to those of skill in the art, such as those described in U.S. 2007/0276050, U.S. 2011/0009410, and U.S. 2013/0197037.

In some embodiments, the methods and pharmaceutical compositions provided herein include a therapeutically effective amount of an Acetyl-CoA Carboxylase (ACC) inhibitor and a therapeutically effective amount of an LPAR1 antagonist, wherein the LPAR1 antagonist is a compound of Formula (I), (Ia), (II), (IIa), (IIIa)-(IIIg), or (IVa)-(IVj), provided herein or pharmaceutically acceptable salt thereof.

In some embodiments of the methods and pharmaceutical compositions disclosed herein, the ACC inhibitor is GS-0976 (firsocostat, FIR).

ACC inhibitors can be synthesized and characterized using methods known to those of skill in the art, such as those described in U.S. Pat. Nos. 9,453,026 and 10,183,951.

In some embodiments, the methods and compositions provided herein include a therapeutically effective amount of a PPAR agonist (e.g., PPAR alpha agonist, PPAR alpha/delta agonist, PPARalpha/delta/gamma agonist, PPAR delta agonist) or fish oil, a therapeutically effective amount of an Acetyl CoA Carboxylase (ACC) inhibitor, such as GS-0976 (firsocostat, FIR), and a therapeutically effective amount of an LPAR1 antagonist, wherein the LPAR1 antagonist is a compound of Formula (I), (Ia), (II), (IIa), (IIIa)-(IIIg), or (IVa)-(IVj), provided herein or pharmaceutically acceptable salt thereof. In some embodiments, the PPAR agonist is a PPAR alpha agonist. In some embodiments, the PPAR alpha agonist is selected from aluminum clofibrate, bezafibrate, ciprofibrate, choline fenofibrate, clinofibrate, clofibrate, clofibride, fenofibrate, gemfibrozil, pemafibrate, ronifibrate, simfibrate, pirinixic acid, GW409544, AZ 242, LY518674, NS-220, AVE8134, BMS-711939, aleglitazar, muraglitzar, and saroglitazar. In some embodiments, the PPAR agonist (e.g., PPAR alpha agonist) is a fibrate. In some embodiments, the PPAR agonist (e.g., PPAR alpha agonist) is fenofibrate. In some embodiments, the PPAR agonist is a PPAR alpha/delta agonist (e.g., elafibranor). In some embodiments, the PPAR agonist is a PPAR alpha/delta/gamma agonist (e.g., lanifibranor). In some embodiments, the PPAR agonist is a PPAR delta agonist (e.g., seladelpar). In some embodiments the fish oil is an omega-3 fatty acid or docosahexaenoic acid. In some embodiments, the fish oil is icosapent ethyl (e.g., Vascepa®).

In some embodiments, the methods and compositions provided herein include a therapeutically effective amount of a Farnesoid X Receptor (FXR) agonist and a therapeutically effective amount of an LPAR1 antagonist, wherein the LPAR1 antagonist is a compound of Formula (I), (Ia), (II), (IIa), (IIIa)-(IIIg), or (IVa)-(IVj), provided herein or pharmaceutically acceptable salt thereof.

In some embodiments of the methods and pharmaceutical compositions disclosed herein, the FXR agonist is GS-9674 (cilofexor, CILO).

In some embodiments of the methods and pharmaceutical compositions disclosed herein, the FXR agonist is a compound having the structure:

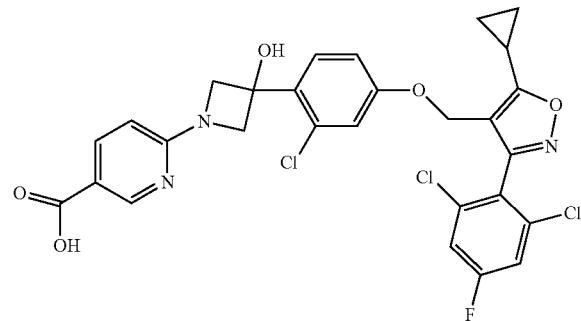 [SMILES: O=C(O)c1ccc(N2CC(O)(c3ccc(OCc4c(-c5c(Cl)cc(F)cc5Cl)noc4C4CC4)cc3Cl)C2)nc1]

or a pharmaceutically acceptable salt thereof.

In some embodiments, the methods and compositions provided herein include a therapeutically effective amount of a GLP-1 receptor agonist and a therapeutically effective amount of an LPAR1 antagonist, wherein the LPAR1 antagonist is a compound of Formula (I), (Ia), (II), or (IIa) provided herein or a pharmaceutically acceptable salt thereof. In some embodiments, the GLP-1 receptor agonist is liraglutide or semaglutide. In some embodiments, the GLP-1 receptor agonist is semaglutide.

In some embodiments, the methods and compositions provided herein include a therapeutically effective amount of a TGFβ antagonist and a therapeutically effective amount of an LPAR1 antagonist, wherein the LPAR1 antagonist is a compound of Formula (I), (Ia), (II), (IIa), (IIIa)-(IIIg), or (IVa)-(IVj), provided herein or pharmaceutically acceptable salt thereof. In some embodiments, the TGFβ antagonist is a TGFβ1-specific antibody. TGFβ1-specific antibodies can be prepared and characterized using methods known to those of skill in the art, such as those described in PCT International Application Publication No. WO 2018/129329 and in U.S. Pat. No. 9,518,112. In some embodiments, the TGFβ antagonist binds to a TGFβ latency-associated peptide (LAP), e.g., TGFβ1-LAP. TGFβ1-LAP-specific antibodies can be prepared and characterized using methods known to those of skill in the art, such as those described in U.S. Pat. No. 8,198,412 or U.S. Pat. No. 10,017,567. In some embodiments, the TGFβ antagonist binds to TGFβ (e.g., TGFβ1) in a context independent manner (e.g., independent of presentation of TGFβ in a specific tissue or organ). In some embodiments, the TGFβ antagonist binds to TGFβ (e.g., TGFβ1) in a context-dependent manner. In some embodiments, the TGFβ antagonist blocks activation of latent TGFβ (e.g., latent TGFβ1) that is localized in extracellular matrix, e.g., in connective tissue of the liver. In some embodiments, the TGFβ antagonist blocks activation of latent TGFβ (e.g., latent TGFβ1) that is localized in the thymus, a lymph node, or in a tumor microenvironment (e.g., in a patient having liver cancer). In some embodiments, the TGFβ antagonist blocks activation of latent TGFβ (e.g., latent TGFβ1) by Latent TGFβ Binding Protein (LTBP). In some embodiments, the TGFβ antagonist blocks activation of latent TGFβ (e.g., latent TGFβ1) by Glycoprotein-A Repetitions Predominant protein (GARP), as described, e.g., in U.S. Pat. No. 10,000,572. In some embodiments, the TGFβ antagonist is ARGX-115. In some embodiments, the TGFβ antagonist is an anti-latency-associated peptide (LAP) antibody that specifically binds to a LAP-TGFβ1 complex. In some embodiments, the anti-LAP antibody specifically binds to LAP-TGFβ 1 complexes in extracellular matrix (ECM), e.g., of connective tissue in the liver. In some embodiments, the anti-LAP antibody specifically binds to LAP-TGFβ1 complexes on the surfaces of certain immunosuppressive cell types, such as regulatory T cells (Tregs), tumor-associated macrophages, or myeloid-derived suppressor cells, e.g., in a tumor microenvironment. In some embodiments, the anti-LAP antibody is a TLS-01 antibody. In some embodiments, the anti-LAP antibody specifically binds to LAP-TGFβ1 complexes in any context. In some embodiments, the anti-LAP antibody is a TLS-02 antibody. In some embodiments, the TGFβ antagonist comprises a TGFβ receptor. In some embodiments, the TGFβ antagonist is a TGFβ receptor-Fc fusion protein. In some embodiments, the TGFβ antagonist is an antibody comprising a TGFβ receptor. TGFβ antagonists comprising a TGFβ receptor that can be useful in connection with the compositions and methods provided herein have been described, e.g., in PCT International Publication Nos. WO 2019/113123 A1 and WO 2019/113464 A1.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that these examples are exemplary and not exhaustive. Many changes can be made in the specific embodiments which are disclosed and still obtain a like or similar result without departing from the spirit and scope of the disclosure.

Compounds disclosed herein can be prepared according to the procedures of the following Schemes and Examples, using appropriate materials and are further exemplified by the following specific examples. Moreover, by utilizing the procedures described herein, in conjunction with ordinary skills in the art, additional compounds of the present disclosure claimed herein can be readily prepared. The examples further illustrate details for the preparation of the compounds of the present disclosure. Those skilled in the art will readily understand that known variations of the conditions and processes of the following preparative procedures can be used to prepare these compounds. For synthesizing compounds which are embodiments described in the present disclosure, inspection of the structure of the compound to be synthesized will provide the identity of each substituent group. In some cases, the identity of the final product can render apparent the identity of the necessary starting materials by a process of inspection, given the examples herein. Compounds can be isolated in the form of their pharmaceutically acceptable salts, such as those described above. Compounds described herein are typically stable and isolatable at room temperature and pressure.

An illustration of the preparation of compounds disclosed herein is shown below. Unless otherwise indicated, variables have the same meaning as described above. The examples presented below are intended to illustrate particular embodiments of the disclosure. Suitable starting materials, building blocks and reagents employed in the synthesis as described below are commercially available from AbovChem, Acros Organics, Astatech, Combi Blocks, Oakwood Chemical, or Sigma-Aldrich, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Schemes

Scheme A provides a general synthesis of bicyclic triazole carbamates (IX). Bicyclic halide VII can be readily prepared from electrophilic aromatic halogenation of the corresponding nitrogen-containing bicycle. Step one describes a general synthesis of bicyclic-containing triazole carboxylic acids (VIII) via cross coupling reaction. Bicyclic halide (VII) can first be converted to the corresponding boronic ester such as pinacol boronate via Miyaura borylation, and then subjected to Suzuki reaction conditions with bromo triazole carboxylic acid (III) to furnish the desired bicyclic triazole carboxylic acid (VIII). Alternatively, bromo triazole carboxylic acid (III) can first be converted to an organo-zinc species via lithium-halogen exchange and trapping with zinc chloride. Next, Negishi cross coupling with bicyclic halide (VII) provides the desired bicyclic triazole carboxylic acid (VIII).

Step two describes a general synthesis of carbamate-containing bicyclic triazoles (IX). A bicyclic triazole carboxylic acid (VIII) undergoes a Curtius rearrangement when treated with diphenylphosphoryl azide (DPPA), or alternatively with 1-propanephosphonic anhydride (T3P) solution and azidotrimethylsilane. The intermediate isocyanate is then trapped with an alcohol (V) to provide the desired bicyclic triazole carbamate (IX).

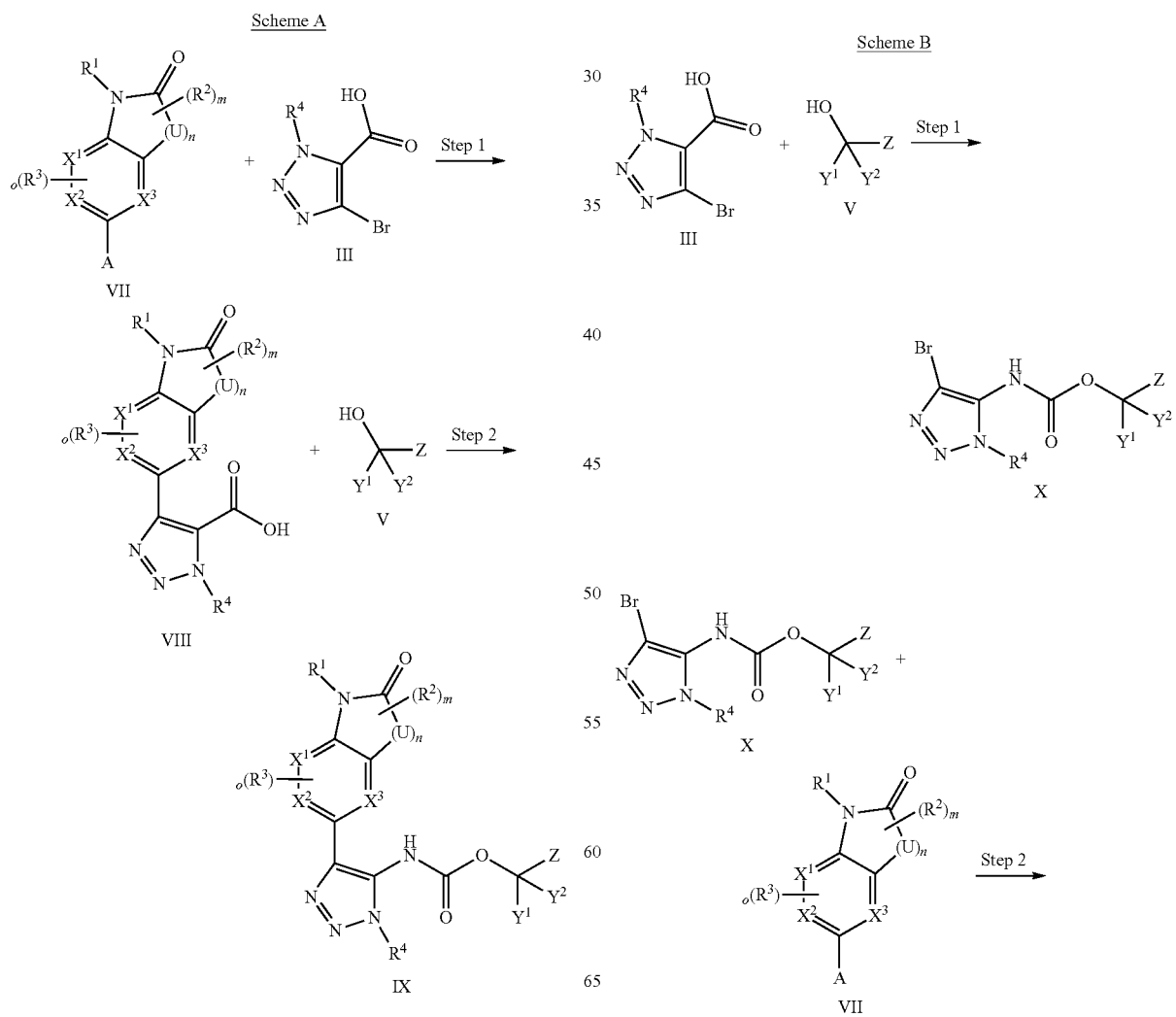

-continued

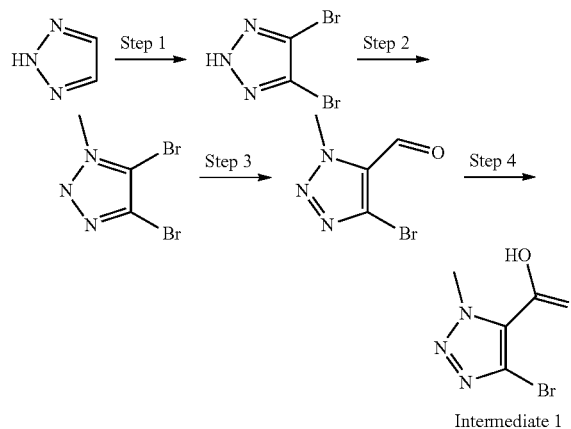

IX

Scheme B provides a general alternative synthesis of aryl, heteroaryl or bicyclic triazole carbamates (VI and IX). Step one describes a general synthesis of carbamate-containing bromo triazoles (X). A bromo triazole carboxylic acid (III) undergoes a Curtius rearrangement when reacted with diphenylphosphoryl azide (DPPA), or alternatively with 1-propanephosphonic anhydride (T3P) solution and azidotrimethylsilane. The intermediate isocyanate is then trapped with an alcohol (V) to provide the desired bromo triazole carbamate (X).

Step 2 describes a general synthesis for bicyclic triazole carbamate (IX) via cross coupling reaction. Bromo triazole carbamate (X) can first be converted to an organo-zinc species via lithium-halogen exchange and trapping with zinc chloride. Next, Negishi cross coupling with bicyclic halide (VII), provides the desired bicyclic triazole carbamate (IX). Alternatively, bicyclic halide (VII) can first be converted to the corresponding boronic ester such as pinacol boronate via Miyaura borylation, and then subjected to Suzuki reaction conditions with bromo triazole carbamate X to furnish the desired bicyclic triazole carbamate (IX).

Example 1: Preparation of 4-bromo-1-methyl-1H-1,2,3-triazole-5-carboxylic acid (Intermediate 1)

Step 1: 4,5-dibromo-2H-1,2,3-triazole

Bromine (2.8 mol) was added to a solution of 2H-1,2,3-triazole (1.4 mol) in water (600 mL) at 40° C. The resulting mixture was stirred for 2 hours at 40° C. After cooling to room temperature, the precipitate was collected by filtration. The solid was washed with water (2×300 mL) and dried under vacuum to give 4,5-dibromo-2H-1,2,3-triazole.

Step 2: 4,5-dibromo-1-methyl-1H-1,2,3-triazole

To a mixture of 4,5-dibromo-2H-1, 2, 3-triazole (704 mmol) and K$_2$CO$_3$ (1.4 mol) in THF (1000 mL), iodomethane (1.0 mol) was added. The mixture was stirred for 12 hours at room temperature. The mixture was filtered, and the filter cake was washed with ethyl acetate (2×500 mL), the filtrate was concentrated under 40° C. to afford a crude product, which was purified by column chromatography to give 4,5-dibromo-1-methyl-1H-1,2,3-triazole.

Step 3: 4-bromo-1-methyl-1H-1,2,3-triazole-5-carbaldehyde

To a solution of 4,5-dibromo-1-methyl-1H-1,2,3-triazole (168.0 mmol) in THF (600 mL) was added isopropylmagnesium chloride (252.0 mmol) at −10° C. The mixture was stirred for 15 min, DMF (840 mmol) was added. After 1 hour, the mixture was treated with 250 mL of saturated ammonium chloride and extracted with DCM (2×350 mL). The combined organics were washed with 250 mL of brine, dried over Na$_2$SO$_4$, filtered and concentrated to give 4-bromo-1-methyl-1H-1,2,3-triazole-5-carbaldehyde.

Step 4: 4-bromo-1-methyl-1H-1,2,3-triazole-5-carboxylic acid

Oxone (651 mmol) was added to a solution of 4-bromo-1-methyl-1H-1, 2, 3-triazole-5-carbaldehyde (536 mmol) in DMF (800 mL) and the resulting suspension was stirred at room temperature overnight. The mixture reaction was diluted with H$_2$O (1000 mL), was adjusted to pH 3 with 1N HCl, and the aqueous phase was extracted with ethyl acetate (3×800 mL). The combined organics were washed with saturated Na$_2$CO$_3$ (2×500 mL), the aqueous phase was adjusted to pH 3 with 1N HCl. The precipitate was isolated by filtration and dried under reduced pressure to provide 4-bromo-1-methyl-1H-1,2,3-triazole-5-carboxylic acid (Intermediate 1).

Example 2: Preparation of (R)-1-(2-chlorophenyl) ethyl (4-bromo-1-methyl-1H-1,2,3-triazol-5-yl)carbamate (Intermediate 2A)

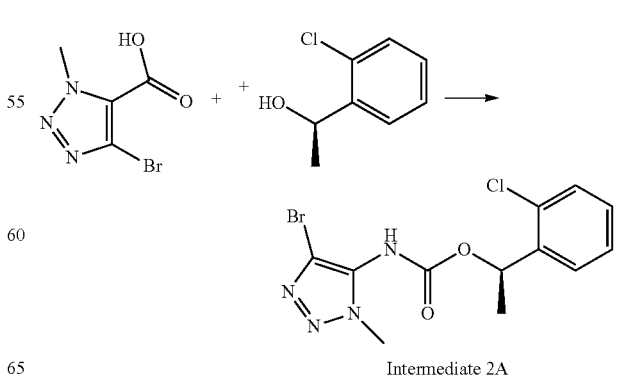

Intermediate 2A

To a suspension of 4-bromo-1-methyl-1H-1,2,3-triazole-5-carboxylic acid (24.3 mmol) in toluene (80 mL) was added DPPA (24.5 mmol), triethylamine (24.5 mmol), and (R)-1-(2-chlorophenyl)ethan-1-ol (36.5 mmol). The mixture was heated at 80° C. for 3 hours. The reaction mixture was filtered, and the filtrate was concentrated in vacuo. The residue was purified by silica chromatography to afford (R)-1-(2-chlorophenyl)ethyl (4-bromo-1-methyl-1H-1,2,3-triazol-5-yl)carbamate (Intermediate 2A).

Example 3: Preparation of (R)-1-(2-chloropyridin-3-yl)ethyl (4-bromo-1-methyl-1H-1,2,3-triazol-5-yl)carbamate (Intermediate 2B)

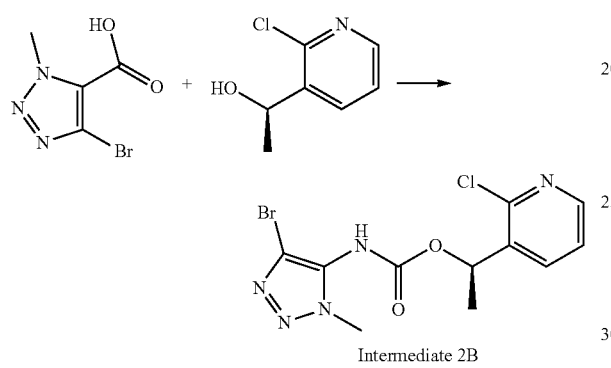

Intermediate 2B

4-Bromo-1-methyl-1H-1,2,3-triazole-5-carboxylic acid (95 mmol), 50% 1-propanephosphonic anhydride solution (143 mmol) in DMF, and azidotrimethylsilane (143 mmol), were suspended in THF (350 mL) under an atmosphere of argon. Triethylamine (143 mmol) was added and the resulting solution was allowed to stir for 30 minutes. (R)-1-(2-chloropyridin-3-yl)ethan-1-ol (143 mmol) was added and the mixture was heated at reflux, with a secondary bubbler attached to allow for venting, for 12 hours. The reaction mixture was cooled to room temperature, and the THF was removed in vacuo. The resulting crude material was dissolved in 500 mL ethyl acetate and extracted three times with 300 mL water. The crude mixture was then dried over sodium sulfate, filtered and the filtrate was concentrated. The crude was purified by silica gel column chromatography to provide (R)-1-(2-chloropyridin-3-yl)ethyl (4-bromo-1-methyl-1H-1,2,3-triazol-5-yl)carbamate (Intermediate 2B).

Example 4: Preparation of (R)-1-(2-fluoropyridin-3-yl)ethyl (4-bromo-1-methyl-1H-1,2,3-triazol-5-yl)carbamate (Intermediate 2C)

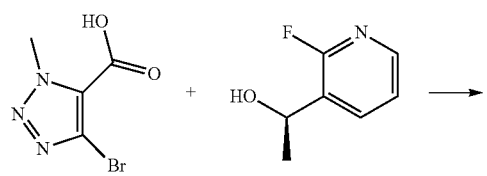

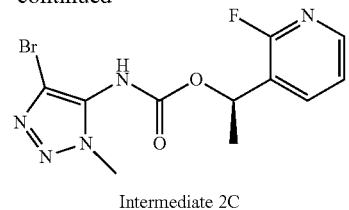

Intermediate 2C

Following the procedure described in Example 3 for the synthesis of (R)-1-(2-chloropyridin-3-yl)ethyl (4-bromo-1-methyl-1H-1,2,3-triazol-5-yl)carbamate (Intermediate 2B), using (R)-1-(2-fluoropyridin-3-yl)ethan-1-ol (143 mmol) in place of (R)-1-(2-chloropyridin-3-yl)ethan-1-ol, (R)-1-(2-fluoropyridin-3-yl)ethyl (4-bromo-1-methyl-1H-1,2,3-triazol-5-yl)carbamate was obtained (Intermediate 2C).

Example 5: Preparation of 1-methyl-4-(2-oxo-2,3-dihydro-1H-pyrido[2,3-b][1,4]oxazin-6-yl)-1H-1,2,3-triazole-5-carboxylic acid (Intermediate 4)

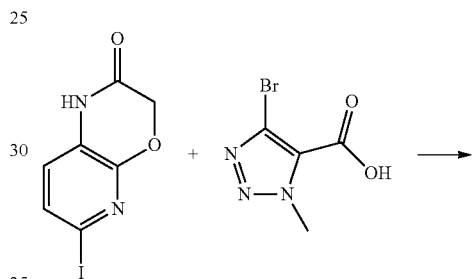

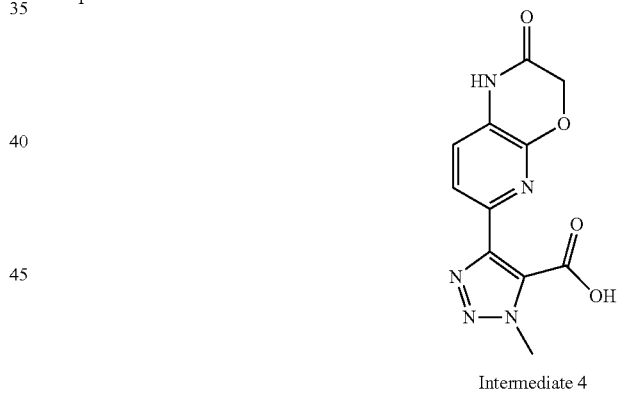

Intermediate 4

4-bromo-1-methyl-1H-1,2,3-triazole-5-carboxylic acid, Intermediate 1 (10.8 mmol) was dissolved in 98 mL of tetrahydrofuran and submerged in a −78° C. bath for 15 minutes. A 1 M solution of Lithium bis(trimethylsilyl)amide in tetrahydrofuran (11.7 mmol) was dropwise over 15 minutes. A 2.5 M solution of n-butyllithium (19.6 mmol) in hexanes was added dropwise over 20 minutes and allowed to stir for an additional 1 hour. A 1.9 M solution of zinc chloride (24.5 mmol) in 2-methyl tetrahydrofuran was added dropwise over 15 minutes. The reaction mixture was warmed to ambient temperature by submerging in a water bath and allowed to stir for 30 minutes. The resulting mixture was sparged with argon gas for 10 minutes, and then 6-iodo-1H-pyrido[2,3-b][1,4]oxazin-2-one (9.78 mmol) and [1,1′-Bis(diphenylphosphino)ferrocene]dichloropalladium (II), complex with dichloromethane (1 mmol) were added.

The reaction was heated at 70° C. for 1 hour, and then cooled to ambient temperature. The reaction was diluted with 100 mL of a 2 M aqueous solution of sodium hydroxide and 100 mL of diethyl ether. The aqueous layer was separated, and the organic layer was extract with a 2M aqueous solution of sodium hydroxide (50 mL). The combined aqueous layer was washed with a 1:1 mixture of ethyl acetate and diethyl ether (100 mL×2). 25 mL of concentrated hydrochloric acid was dropwise over 15 minutes under vigorous stirring to adjust pH to 4. The mixture was filtered, and the filter cake was washed with water (50 mL) and a 1:1 mixture of ethyl acetate and diethyl ether (50 mL×2). The precipitate was dried under reduced pressure to provide 1-methyl-4-(2-oxo-2,3-dihydro-1H-pyrido[2,3-b][1,4]oxazin-6-yl)-1H-1,2,3-triazole-5-carboxylic acid (Intermediate 4).

Example 6: Alternative Preparation of 1-methyl-4-(2-oxo-2,3-dihydro-1H-pyrido[2,3-b][1,4]oxazin-6-yl)-1H-1,2,3-triazole-5-carboxylic acid (Intermediate 4)

To a mixture of 4-bromo-1-methyl-1H-1,2,3-triazole-5-carboxylic acid, Intermediate 1 (2.17 mmol) in tetrahydrofuran (14.5 mL) at −78° C. was added a 1 M solution of lithium bis(trimethylsilyl)amide (2.17 mmol) in tetahydrofuran. After 10 minutes, a 2.5 M solution of n-butyllithium (4.35 mmol) in hexanes was added. After 45 minutes, a 1.9 M solution of zinc chloride (6.52 mmol) in 2-methyltetrahydrofuran was added, and the reaction was stirred at room temperature for 45 minutes. At this point 6-iodo-1H-pyrido[2,3-b][1,4]oxazin-2-one (1.45 mmol) and [1,1'-bis(diphenylphosphino)ferrocene]dichloropalladium(II) complex with dichloromethane (0.145 mmol) were added to the reaction and the reaction mixture was heated to 70° C. for 1 hour. After completion of the reaction, the mixture was cooled and quenched with acetic acid. The mixture was concentrated under reduced pressure and purified by column chromatography to provide 1-methyl-4-(2-oxo-2,3-dihydro-1H-pyrido[2,3-b][1,4]oxazin-6-yl)-1H-1,2,3-triazole-5-carboxylic acid (Intermediate 4).

Example 7: Preparation of 1-(2-chloro-6-fluoropyridin-3-yl)ethan-1-ol

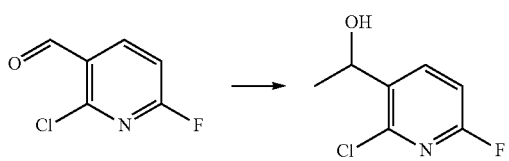

2-Chloro-6-fluoronicotinaldehyde (2.51 mmol) dissolved in methyl tetrahydrofuran (20 mL) was cooled in an ice/acetonitrile bath and then methylmagnesium bromide solution (3.0 M, 7.20 mmol) was added dropwise. The reaction mixture was quenched with addition of ethanol, and then diluted with ethyl acetate and washed with 10% citric acid. The organic layer was concentrated. The residue was purified by column chromatography to give 1-(2-chloro-6-fluoropyridin-3-yl)ethan-1-ol.

Example 8: Preparation of 1-(2-fluoro-5-methylpyridin-4-yl)ethan-1-ol

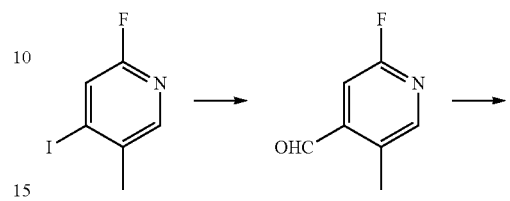

A solution of 2-fluoro-4-iodo-5-methylpyridine (4.22 mmol) in 20 mL THF was cooled to 0° C. and treated with 1.6 M nBuLi in hexanes (5.06 mmol). After 15 min DMF (12.7 mmol) was added dropwise. The reaction was stirred for 30 min, then warmed to room temperature and quenched with sat NH₄Cl. The mixture was extracted with EtOAc, dried with MgSO₄ and concentrated to provide 2-fluoro-5-methylisonicotinaldehyde. 2-fluoro-5-methylisonicotinaldehyde (5.5 mmol) was taken up in 25 mL THF and cooled to −15° C. in an ice-acetone bath. Treated with 3 M MeMgBr in THF (11.2 mmol) and stirred for 20 minutes. Quenched with sat NH₄Cl and extracted with EtOAc, dried with MgSO₄, filtered and concentrated to provide 1-(2-fluoro-5-methylpyridin-4-yl)ethan-1-ol (MS (m/z) 155.9 [M+H]+).

Example 9: Preparation of 1-(2,5-difluoropyridin-4-yl)ethan-1-ol

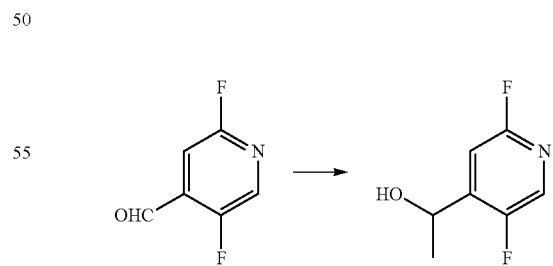

Following the procedure described in Example 8 for the synthesis of 1-(2-fluoro-5-methylpyridin-4-yl)ethan-1-ol, using 2,5-difluoroisonicotinaldehyde (11.9 mmol) in place of 2-fluoro-5-methylisonicotinaldehyde, 1-(2,5-difluoropyridin-4-yl)ethan-1-ol was obtained. (MS (m/z) 160.11[M+H]+)

Example 10: Preparation of 1-(5-bromo-2-fluoropyridin-3-yl)ethan-1-ol

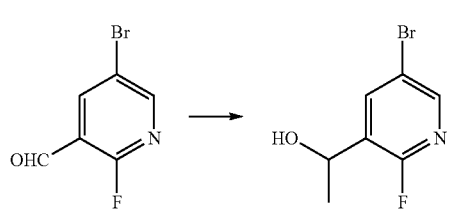

Following the procedure described in Example 8 for the synthesis of 1-(2-fluoro-5-methylpyridin-4-yl)ethan-1-ol, using 5-bromo-2-fluoronicotinaldehyde (7.35 mmol) in place of 2-fluoro-5-methylisonicotinaldehyde, 1-(5-bromo-2-fluoropyridin-3-yl)ethan-1-ol was obtained. (MS (m/z) 220.01[M+H]+)

Example 11: Preparation of 1-(5-bromo-2-chloropyridin-3-yl)ethan-1-ol

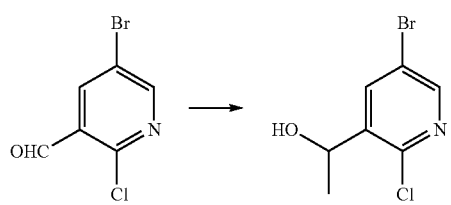

Following the procedure described in Example 8 for the synthesis of 1-(2-fluoro-5-methylpyridin-4-yl)ethan-1-ol, using 5-bromo-2-chloronicotinaldehyde (10.6 mmol) in place of 2-fluoro-5-methylisonicotinaldehyde, 1-(5-bromo-2-chloropyridin-3-yl)ethan-1-ol was obtained. (MS (m/z) 235.99[M+H]+)

Example 12: Preparation of 1-(2,5-difluoropyridin-4-yl)ethan-1-ol

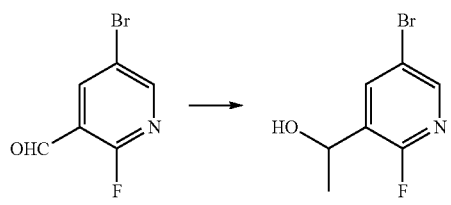

Following the procedure described in Example 8 for the synthesis of 1-(2-fluoro-5-methylpyridin-4-yl)ethan-1-ol, using 5-bromo-2-fluoronicotinaldehyde (7.4 mmol) in place of 2-fluoro-5-methylisonicotinaldehyde, 1-(5-bromo-2-fluoropyridin-3-yl)ethan-1-ol. (MS (m/z) 220.01[M+H]+)

Example 13: Preparation of Compounds 1 to 5

Compounds 1 to 5 were generally synthesized according Scheme A, Step 2. For example, (R)-1-(2-chloro-5-fluoropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate (Compound 1) was prepared as follows.

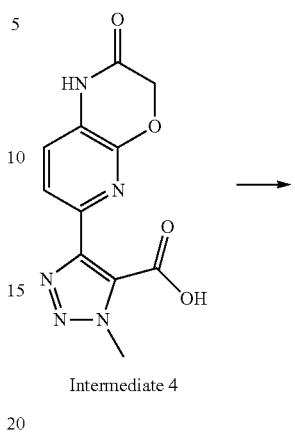

Intermediate 4

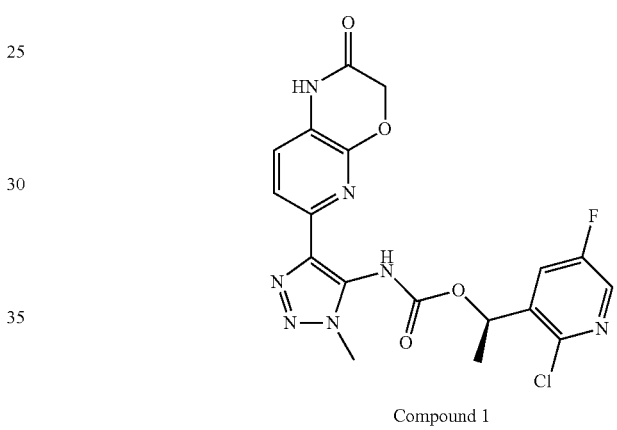

Compound 1

To a mixture of 1-methyl-4-(2-oxo-2,3-dihydro-1H-pyrido[2,3-b][1,4]oxazin-6-yl)-1H-1,2,3-triazole-5-carboxylic acid, (Intermediate 4) (0.247 mmol), 1-propanephosphonic acid cyclic anhydride (50% in DMF, 0.371 mmol), and azidotrimethysilane (0.371 mmol) acid in THF (1.24 mL) was added triethylamine (0.494 mmol) dropwise. (1R)-1-(2-chloro-5-fluoro-3-pyridyl)ethanol (0.333 mmol) was added and the reaction was heated at 70° C. for 1 hour. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide (R)-1-(2-chloro-5-fluoropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate (Compound 1). (MS (m/z) 448.1 [M+H]+). $^1$H NMR (400 MHz, Methanol-$d_4$) δ 8.27 (s, 1H), 7.95 (dd, J=9.0, 3.2 Hz, 1H), 7.64 (d, J=8.0 Hz, 1H), 7.32 (s, 1H), 6.05 (q, J=6.5 Hz, 1H), 4.82 (s, 2H), 3.99 (s, 3H), 1.64 (s, 3H).

Compounds 2-5 (Table 1) were similarly prepared according to Scheme A, Step 2 by reacting Intermediate 4 (Example 5 or 6) with the Reagent listed in Table 1 in place of (1R)-1-(2-chloro-5-fluoro-3-pyridyl)ethanol following the general process described for Compound 1.

TABLE 1

Compounds prepared according to Scheme A, Step 2.

| Name | Structure | Reagent | LCMS m/z | NMR |
|---|---|---|---|---|
| Compound 2 1-(2,5-difluoropyridin-4-yl)ethyl(1-methyl-4-(2-oxo-2,3-dihydro-1H-pyrido[2,3-b][1,4]-oxazin-6-yl)-1H-1,2,3-triazol-5-yl)carbamate | 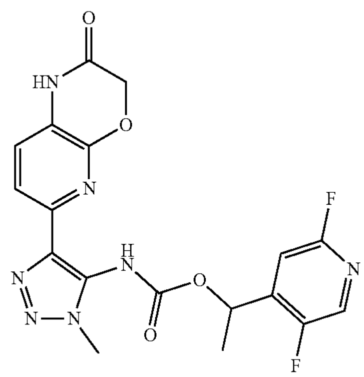 [SMILES: CC(OC(=O)Nc1c(-c2ccc3c(n2)OCC(=O)N3)nnn1C)c1cc(F)ncc1F] | | 432.1 | 1H NMR (400 MHz, Acetonitrile-d3) δ 8.77 (s, 1H), 8.26 (t, J = 1.9 Hz, 1H), 7.71 (d, J = 8.0 Hz, 1H), 7.56 (dd, J = 5.3, 2.9 Hz, 1H), 7.32 (d, J = 8.0 Hz, 1H), 5.99 (q, J = 6.7 Hz, 1H), 5.69 (dt, J = 9.5, 6.5 Hz, 1H), 4.77 (s, 2H), 3.94 (s, 3H), 1.58-1.55 (m, 3H). |
| Compound 3 (R)-1-(2,5-difluoropyridin-3-yl)ethyl(1-methyl-4-(2-oxo-2,3-dihydro-1H-pyrido[2,3-b][1,4]oxazin-6-yl)-1H-1,2,3-triazol-5-yl)carbamate | | | 432.0 | 1H NMR (400 MHz, Methanol-d4) δ 8.02 (d, 2H), 7.60 (d, J = 8.0 Hz, 1H), 7.29 (d, J = 8.0 Hz, 1H), 5.95 (q, J = 6.7 Hz, 1H), 4.80 (s, 2H), 3.96 (s, 3H), 1.62 (s, 3H). |
| Compound 4 (R)-1-(5-chloro-2-fluoropyridin-3-yl)-ethyl(1-methyl-4-(2-oxo-2,3-dihydro-1H-pyrido[2,3-b][1,4]-oxazin-6-yl)-1H-1,2,3-triazol-5-yl)-carbamate | 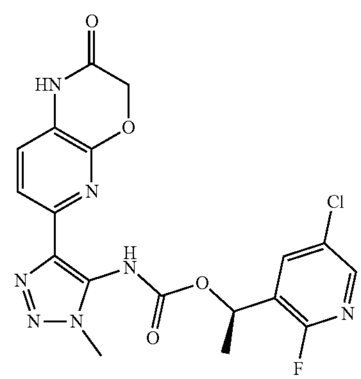 [SMILES: C[C@@H](OC(=O)Nc1c(-c2ccc3c(n2)OCC(=O)N3)nnn1C)c1cc(Cl)cnc1F] | | 448.1 | 1H NMR (400 MHz, Methanol-d4) δ 8.13 (s, 2H), 7.60 (d, J = 8.0 Hz, 1H), 7.29 (d, J = 7.6 Hz, 1H), 5.95 (q, J = 6.6 Hz, 1H), 4.79 (s, 2H), 4.58 (s, 1H), 3.96 (s, 3H), 1.45 (d, J = 129.2 Hz, 3H). |
| Compound 5 (S)-2-fluoro-1-phenylethyl (1-methyl-4-(2-oxo-2,3-dihydro-1H-pyrido[2,3-b][1,4]-oxazin-6-yl)-1H-1,2,3-triazol-5-yl)-carbamate | 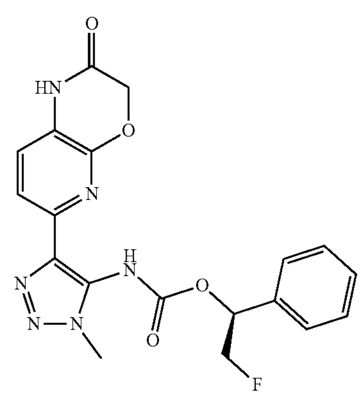 [SMILES: Cn1nnc(-c2ccc3c(n2)OCC(=O)N3)c1NC(=O)O[C@H](CF)c1ccccc1] | | 431.1 | 1H NMR (400 MHz, Methanol-d4) δ 7.56 (d, J = 8.0 Hz, 1H), 7.49-7.23 (m, 6H), 5.98 (dt, J = 16.9, 5.3 Hz, 1H), 4.79 (s, 2H), 4.72-4.49 (m, 2H), 3.94 (s, 3H). |

Example 14: Preparation of [(R)-1-(2-chloro-3-pyridyl)ethyl] N-[5-(7-fluoro-2-oxo-3,4-dihydro-1H-quinolin-6-yl)-3-methyl-triazol-4-yl]carbamate (Compound 6)

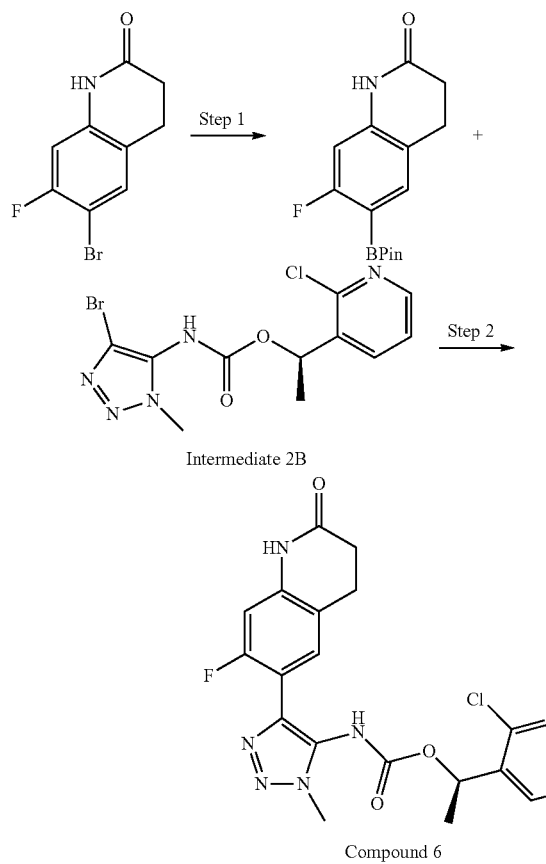

Step 1: 7-fluoro-6-(4,4,5,5-tetramethyl-1,3,2-dioxaborolan-2-yl)-3,4-dihydro-1H-quinolin-2-one A mixture of 6-bromo-7-fluoro-3,4-dihydro-1H-quinolin-2-one (1.23 mmol), 1,1'-Bis(diphenylphosphino)ferrocene-palladium(II)dichloride dichloromethane complex (0.123 mmol), Bis(pinacolato)diboron (1.84 mmol), and potassium acetate (1.84 mmol) in 1,4-dioxane (12 mL) was heated to 100° C. for 4 hours. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by column chromatography to provide 7-fluoro-6-(4,4,5,5-tetramethyl-1,3,2-dioxaborolan-2-yl)-3,4-dihydro-1H-quinolin-2-one.

Step 2: [(1R)-1-(2-chloro-3-pyridyl)ethyl] N-[5-(7-fluoro-2-oxo-3,4-dihydro-1H-quinolin-6-yl)-3-methyl-triazol-4-yl]carbamate (Compound 6)

A mixture of 7-fluoro-6-(4,4,5,5-tetramethyl-1,3,2-dioxaborolan-2-yl)-3,4-dihydro-1H-quinolin-2-one (0.211 mmol), (R)-1-(2-chloropyridin-3-yl)ethyl (4-bromo-1-methyl-1H-1,2,3-triazol-5-yl)carbamate (Intermediate 2B) (0.222 mmol), and potassium carbonate (0.444 mmol) in 3:1 1,4-dioxane/water (3 mL) was heated to 80° C. for 30 minutes. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide [(1R)-1-(2-chloro-3-pyridyl)ethyl] N-[5-(7-fluoro-2-oxo-3,4-dihydro-1H-quinolin-6-yl)-3-methyl-triazol-4-yl]carbamate (Compound 6). (MS (m/z) 445.1 [M+H]$^+$). $^1$H NMR (400 MHz, Methanol-d$_4$) δ 8.33 (s, 1H), 8.00 (s, 1H), 7.42 (d, J=7.6 Hz, 2H), 6.67 (d, J=11.2 Hz, 1H), 6.04 (s, 1H), 3.95 (s, 3H), 2.95 (t, J=7.6 Hz, 2H), 2.60 (dd, J=8.5, 6.6 Hz, 2H), 1.60 (s, 3H).

Example 15: Preparation of (R)-1-(2-chloropyridin-3-yl)ethyl (4-(5-fluoro-2-oxo-1,2,3,4-tetrahydroquinolin-6-yl)-1-methyl-1H-1,2,3-triazol-5-yl)carbamate (Compound 7)

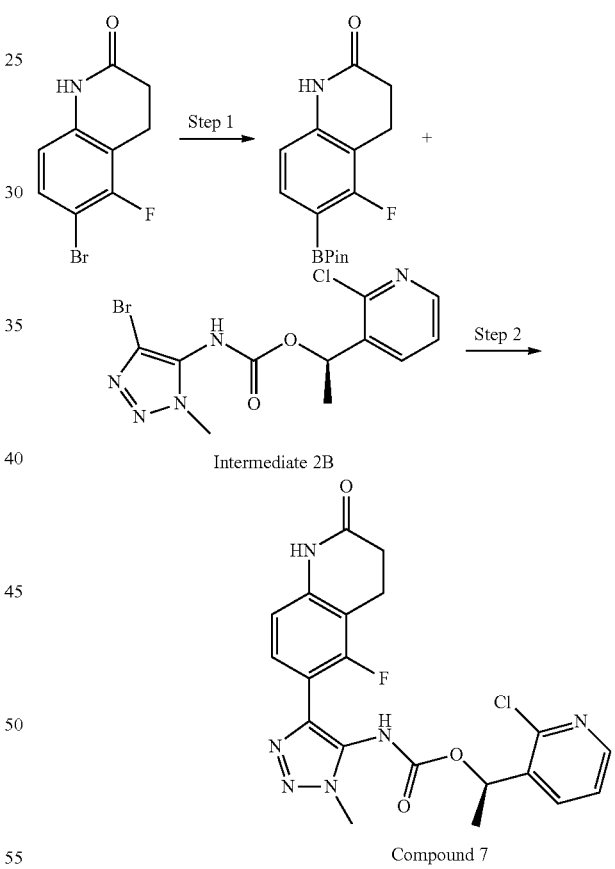

Following the synthesis described in Example 14 for [(1R)-1-(2-chloro-3-pyridyl)ethyl] N-[5-(7-fluoro-2-oxo-3,4-dihydro-1H-quinolin-6-yl)-3-methyl-triazol-4-yl]carbamate in step 1, 6-bromo-5-fluoro-3,4-dihydroquinolin-2(1H)-one (1.23 mmol) instead of 6-bromo-7-fluoro-3,4-dihydro-1H-quinolin-2-one, (R)-1-(2-chloropyridin-3-yl)ethyl (4-(5-fluoro-2-oxo-1,2,3,4-tetrahydroquinolin-6-yl)-1-methyl-1H-1,2,3-triazol-5-yl)carbamate (Compound 7) was obtained. (MS (m/z) 445.1 [M+H]$^+$). $^1$H NMR (400 MHz, Methanol-d$_4$) δ 8.36 (s, 1H), 8.03 (s, 1H), 7.44 (q, J=11.0, 7.9 Hz, 2H), 6.78 (d, J=8.4 Hz, 1H), 6.09 (s, 1H), 3.98 (s, 3H), 2.99 (q, J=7.3 Hz, 2H), 2.63 (t, J=7.8 Hz, 2H), 1.63 (s, 3H).

Example 16: Preparation of: (R)-1-(2-chloropyridin-3-yl)ethyl (1-methyl-4-(3-oxo-3,4-dihydro-2H-pyrido[3,2-b][1,4]oxazin-7-yl)-1H-1,2,3-triazol-5-yl)carbamate (Compound 8)

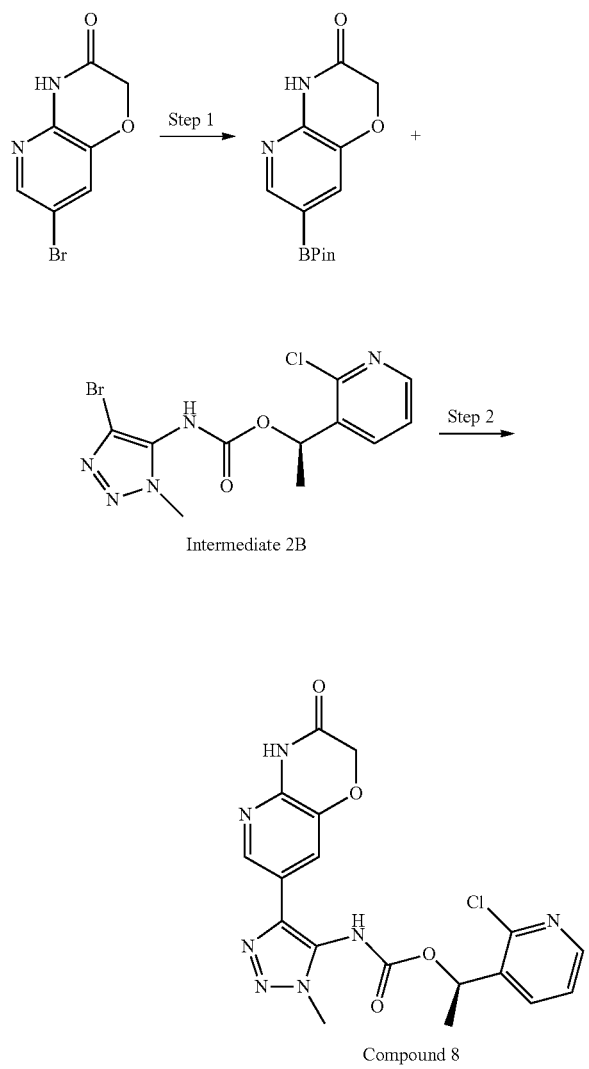

Compound 8

Following the synthesis described in Example 14 for [(1R)-1-(2-chloro-3-pyridyl)ethyl] N-[5-(7-fluoro-2-oxo-3,4-dihydro-1H-quinolin-6-yl)-3-methyl-triazol-4-yl]carbamate in step 1, using 7-bromo-4H-pyrido[3,2-b][1,4]oxazin-3-one (1.31 mmol) instead of 6-bromo-7-fluoro-3,4-dihydro-1H-quinolin-2-one, (R)-1-(2-chloropyridin-3-yl)ethyl (1-methyl-4-(3-oxo-3,4-dihydro-2H-pyrido[3,2-b][1,4]oxazin-7-yl)-1H-1,2,3-triazol-5-yl)carbamate (Compound 8) was obtained. (MS (m/z) 430.1 [M+H]+). $^1$H NMR (400 MHz, Methanol-$d_4$) δ 8.33 (s, 1H), 8.25 (d, J=1.9 Hz, 1H), 8.04 (s, 1H), 7.59 (d, J=1.9 Hz, 1H), 7.49 (s, 1H), 6.09 (q, J=6.6 Hz, 1H), 4.70 (s, 2H), 3.94 (s, 3H), 1.63 (s, 3H).

Example 17. Preparation of (R)-1-(2-fluoropyridin-3-yl)ethyl (4-(4,4-dimethyl-2-oxo-1,4-dihydro-2H-benzo[d][1,3]oxazin-6-yl)-1-methyl-1H-1,2,3-triazol-5-yl)carbamate (Compound 9)

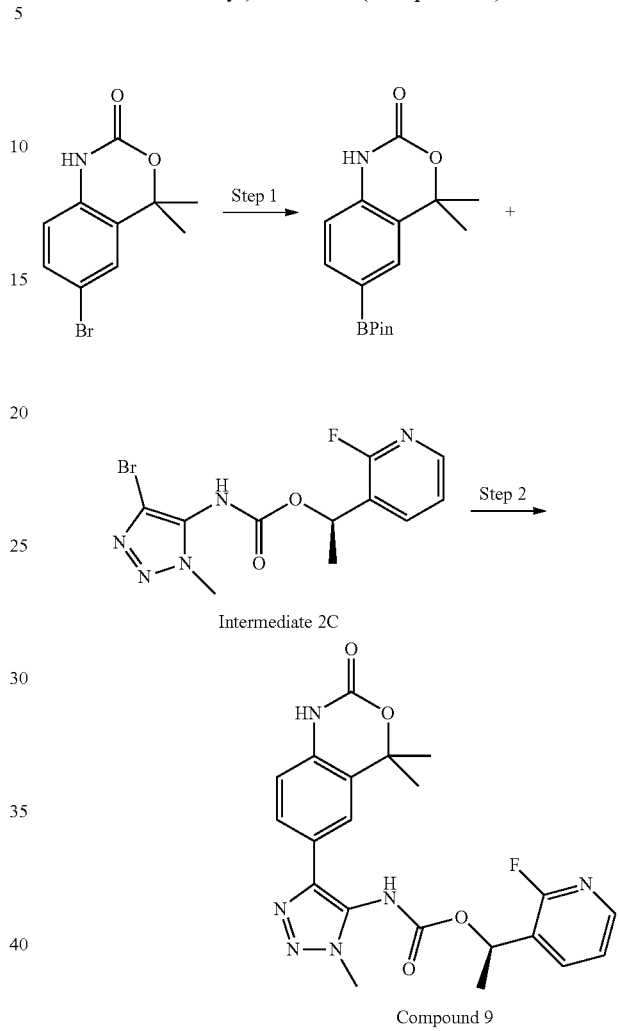

Compound 9

Following the synthesis described in Example 14 for 7-fluoro-6-(4,4,5,5-tetramethyl-1,3,2-dioxaborolan-2-yl)-3,4-dihydro-1H-quinolin-2-one, in step 1 using 6-bromo-4,4-dimethyl-1H-3,1-benzoxazin-2-one (1.17 mmol) instead of 6-bromo-7-fluoro-3,4-dihydro-1H-quinolin-2-one, 4,4-dimethyl-6-(4,4,5,5-tetramethyl-1,3,2-dioxaborolan-2-yl)-1H-3,1-benzoxazin-2-one was obtained.

Following the synthesis described in Example 14 for [(1R)-1-(2-chloro-3-pyridyl)ethyl] N-[5-(7-fluoro-2-oxo-3,4-dihydro-1H-quinolin-6-yl)-3-methyl-triazol-4-yl]carbamate, in step 2 using (R)-1-(2-fluoropyridin-3-yl)ethyl (4-bromo-1-methyl-1H-1,2,3-triazol-5-yl)carbamate (Intermediate 2C) in place of (R)-1-(2-chloropyridin-3-yl)ethyl (4-bromo-1-methyl-1H-1,2,3-triazol-5-yl)carbamate (Intermediate 2B), (R)-1-(2-fluoropyridin-3-yl)ethyl (4-(4,4-dimethyl-2-oxo-1,4-dihydro-2H-benzo[d][1,3]oxazin-6-yl)-1-methyl-1H-1,2,3-triazol-5-yl)carbamate (Compound 9) was obtained. (MS (m/z) 441.1 [M+H]+). $^1$H NMR (400 MHz, Methanol-$d_4$) δ 8.18 (s, 1H), 8.05 (s, 1H), 7.59 (d, J=15.0 Hz, 2H), 7.37 (s, 1H), 6.93 (d, J=8.3 Hz, 1H), 6.02 (s, 1H), 3.94 (s, 3H), 1.67 (s, 9H).

Example 18: Preparation of (R)-1-(2-chloropyridin-3-yl)ethyl (1-methyl-4-(2-oxo-2,3,4,5-tetrahydro-1H-benzo[b]azepin-7-yl)-1H-1,2,3-triazol-5-yl)carbamate (Compound 10)

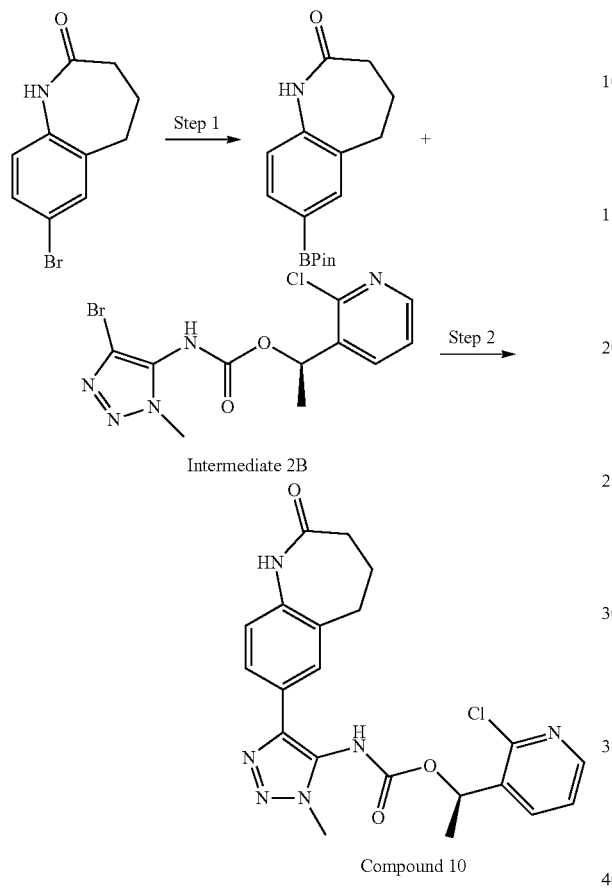

Compound 10

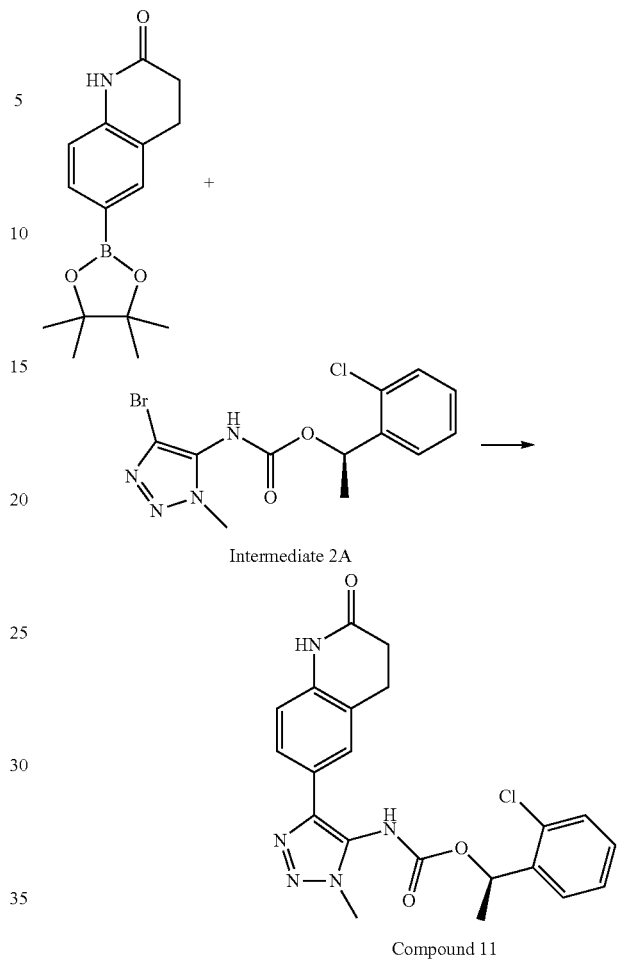

Compound 11

Following the synthesis described in Example 14 for 7-fluoro-6-(4,4,5,5-tetramethyl-1,3,2-dioxaborolan-2-yl)-3,4-dihydro-1H-quinolin-2-one, in step 1 using 7-bromo-1,3,4,5-tetrahydro-1-benzazepin-2-one (0.833 mmol) instead of 6-bromo-7-fluoro-3,4-dihydro-1H-quinolin-2-one, 7-(4,4,5,5-tetramethyl-1,3,2-dioxaborolan-2-yl)-1,3,4,5-tetrahydro-1-benzazepin-2-one was obtained.

Following the synthesis described in Example 14 for [(1R)-1-(2-chloro-3-pyridyl)ethyl] N-[5-(7-fluoro-2-oxo-3,4-dihydro-1H-quinolin-6-yl)-3-methyl-triazol-4-yl]carbamate, in step 2 using sodium carbonate (0.416 mmol) instead of potassium carbonate, (R)-1-(2-chloropyridin-3-yl)ethyl (1-methyl-4-(2-oxo-2,3,4,5-tetrahydro-1H-benzo[b]azepin-7-yl)-1H-1,2,3-triazol-5-yl)carbamate (Compound 10) was obtained. (MS (m/z) 441.2 [M+H]+). 1H NMR (400 MHz, Methanol-d4) δ 8.36 (s, 1H), 8.07 (s, 1H), 7.67-7.58 (m, 2H), 7.49 (s, 1H), 7.09 (d, J=8.3 Hz, 1H), 6.13 (s, 1H), 3.96 (s, 3H), 2.82 (t, J=7.0 Hz, 2H), 2.32 (d, J=6.7 Hz, 2H), 2.27 (q, J=7.0 Hz, 2H), 1.67 (s, 3H).

Example 19: Preparation of Compounds 11 to 20

Compounds 11 to 20 were generally synthesized according Scheme B, Step 2. For example, (R)-1-(2-chlorophenyl)ethyl (1-methyl-4-(2-oxo-1,2,3,4-tetrahydroquinolin-6-yl)-1H-1,2,3-triazol-5-yl)carbamate (Compound 11) was prepared as follows.

A mixture of 6-(4,4,5,5-tetramethyl-1,3,2-dioxaborolan-2-yl)-3,4-dihydro-1H-quinolin-2-one (1.67 mmol), (R)-1-(2-chlorophenyl)ethyl (4-bromo-1-methyl-1H-1,2,3-triazol-5-yl)carbamate (Intermediate 2A) (0.556 mmol), and sodium carbonate (1.67 mmol) in 3:1 1,4-dioxane/water (7 mL) was heated to 100° C. for 1 hour. The mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide (R)-1-(2-chlorophenyl)ethyl (1-methyl-4-(2-oxo-1,2,3,4-tetrahydroquinolin-6-yl)-1H-1,2,3-triazol-5-yl)carbamate (Compound 11). (MS (m/z) 426.1 [M+H]+). 1H NMR (400 MHz, Methanol-d4) δ 7.61 (s, 1H), 7.54 (d, J=1.7 Hz, 1H), 7.51 (d, J=8.4 Hz, 1H), 7.36 (d, J=33.0 Hz, 3H), 6.91 (d, J=8.2 Hz, 1H), 6.19 (s, 1H), 3.92 (s, 3H), 2.95 (t, J=7.6 Hz, 2H), 2.58 (t, J=7.6 Hz, 2H), 1.61 (s, 3H).

Compounds 12-15 (Table 2) were similarly prepared according to Scheme B, Step 2 by reacting (R)-1-(2-chlorophenyl)ethyl (4-bromo-1-methyl-1H-1,2,3-triazol-5-yl)carbamate (Intermediate 2A) (Example 2) with the Reagent listed in Table 2 in place of 6-(4,4,5,5-tetramethyl-1,3,2-dioxaborolan-2-yl)-3,4-dihydro-1H-quinolin-2-one following the general process described for Compound 11.

Compounds 16-18 (Table 2) were similarly prepared according to Scheme B, Step 2 by reacting (R)-1-(2-chloropyridin-3-yl)ethyl (4-bromo-1-methyl-1H-1,2,3-triazol-5- yl)carbamate (Intermediate 2B) (Example 3) with the Reagent listed in Table 2 in place of 6-(4,4,5,5-tetramethyl-1,3,2-dioxaborolan-2-yl)-3,4-dihydro-1H-quinolin-2-one following the general process described for Compound 11.

TABLE 2

Compounds prepared according to Scheme B, Step 2.

| Compound No. | Structure | Reagent | LCMS m/z | 1H NMR |
|---|---|---|---|---|
| Compound 11 (R)-1-(2-chlorophenyl)ethyl(1-methyl-4-(2-oxo-1,2,3,4-tetrahydroquinolin-6-yl)-1H-1,2,3-triazol-5-yl)-carbamate | 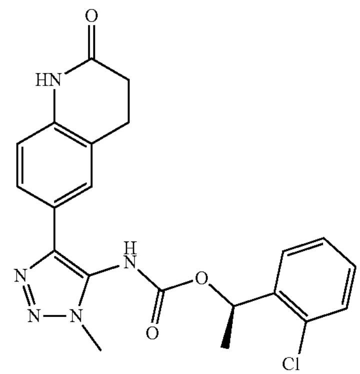 [SMILES: C[C@@H](OC(=O)Nc1c(-c2ccc3c(c2)CCC(=O)N3)nnn1C)c1ccccc1Cl] | | 426.1 | 1H NMR (400 MHz, Methanol-d4) δ 7.61 (s, 1H), 7.54 (d, J = 1.7 Hz, 1H), 7.51 (d, J = 8.4 Hz, 1H), 7.36 (d, J = 33.0 Hz, 3H), 6.91 (d, J = 8.2 Hz, 1H), 6.19 (s, 1H), 3.92 (s, 3H), 2.95 (t, J = 7.6 Hz, 2H), 2.58 (t, J = 7.6 Hz, 2H), 1.61 (s, 3H). |
| Compound 12 (R)-1-(2-chlorophenyl)ethyl(1-methyl-4-(2-oxo-1,4-dihydro-2H-benzo[d][1,3]-oxazin-6-yl)-1H-1,2,3-triazol-5-yl)-carbamate | 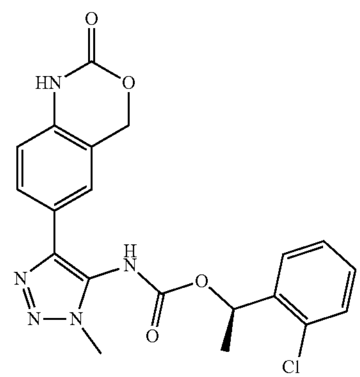 [SMILES: C[C@@H](OC(=O)Nc1c(-c2ccc3c(c2)COC(=O)N3)nnn1C)c1ccccc1Cl] | | 428.1 | 1H NMR (400 MHz, Methanol-d4) δ 7.60 (d, J = 8.8 Hz, 2H), 7.52 (d, J = 1.8 Hz, 1H), 7.49-7.20 (m, 3H), 6.92 (d, J = 8.3 Hz, 1H), 6.19 (d, J = 13.0 Hz, 1H), 5.31 (s, 2H), 3.92 (s, 3H), 1.59 (d, J = 6.6 Hz, 3H). |
| Compound 13 (R)-1-(2-chlorophenyl)ethyl(1-methyl-4-(3-oxo-3,4-dihydro-2H-benzo[b][1,4]-oxazin-7-yl)-1H-1,2,3-triazol-5-yl)-carbamate | 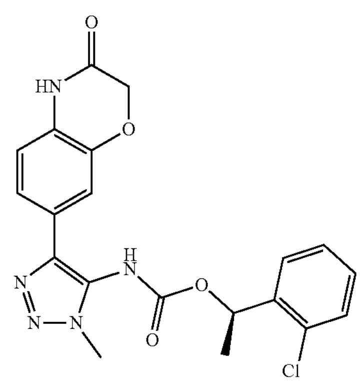 [SMILES: C[C@@H](OC(=O)Nc1c(-c2ccc3c(c2)OCC(=O)N3)nnn1C)c1ccccc1Cl] | | 428.1 | 1H NMR (400 MHz, Methanol-d4) δ 7.62 (s, 1H), 7.49-7.22 (m, 5H), 6.93 (d, J = 8.6 Hz, 1H), 6.17 (s, 1H), 4.61 (s, 2H), 3.92 (d, J = 6.8 Hz, 3H), 1.61 (s, 3H). |
| Compound 14 (R)-1-(2-chlorophenyl)ethyl(1-methyl-4-(2-oxoindolin-5-yl)-1H-1,2,3-triazol-5-yl)carbamate | 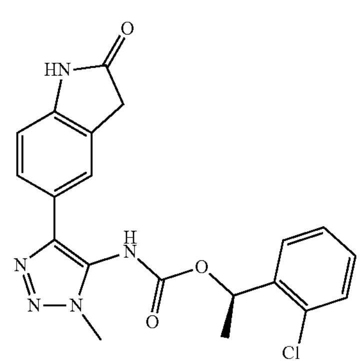 [SMILES: C[C@@H](OC(=O)Nc1c(-c2ccc3c(c2)CC(=O)N3)nnn1C)c1ccccc1Cl] | | 412.1 | 1H NMR (400 MHz, Methanol-d4) δ 7.71-7.50 (m, 3H), 7.37 (d, J = 31.5 Hz, 3H), 6.93 (d, J = 8.1 Hz, 1H), 6.18 (s, 1H), 3.91 (s, 3H), 3.54 (s, 2H), 1.70-1.20 (m, 3H). |

TABLE 2-continued

Compounds prepared according to Scheme B, Step 2.

| Compound No. | Structure | Reagent | LCMS m/z | 1H NMR |
|---|---|---|---|---|
| Compound 15 (R)-1-(2-chlorophenyl)ethyl(1-methyl-4-(2-oxo-1,2-dihydroquinolin-6-yl)-1H-1,2,3-triazol-5-yl)carbamate | 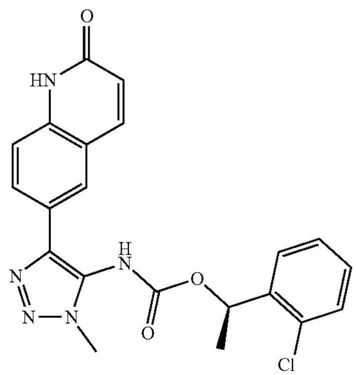 [SMILES: C[C@@H](OC(=O)Nc1c(-c2ccc3[nH]c(=O)ccc3c2)nnn1C)c1ccccc1Cl] | | 424.1 | 1H NMR (400 MHz, Methanol-d4) δ 7.98 (d, J = 1.9 Hz, 1H), 7.94-7.85 (m, 2H), 7.61 (s, 1H), 7.47-7.19 (m, 4H), 6.65 (d, J = 9.5 Hz, 1H), 6.19 (s, 1H), 3.95 (s, 3H), 1.62 (s, 3H). |
| Compound 16 (R)-1-(2-chloropyridin-3-yl)ethyl (1-methyl-4-(2-oxo-1,4-dihydro-2H-benzo[d][1,3]-oxazin-6-yl)-1H-1,2,3-triazol-5-yl)-carbamate | 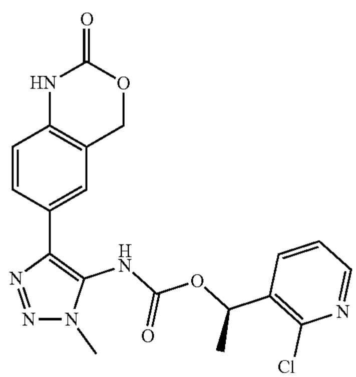 [SMILES: C[C@@H](OC(=O)Nc1c(-c2ccc3c(c2)COC(=O)N3)nnn1C)c1cccnc1Cl] | | 429.1 | 1H NMR (400 MHz, Methanol-d4) δ 8.35 (s, 1H), 8.04 (s, 1H), 7.59 (d, J = 8.3 Hz, 1H), 7.54 (d, J = 1.8 Hz, 1H), 7.48 (s, 1H), 6.93 (d, J = 8.2 Hz, 1H), 6.09 (s, 1H), 5.33 (s, 2H), 3.93 (s, 3H), 1.65 (s, 3H). |
| Compound 17 (R)-1-(2-chloropyridin-3-yl)ethyl (1-methyl-4-(2-oxo-1,2,3,4-tetrahydroquinolin-6-yl)-1H-1,2,3-triazol-5-yl)-carbamate | 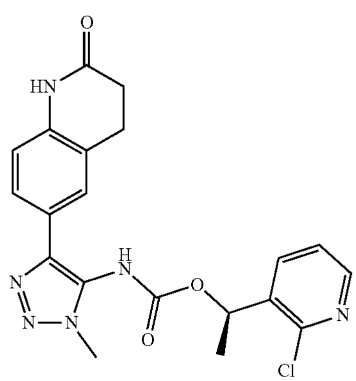 [SMILES: C[C@@H](OC(=O)Nc1c(-c2ccc3c(c2)CCC(=O)N3)nnn1C)c1cccnc1Cl] | | 427.1 | 1H NMR (400 MHz, Methanol-d4) δ 8.35 (s, 1H), 8.05 (s, 1H), 7.55 (s, 1H), 7.51 (d, J = 8.1 Hz, 1H), 7.21 (s, 1H), 6.91 (d, J = 8.3 Hz, 1H), 6.11 (s, 1H), 3.92 (s, 3H), 2.97 (t, J = 7.6 Hz, 2H), 2.66-2.51 (m, 2H), 1.65 (s, 3H). |
| Compound 18 (R)-1-(2-chloropyridin-3-yl)ethyl (1-methyl-4-(3-oxo-3,4-dihydro-2H-benzo[b][1,4]-oxazin-7-yl)-1H-1,2,3-triazol-5-yl)-carbamate | 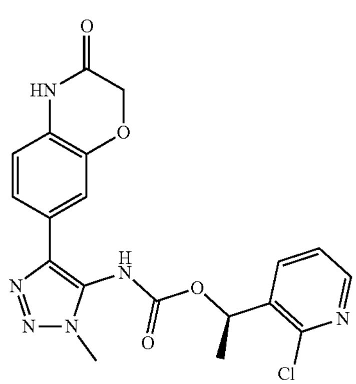 [SMILES: C[C@@H](OC(=O)Nc1c(-c2ccc3c(c2)OCC(=O)N3)nnn1C)c1cccnc1Cl] | | 429.1 | 1H NMR (400 MHz, Methanol-d4) δ 8.35 (s, 1H), 8.05 (s, 1H), 7.48 (s, 1H), 7.37-7.27 (m, 2H), 6.94 (d, J = 8.2 Hz, 1H), 6.10 (s, 1H), 4.62 (s, 2H), 3.92 (s, 3H), 1.65 (s, 3H). |

Example 20: Preparation of (R)-1-(2-chlorophenyl)ethyl (1-methyl-4-(4-methyl-2-oxo-1,2,3,4-tetrahydroquinoxalin-6-yl)-1H-1,2,3-triazol-5-yl)carbamate (Compound 19)

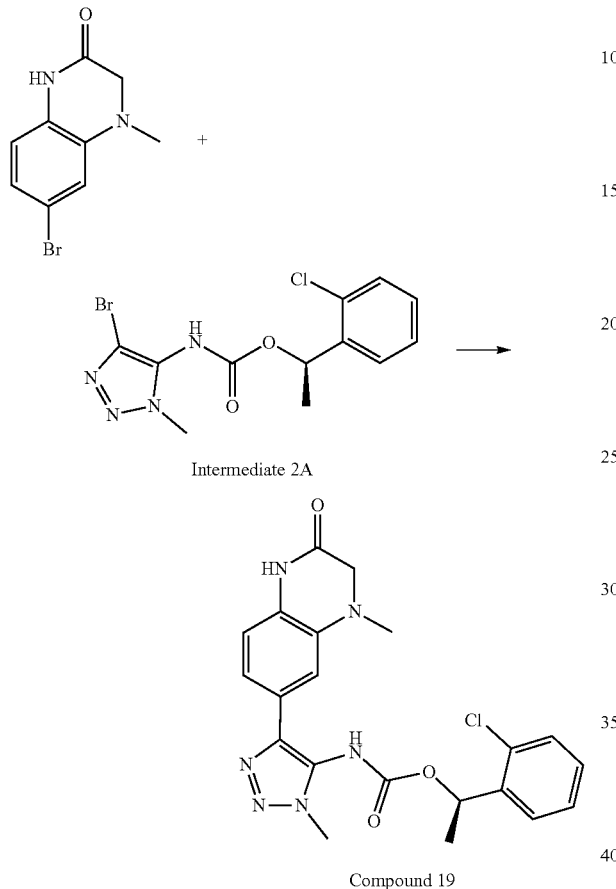

Intermediate 2A

Compound 19

A mixture of 6-bromo-4-methyl-1,3-dihydroquinoxalin-2-one (0.556 mmol), 1,1'-Bis(diphenylphosphino)ferrocene-palladium(II)dichloride, dichloromethane complex (0.0278 mmol), Bis(pinacolato)diboron (0.834 mmol), and potassium acetate (0.834 mmol) in 1,4-dioxane (3 mL) was heated to 100° C. for 1 hour. At this point, the reaction was cooled to room temperature, and (R)-1-(2-chlorophenyl)ethyl (4-bromo-1-methyl-1H-1,2,3-triazol-5-yl)carbamate (Intermediate 2A) (0.278 mmol), potassium carbonate (0.834 mmol), and water (1 mL) were added to the reaction. The reaction was purged with nitrogen and heated to 100° C. for 1 hour. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide (R)-1-(2-chlorophenyl)ethyl (1-methyl-4-(4-methyl-2-oxo-1,2,3,4-tetrahydroquinoxalin-6-yl)-1H-1,2,3-triazol-5-yl)carbamate (Compound 19). (MS (m/z) 441.1 [M+H]$^+$). $^1$H NMR (400 MHz, Methanol-$d_4$) δ 7.61 (s, 1H), 7.48-7.24 (m, 3H), 7.12 (s, 2H), 6.85 (d, J=8.1 Hz, 1H), 6.22 (q, J=6.3, 5.9 Hz, 1H), 3.92 (s, 3H), 3.73 (s, 2H), 2.82 (s, 3H), 1.59 (d, J=6.6 Hz, 3H).

Example 21: Preparation of (R)-1-(2-chloro-5-fluoropyridin-3-yl)ethyl (1-methyl-4-(2-oxo-1,2,3,4-tetrahydroquinolin-6-yl)-1H-1,2,3-triazol-5-yl)carbamate (Compound 20)

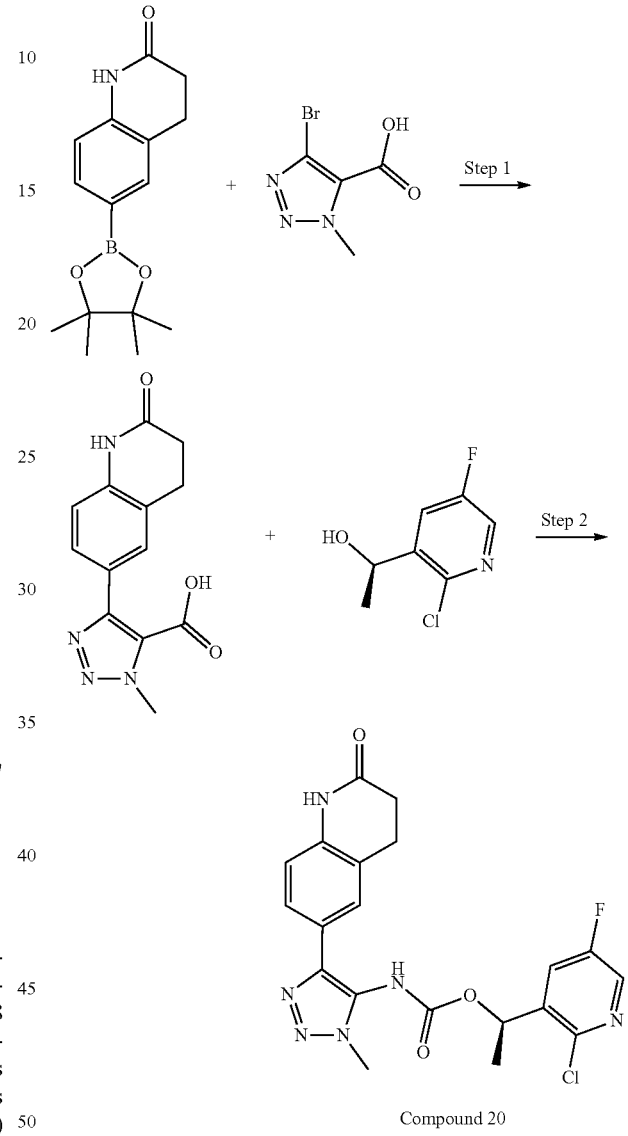

Compound 20

Step 1: 3-methyl-5-(2-oxo-3,4-dihydro-1H-quinolin-6-yl)triazole-4-carboxylic acid A mixture of 6-(4,4,5,5-tetramethyl-1,3,2-dioxaborolan-2-yl)-3,4-dihydro-1H-quinolin-2-one (0.583 mmol), 4-bromo-1-methyl-1H-1,2,3-triazole-5-carboxylic acid (Intermediate 1) (0.485 mmol), and potassium carbonate (1.46 mmol) in 3:1 1,4-dioxane/water (6 mL) was heated to 100° C. for 6 hours. After completion of the reaction, the mixture was cooled and quenched with 1M HCl (5 mL), resulting in precipitate formation. The precipitated solids were filtered to provide 3-methyl-5-(2-oxo-3,4-dihydro-1H-quinolin-6-yl)triazole-4-carboxylic acid.

Step 2: [(1R)-1-(2-chloro-5-fluoro-3-pyridyl)ethyl] N-[3-methyl-5-(2-oxo-3,4-dihydro-1H-quinolin-6-yl)triazol-4-yl]carbamate (Compound 20)

To a mixture of 3-methyl-5-(2-oxo-3,4-dihydro-1H-quinolin-6-yl)triazole-4-carboxylic acid (0.294 mmol), 1-propanephosphonic acid cyclic anhydride (50% in DMF, 0.441 mmol), and azidotrimethysilane (0.441 mmol) acid in THF (1.5 mL) was added triethylamine (0.588 mmol) dropwise. (1R)-1-(2-chloro-5-fluoro-3-pyridyl)ethanol (0.396 mmol) was added and the flask was heated at 70° C. for 1 hour. After completion of the reaction, the mixture was cooled and diluted with water. The mixture was extracted with ethyl acetate (3×10 mL). The combined organic layers were dried over anhydrous sodium sulfate and concentrated under reduced pressure. The residue was purified by reverse-phase HPLC to provide (R)-1-(2-chloro-5-fluoropyridin-3-yl)ethyl (1-methyl-4-(2-oxo-1,2,3,4-tetrahydroquinolin-6-yl)-1H-1,2,3-triazol-5-yl)carbamate (Compound 20) (MS (m/z) 445.1 [M+H]+). $^1$H NMR (400 MHz, DMSO-$d_6$) δ 10.18 (s, 1H), 9.96 (s, 1H), 8.49 (s, 1H), 7.99 (s, 1H), 7.59-7.36 (m, 2H), 6.87 (d, J=8.2 Hz, 1H), 5.91 (s, 1H), 3.84 (s, 3H), 2.87 (t, J=7.6 Hz, 2H), 2.45 (d, J=7.7 Hz, 2H), 1.61 (s, 3H).

Example 22: Preparation of (R)-1-(2-chloropyridin-3-yl)ethyl (4-(3,3-dimethyl-2-oxo-2,3-dihydro-1H-pyrido[2,3-b][1,4]oxazin-6-yl)-1-methyl-1H-1,2,3-triazol-5-yl)carbamate (Compound 21)

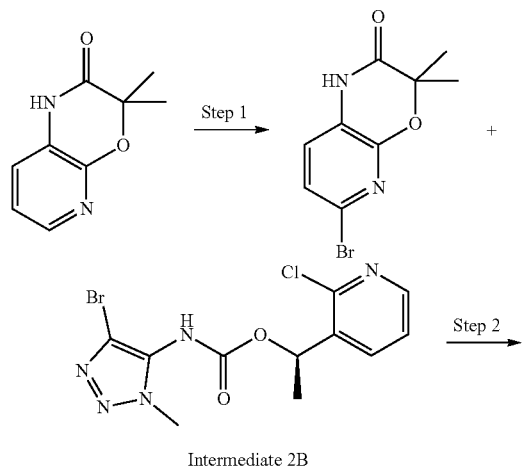

Intermediate 2B

Compound 21

Step 1: 6-bromo-3,3-dimethyl-1H-pyrido[2,3-b][1,4]oxazin-2-one

To a suspension of 3,3-dimethyl-1H-pyrido[2,3-b][1,4]oxazin-2-one (5.61 mmol) in acetonitrile (56 mL) was added N-bromosuccinimide (6.17 mmol) followed by Trifluoroacetic acid (1.12 mmol). The reaction was then heated at 70° C. for 8 hours. After completion of the reaction, the mixture was diluted with water. The mixture was extracted with ethyl acetate (3×50 mL). The combined organic layers were dried over anhydrous sodium sulfate and concentrated under reduced pressure. The residue was purified by column chromatography to yield 6-bromo-3,3-dimethyl-1H-pyrido[2,3-b][1,4]oxazin-2-one.

Step 2: (R)-1-(2-chloropyridin-3-yl)ethyl (4-(3,3-dimethyl-2-oxo-2,3-dihydro-1H-pyrido[2,3-b][1,4]oxazin-6-yl)-1-methyl-1H-1,2,3-triazol-5-yl)carbamate (Compound 21)

To a mixture of of (R)-1-(2-chloropyridin-3-yl)ethyl (4-bromo-1-methyl-1H-1,2,3-triazol-5-yl)carbamate (Intermediate 2B) (0.42 mmol) in THF (4.2 mL) at −78° C. was added a 1 M solution of lithium bis(trimethylsilyl)amide in THF (0.46 mmol). After 10 minutes, a 2.5 M solution of n-butyllithium (0.83 mmol) in Hexanes was added. After 45 minutes, a 1.9 M solution of zinc chloride (1.3 mmol) in 2-MeTHF was added, and the reaction was stirred at room temperature for 45 minutes. At this point 6-bromo-3,3-dimethyl-1H-pyrido[2,3-b][1,4]oxazin-2-one (0.39 mmol) and [1,1'-bis(diphenylphosphino)ferrocene]dichloropalladium(II), dichloromethane complex (0.042 mmol) were added to the reaction and the reaction mixture was heated to 70° C. for 1 hour. After completion of the reaction, the mixture was cooled and quenched with saturated aqueous ammonium chloride. The mixture was diluted with ethyl acetate and organics were separated. The aqueous layer was extracted with ethyl acetate (3×10 mL). The combined organic layers were dried over anhydrous sodium sulfate and concentrated under reduced pressure. The residue was purified by reverse-phase HPLC to provide (R)-1-(2-chloropyridin-3-yl)ethyl (4-(3,3-dimethyl-2-oxo-2,3-dihydro-1H-pyrido[2,3-b][1,4]oxazin-6-yl)-1-methyl-1H-1,2,3-triazol-5-yl)carbamate (Compound 21) (MS (m/z) 458.1 [M+H]+). $^1$H NMR (400 MHz, Methanol-$d_4$) δ 8.38-7.93 (m, 2H), 7.62 (d, J=8.0 Hz, 1H), 7.52-7.35 (m, 1H), 7.35-7.24 (m, 1H), 6.08 (q, J=6.4 Hz, 1H), 3.95 (s, 3H), 1.74-1.43 (m, 9H).

Example 23: Preparation of (R)-1-(2-chloropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate (Compound 22)

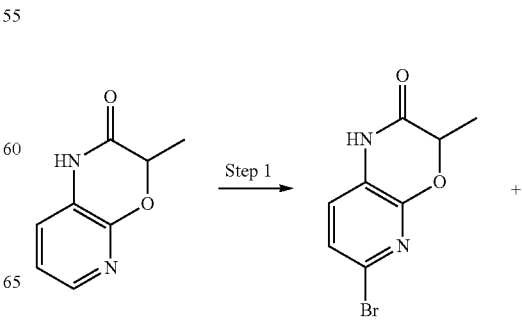

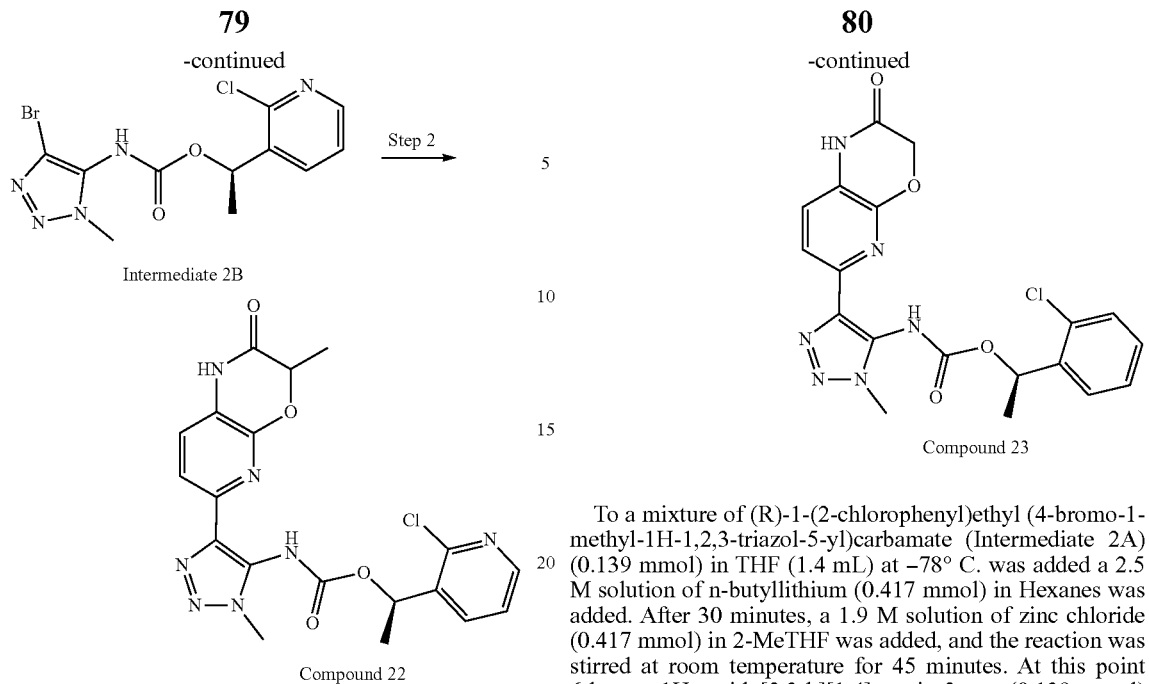

Intermediate 2B

Compound 22

Compound 23

Following the synthesis described in Example 19 for (R)-1-(2-chloropyridin-3-yl)ethyl (4-(3,3-dimethyl-2-oxo-2,3-dihydro-1H-pyrido[2,3-b][1,4]oxazin-6-yl)-1-methyl-1H-1,2,3-triazol-5-yl)carbamate (Compound 21), using 3-methyl-1H-pyrido[2,3-b][1,4]oxazin-2-one (0.609 mmol) instead of 3,3-dimethyl-1H-pyrido[2,3-b][1,4]oxazin-2-one in step 1, (R)-1-(2-chloropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate (Compound 22) was obtained (MS (m/z) 444.1 [M+H]$^+$). $^1$H NMR (400 MHz, Methanol-d$_4$) δ 8.42-7.92 (m, 2H), 7.62 (d, J=8.0 Hz, 1H), 7.42 (s, 1H), 7.31 (s, 1H), 6.08 (q, J=6.6 Hz, 1H), 4.94-4.90 (m, 1H), 4.58 (s, 3H), 3.95 (s, 3H), 1.58 (d, J=6.9 Hz, 3H).

Example 24: Preparation of (R)-1-(2-chlorophenyl)ethyl (1-methyl-4-(2-oxo-2,3-dihydro-1H-pyrido[2,3-b][1,4]oxazin-6-yl)-1H-1,2,3-triazol-5-yl)carbamate (Compound 23)

To a mixture of (R)-1-(2-chlorophenyl)ethyl (4-bromo-1-methyl-1H-1,2,3-triazol-5-yl)carbamate (Intermediate 2A) (0.139 mmol) in THF (1.4 mL) at −78° C. was added a 2.5 M solution of n-butyllithium (0.417 mmol) in Hexanes was added. After 30 minutes, a 1.9 M solution of zinc chloride (0.417 mmol) in 2-MeTHF was added, and the reaction was stirred at room temperature for 45 minutes. At this point 6-bromo-1H-pyrido[2,3-b][1,4]oxazin-2-one (0.139 mmol) and [1,1'-bis(diphenylphosphino)ferrocene]dichloropalladium(II), dichloromethane complex (0.0139 mmol) were added to the reaction and the reaction mixture was heated to 70° C. for 1 hour. After completion of the reaction, the mixture was cooled and quenched with saturated aqueous ammonium chloride. The mixture was diluted with ethyl acetate and organics were separated. The aqueous layer was extracted with ethyl acetate (3×10 mL). The combined organic layers were dried over anhydrous sodium sulfate and concentrated under reduced pressure. The residue was purified by reverse-phase HPLC to provide (R)-1-(2-chlorophenyl)ethyl (1-methyl-4-(2-oxo-2,3-dihydro-1H-pyrido[2,3-b][1,4]oxazin-6-yl)-1H-1,2,3-triazol-5-yl)carbamate (Compound 23) (MS (m/z) 429.0 [M+H]$^+$). $^1$H NMR (400 MHz, Methanol-d$_4$) δ 7.64-7.50 (m, 2H), 7.37 (d, J=7.9 Hz, 1H), 7.34-7.17 (m, 3H), 6.16 (q, J=6.6 Hz, 1H), 4.82 (s, 2H), 3.94 (s, 3H), 1.56 (s, 3H).

Example 25: Preparation of (R)-1-(2-chloropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate (Compound 24)

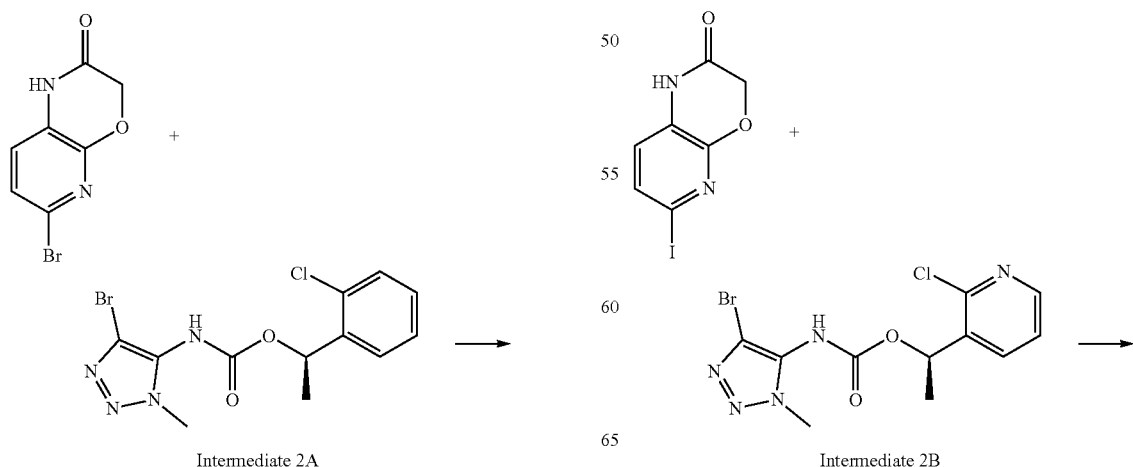

Intermediate 2A

Intermediate 2B

81

-continued

Compound 24

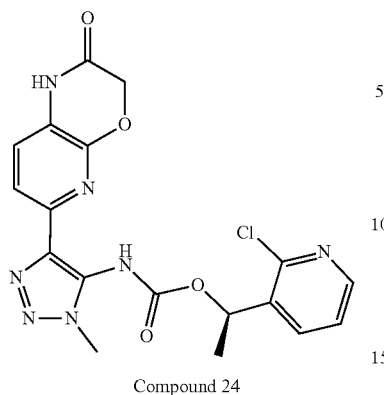

To a mixture of (R)-1-(2-chloropyridin-3-yl)ethyl (4-bromo-1-methyl-1H-1,2,3-triazol-5-yl)carbamate (Intermediate 2B) (2.77 mmol) in THF (28 mL) at −78° C. was added a 1 M solution of lithium bis(trimethylsilyl)amide (3.05 mmol) in THF. After 10 minutes, a 2.5 M solution of n-butyllithium (6.93 mmol) in Hexanes was added. After 45 minutes, a 1.9 M solution of zinc chloride (9.71 mmol) in 2-MeTHF was added, and the reaction was stirred at room temperature for 45 minutes. At this point 6-iodo-1H-pyrido[2,3-b][1,4]oxazin-2-one (2.77 mmol) and [1,1'-bis(diphenylphosphino)ferrocene]dichloropalladium(II), dichloromethane complex (0.277 mmol) were added to the reaction and the reaction mixture was heated to 70° C. for 1 hour. After completion of the reaction, the mixture was cooled and quenched with saturated aqueous ammonium chloride. The mixture was diluted with ethyl acetate and organics were separated. The aqueous layer was extracted with ethyl acetate (3×10 mL). The combined organic layers were dried over anhydrous sodium sulfate and concentrated under reduced pressure. The residue was purified by reverse-phase HPLC to provide (R)-1-(2-chloropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate (Compound 24) (MS (m/z) 430.0 [M+H]$^+$). $^1$H NMR (400 MHz, Methanol-d$_4$) δ 8.30 (s, 1H), 8.12 (s, 1H), 7.60 (d, J=8.4 Hz, 1H), 7.45 (s, 1H), 7.31 (s, 1H), 6.11 (dd, J=22.0, 6.6 Hz, 1H), 4.90 (s, 2H), 3.95 (s, 3H), 1.63 (d, J=6.6 Hz, 3H).

Example 26: Preparation of [((R)-1-(2-chloro-3-pyridyl)ethyl]N-[3-methyl-5-(2-oxo-1,4-dihydropyrido[3,2-d][1,3]oxazin-6-yl)triazol-4-yl]carbamate (Compound 25)

82

-continued

Intermediate 2B

Compound 25

Following the synthesis described in Example 25 for (R)-1-(2-chloropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate, using 6-bromo-1,4-dihydro-2H-pyrido[3,2-d][1,3]oxazin-2-one (0.277 mmol) instead of 6-iodo-1H-pyrido[2,3-b][1,4]oxazin-2(3H)-one, and (2-Dicyclohexylphosphino-2',4',6'-triisopropyl-1,1'-biphenyl)[2-(2'-amino-1,1'-biphenyl)]palladium(II) methanesulfonate (0.0277 mmol) instead of [1,1'-bis(diphenylphosphino)ferrocene]dichloropalladium(II), dichloromethane complex, [(1R)-1-(2-chloro-3-pyridyl)ethyl] N-[3-methyl-5-(2-oxo-1,4-dihydropyrido[3,2-d][1,3]oxazin-6-yl)triazol-4-yl]carbamate (Compound 25) was obtained. (MS (m/z) 430.0 [M+H]$^+$). $^1$H NMR (400 MHz, Methanol-d$_4$) δ 8.31 (d, J=19.5 Hz, 1H), 8.05 (s, 1H), 7.87 (d, J=8.4 Hz, 1H), 7.43 (s, 1H), 7.30 (s, 1H), 6.11 (s, 1H), 5.33 (s, 2H), 3.99 (s, 3H), 1.63 (d, J=17.1 Hz, 3H).

Example 27: Preparation of (R)-1-(2-chloropyridin-3-yl)ethyl (4-(3-ethyl-2-oxo-2,3-dihydro-1H-pyrido[2,3-b][1,4]oxazin-6-yl)-1-methyl-1H-1,2,3-triazol-5-yl)carbamate (Compound 26)

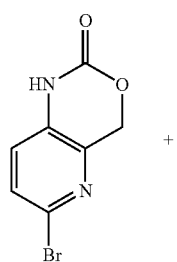

+

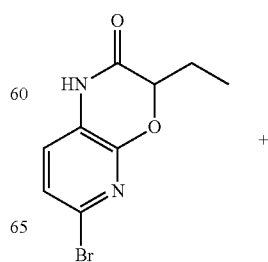

+

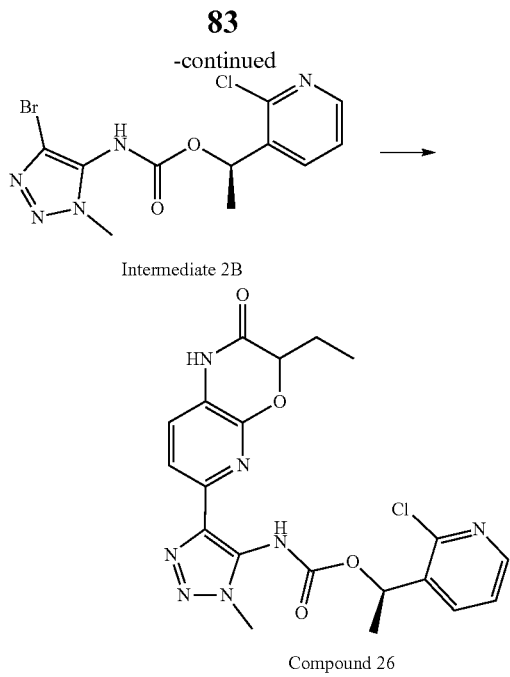

Intermediate 2B

Compound 26

Following the synthesis described in Example 25 for (R)-1-(2-chloropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate, using 6-bromo-3-ethyl-1H-pyrido[2,3-b][1,4]oxazin-2(3H)-one (0.555 mmol) instead of 6-iodo-1H-pyrido[2,3-b][1,4]oxazin-2(3H)-one, (R)-1-(2-chloropyridin-3-yl)ethyl (4-(3-ethyl-2-oxo-2,3-dihydro-1H-pyrido[2,3-b][1,4]oxazin-6-yl)-1-methyl-1H-1,2,3-triazol-5-yl)carbamate (Compound 26) was obtained. (MS (m/z) 458.0 [M+H]⁺). ¹H NMR (400 MHz, Methanol-d₄) δ 8.30 (s, 1H), 8.11 (s, 1H), 7.60 (dd, J=8.0, 3.2 Hz, 1H), 7.41 (s, 1H), 7.29 (d, J=7.8 Hz, 1H), 6.08 (d, J=6.5 Hz, 1H), 4.79-4.71 (m, 1H), 3.96 (s, 3H), 2.09-1.82 (m, 2H), 1.62 (s, 3H), 1.08 (q, J=7.1 Hz, 3H).

Example 28: Preparation of (R)-1-(2-chloropyridin-3-yl)ethyl (1-methyl-4-(2-oxo-3-phenyl-2,3-dihydro-1H-pyrido[2,3-b][1,4]oxazin-6-yl)-1H-1,2,3-triazol-5-yl)carbamate (Compound 27)

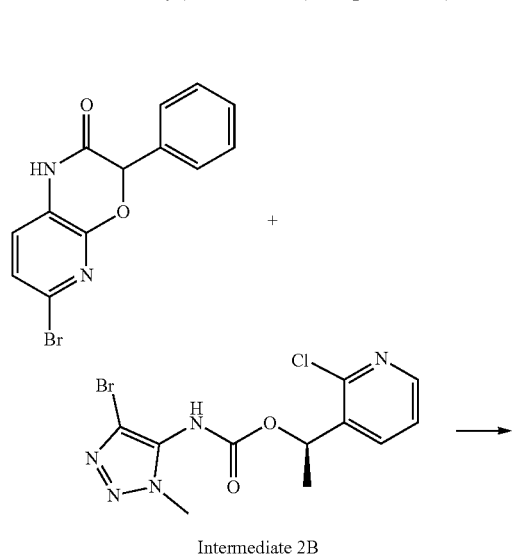

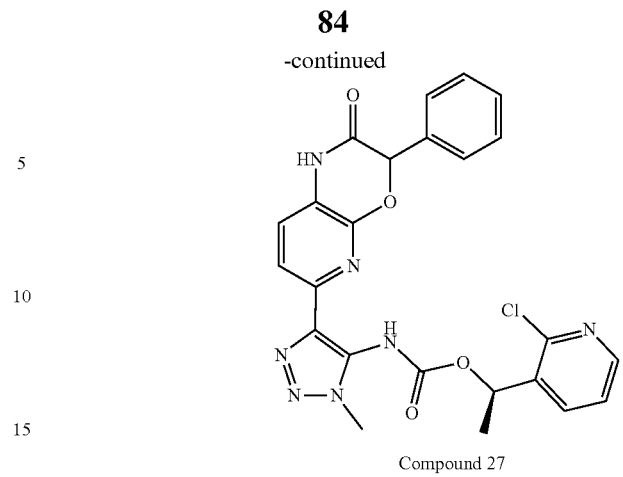

Compound 27

Following the synthesis described in Example 25 for (R)-1-(2-chloropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate, using 6-bromo-3-phenyl-1H-pyrido[2,3-b][1,4]oxazin-2(3H)-one (0.555 mmol) instead of 6-iodo-1H-pyrido[2,3-b][1,4]oxazin-2(3H)-one, (R)-1-(2-chloropyridin-3-yl)ethyl (1-methyl-4-(2-oxo-3-phenyl-2,3-dihydro-1H-pyrido[2,3-b][1,4]oxazin-6-yl)-1H-1,2,3-triazol-5-yl)carbamate (Compound 27) was obtained. (MS (m/z) 506.0 [M+H]⁺). ¹H NMR (400 MHz, DMSO-d₆) δ 11.19 (d, J=4.6 Hz, 1H), 9.82 (s, 1H), 8.30 (d, J=26.8 Hz, 1H), 7.96 (s, 1H), 7.64 (t, J=7.5 Hz, 1H), 7.48-7.31 (m, 6H), 7.27 (s, 1H), 6.01 (d, J=13.3 Hz, 1H), 5.86 (s, 1H), 3.86 (s, 3H), 1.35 (d, J=83.8 Hz, 3H).

Example 29: Preparation of (R)-1-(2-chloropyridin-3-yl)ethyl (4-(7-fluoro-2-oxo-2,3-dihydro-1H-pyrido[2,3-b][1,4]oxazin-6-yl)-1-methyl-1H-1,2,3-triazol-5-yl)carbamate (Compound 28)

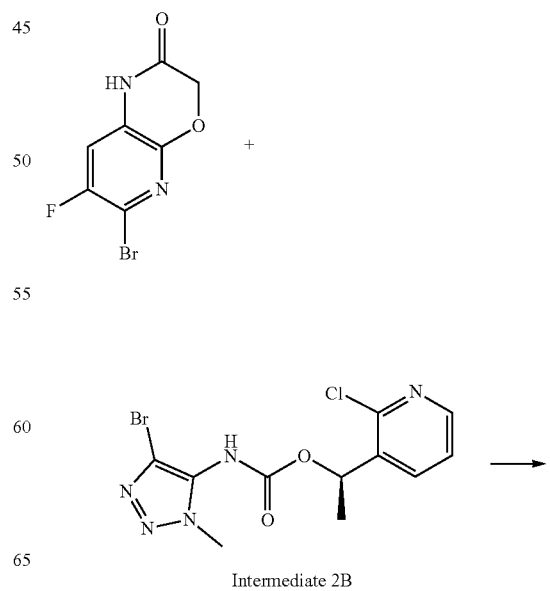

Intermediate 2B

85

-continued

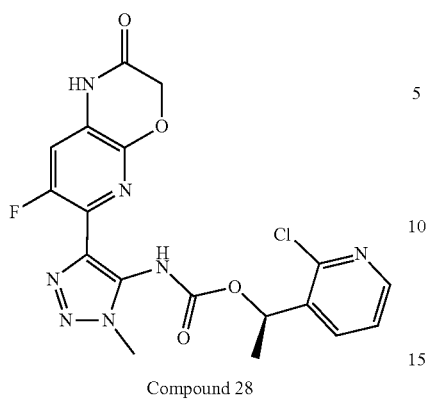

Compound 28

Following the synthesis described in Example 25 for (R)-1-(2-chloropyridin-3-yl)ethyl (1-methyl-4-(2-oxo-2,3-dihydro-1H-pyrido[2,3-b][1,4]oxazin-6-yl)-1H-1,2,3-triazol-5-yl)carbamate, using 6-bromo-7-fluoro-1H-pyrido[2,3-b][1,4]oxazin-2(3H)-one (0.555 mmol) instead of 6-iodo-1H-pyrido[2,3-b][1,4]oxazin-2(3H)-one, and (2-Dicyclohexylphosphino-2',4',6'-triisopropyl-1,1'-biphenyl)[2-(2'-amino-1,1'-biphenyl)]palladium(II) methanesulfonate (0.0555 mmol) instead of [1,1'-bis(diphenylphosphino)ferrocene]dichloropalladium(II), dichloromethane complex, (R)-1-(2-chloropyridin-3-yl)ethyl (4-(7-fluoro-2-oxo-2,3-dihydro-1H-pyrido[2,3-b][1,4]oxazin-6-yl)-1-methyl-1H-1,2,3-triazol-5-yl)carbamate (Compound 28) was obtained. (MS (m/z) 448.0 [M+H]+). ¹H NMR (400 MHz, Methanol-d₄) δ 8.32 (s, 1H), 8.06 (s, 1H), 7.45 (d, J=5.7 Hz, 1H), 7.12 (s, 1H), 6.09-6.00 (m, 1H), 4.82 (s, 2H), 3.97 (s, 3H), 1.63 (d, J=6.8 Hz, 3H).

Example 30: Preparation of (R)-1-(2-chloropyridin-3-yl)ethyl (4-(8-fluoro-2-oxo-1,2,3,4-tetrahydroquinolin-6-yl)-1-methyl-1H-1,2,3-triazol-5-yl)carbamate (Compound 29)

86

-continued

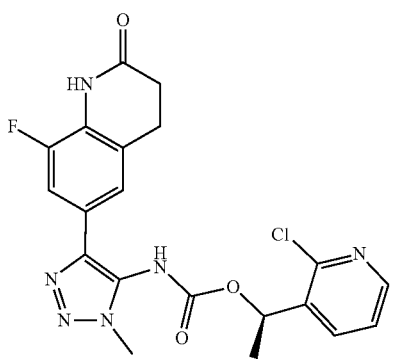

Compound 29

Following the synthesis described in Example 14 for [(1R)-1-(2-chloro-3-pyridyl)ethyl] N-[5-(7-fluoro-2-oxo-3,4-dihydro-1H-quinolin-6-yl)-3-methyl-triazol-4-yl]carbamate in step 1, 6-bromo-8-fluoro-3,4-dihydroquinolin-2(1H)-one (0.82 mmol) instead of 6-bromo-7-fluoro-3,4-dihydro-1H-quinolin-2-one, (R)-1-(2-chloropyridin-3-yl)ethyl (4-(8-fluoro-2-oxo-1,2,3,4-tetrahydroquinolin-6-yl)-1-methyl-1H-1,2,3-triazol-5-yl)carbamate (Compound 29) was obtained. (MS (m/z) 445.2 [M+H]+). ¹H NMR (400 MHz, Methanol-d₄) δ 8.34 (s, 1H), 8.05 (s, 1H), 7.48 (s, 1H), 7.38 (d, J=5.5 Hz, 1H), 7.35 (d, J=1.7 Hz, 1H), 6.11 (s, 1H), 3.93 (s, 3H), 3.02 (t, J=7.6 Hz, 2H), 2.69-2.51 (m, 2H), 1.75-1.22 (m, 3H).

Example 31: Preparation of (R)-1-(2-chloro-5-fluoropyridin-3-yl)ethyl (1-methyl-4-(2-oxo-3-(trifluoromethyl)-2,3-dihydro-1H-pyrido[2,3-b][1,4]oxazin-6-yl)-1H-1,2,3-triazol-5-yl)carbamate (Compound 30)

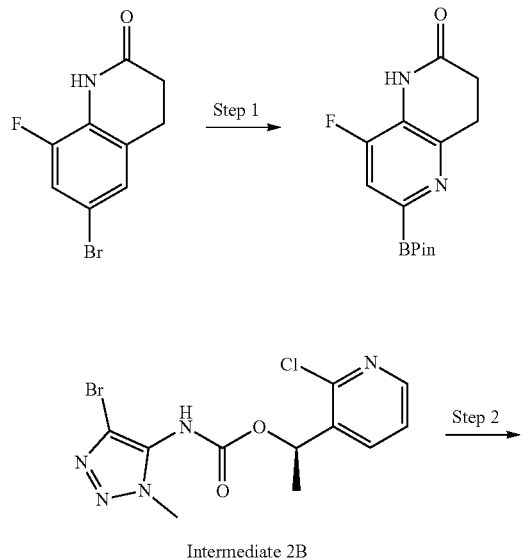

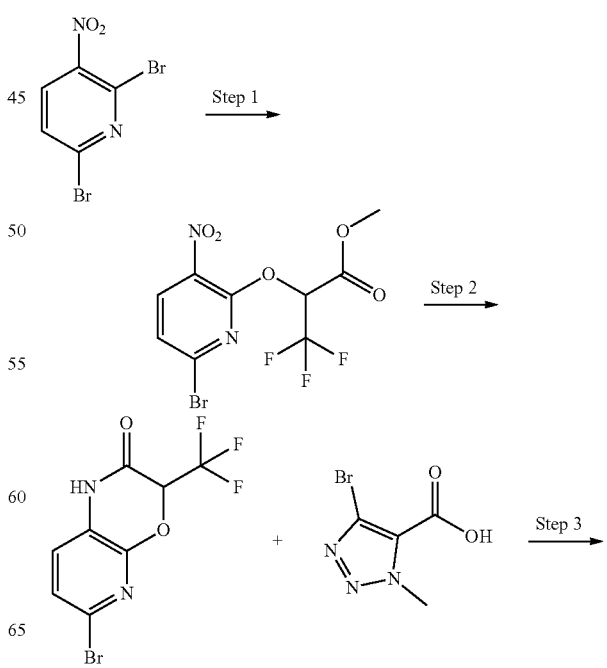

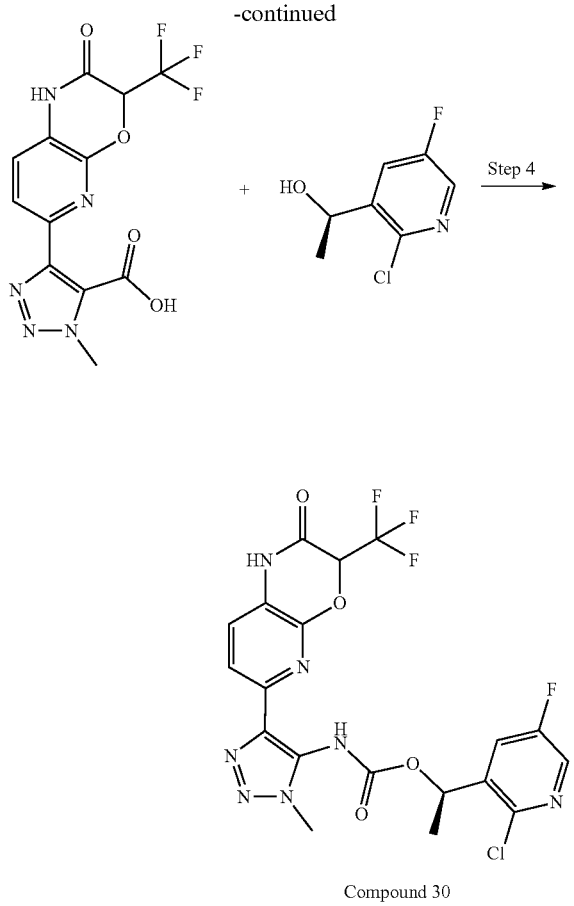

Compound 30

Step 1: Methyl 2-[(6-bromo-3-nitro-2-pyridyl)oxy]-3,3,3-trifluoro-propanoate To a suspension of 2,6-dibromo-3-nitro-pyridine (3.55 mmol) and methyl 3,3,3-trifluoro-2-hydroxy-propanoate (3.90 mmol) in THF (6 mL) was added sodium hydride (4.26 mmol) at 0° C. The reaction was stirred at room temperature. After completion of the reaction, the mixture was diluted with water. The reaction mixture was extracted with ethyl acetate (3×10 mL). The combined organic layers were dried over anhydrous sodium sulfate and concentrated under reduced pressure to provide methyl 2-[(6-bromo-3-nitro-2-pyridyl)oxy]-3,3,3-trifluoro-propanoate. This material was carried on without further purification.

Step 2: 6-bromo-3-(trifluoromethyl)-1H-pyrido[2,3-b][1,4]oxazin-2-one

To a suspension of methyl 2-[(6-bromo-3-nitro-2-pyridyl)oxy]-3,3,3-trifluoro-propanoate (3.55 mmol) in acetic acid (10 mL) was added iron powder (24.8 mmol) and heated to 80° C. for 30 minutes. After completion of the reaction, the reaction mixture was cooled to room temperature and filtered through celite. The filter cake was washed with ethyl acetate, and the combined filtrate was concentrated. The residue was purified by column chromatography to provide 6-bromo-3-(trifluoromethyl)-1H-pyrido[2,3-b][1,4]oxazin-2-one.

Step 3: 1-methyl-4-(2-oxo-3-(trifluoromethyl)-2,3-dihydro-1H-pyrido[2,3-b][1,4]oxazin-6-yl)-1H-1,2,3-triazole-5-carboxylic acid 4-bromo-1-methyl-1H-1,2,3-triazole-5-carboxylic acid, Intermediate 1 (2.43 mmol) was dissolved in 24 mL of tetrahydrofuran and submerged in a −78° C. bath for 15 minutes. A 1 M solution of Lithium bis(trimethylsilyl)amide in tetrahydrofuran (2.67 mmol) was dropwise over 15 minutes. A 2.5 M solution of n-butyllithium (4.85 mmol) in hexanes was added dropwise over 20 minutes and allowed to stir for an additional 1 hour. A 1.9 M solution of zinc chloride (7.52 mmol) in 2-methyl tetrahydrofuran was added dropwise over 15 minutes. The reaction mixture was warmed to ambient temperature by submerging in a water bath and allowed to stir for 30 minutes. The resulting mixture was sparged with argon gas for 10 minutes, and then 6-bromo-3-(trifluoromethyl)-1H-pyrido[2,3-b][1,4]oxazin-2-one (1.70 mmol) and [1,1'-Bis(diphenylphosphino)ferrocene]dichloropalladium(II), complex with dichloromethane (0.24 mmol) were added. The reaction was heated at 70° C. for 1 hour, and then cooled to ambient temperature. The reaction was diluted with 20 mL of a 2 M aqueous solution of sodium hydroxide and 20 mL of diethyl ether. The aqueous layer was separated, and the organic layer was extracted with a 2M aqueous solution of sodium hydroxide (20 mL). The combined aqueous layer was washed with a 1:1 mixture of ethyl acetate and diethyl ether (20 mL×2). 5 mL of concentrated hydrochloric acid was dropwise over 15 minutes under vigorous stirring to adjust pH to 4. The mixture was filtered, and the filter cake was washed with water (10 mL) and a 1:1 mixture of ethyl acetate and diethyl ether (10 mL×2). The precipitate was dried under reduced pressure to provide 1-methyl-4-(2-oxo-3-(trifluoromethyl)-2,3-dihydro-1H-pyrido[2,3-b][1,4]oxazin-6-yl)-1H-1,2,3-triazole-5-carboxylic acid.

Step 4: (R)-1-(2-chloro-5-fluoropyridin-3-yl)ethyl (1-methyl-4-(2-oxo-3-(trifluoromethyl)-2,3-dihydro-1H-pyrido[2,3-b][1,4]oxazin-6-yl)-1H-1,2,3-triazol-5-yl)carbamate To a mixture of 1-methyl-4-(2-oxo-3-(trifluoromethyl)-2,3-dihydro-1H-pyrido[2,3-b][1,4]oxazin-6-yl)-1H-1,2,3-triazole-5-carboxylic acid (0.208 mmol), 1-propanephosphonic acid cyclic anhydride (50% in DMF, 0.312 mmol), and azidotrimethysilane (0.312 mmol) acid in THF (1.05 mL) was added triethylamine (0.417 mmol) dropwise. (1R)-1-(2-chloro-5-fluoro-3-pyridyl)ethanol (0.309 mmol) was added and the reaction was heated at 70° C. for 1 hour. After completion of the reaction, the mixture was cooled and concentrated under reduced pressure. The residue was purified by reverse-phase HPLC to provide (R)-1-(2-chloro-5-fluoropyridin-3-yl)ethyl (1-methyl-4-(2-oxo-3-(trifluoromethyl)-2,3-dihydro-1H-pyrido[2,3-b][1,4]oxazin-6-yl)-1H-1,2,3-triazol-5-yl)carbamate (Compound 30). (MS (m/z) 516.0 [M+H]$^+$). 1H NMR (400 MHz, Methanol-$d_4$) δ 8.27 (s, 1H), 7.92 (s, 1H), 7.73 (dd, J=8.0, 3.1 Hz, 1H), 7.39 (d, J=8.0 Hz, 1H), 6.05 (d, J=6.9 Hz, 1H), 5.64-5.44 (m, 1H), 3.99 (s, 3H), 1.64 (s, 3H).

Example 32: Preparation of (R)-1-(2-chloro-5-fluoropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate (Compound 31)

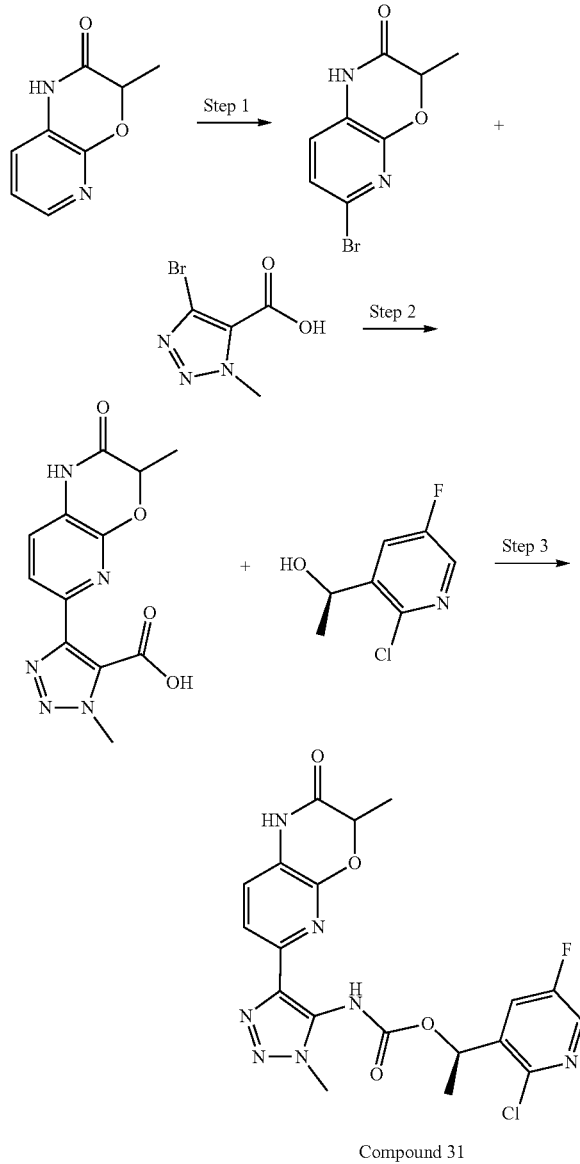

Compound 31

Step 1: 6-bromo-3-methyl-1H-pyrido[2,3-b][1,4]oxazin-2(3H)-one

To a suspension of 3-methyl-1H-pyrido[2,3-b][1,4]oxazin-2(3H)-one (6.09 mmol) in acetonitrile (60 mL) was added N-bromosuccinimide (6.70 mmol) followed by Trifluoroacetic acid (1.22 mmol). The reaction was then heated at 70° C. for 8 hours. After completion of the reaction, the mixture was diluted with water. The mixture was extracted with ethyl acetate (3×50 mL). The combined organic layers were dried over anhydrous sodium sulfate and concentrated under reduced pressure. The residue was purified by column chromatography to yield 6-bromo-3-methyl-1H-pyrido[2,3-b][1,4]oxazin-2(3H)-one.

Step 2: 1-methyl-4-(3-methyl-2-oxo-2,3-dihydro-1H-pyrido[2,3-b][1,4]oxazin-6-yl)-1H-1,2,3-triazole-5-carboxylic acid 4-bromo-1-methyl-1H-1,2,3-triazole-5-carboxylic acid, Intermediate 1 (2.43 mmol) was dissolved in 24 mL of tetrahydrofuran and submerged in a −78° C. bath for 15 minutes. A 1 M solution of Lithium bis(trimethylsilyl)amide in tetrahydrofuran (2.67 mmol) was dropwise over 15 minutes. A 2.5 M solution of n-butyllithium (4.85 mmol) in hexanes was added dropwise over 20 minutes and allowed to stir for an additional 1 hour. A 1.9 M solution of zinc chloride (7.52 mmol) in 2-methyl tetrahydrofuran was added dropwise over 15 minutes. The reaction mixture was warmed to ambient temperature by submerging in a water bath and allowed to stir for 30 minutes. The resulting mixture was sparged with argon gas for 10 minutes, and 6-bromo-3-methyl-1H-pyrido[2,3-b][1,4]oxazin-2(3H)-one (1.70 mmol) and [1,1'-Bis(diphenylphosphino)ferrocene]dichloropalladium(II), complex with dichloromethane (0.24 mmol) were added. The reaction was heated at 70° C. for 1 hour, and then cooled to ambient temperature. The reaction was diluted with 20 mL of a 2 M aqueous solution of sodium hydroxide and 20 mL of diethyl ether. The aqueous layer was separated, and the organic layer was extracted with a 2M aqueous solution of sodium hydroxide (20 mL). The combined aqueous layer was washed with a 1:1 mixture of ethyl acetate and diethyl ether (20 mL×2). 5 mL of concentrated hydrochloric acid was dropwise over 15 minutes under vigorous stirring to adjust pH to 4. The mixture was filtered, and the filter cake was washed with water (10 mL) and a 1:1 mixture of ethyl acetate and diethyl ether (10 mL×2). The precipitate was dried under reduced pressure to provide 1-methyl-4-(3-methyl-2-oxo-2,3-dihydro-1H-pyrido[2,3-b][1,4]oxazin-6-yl)-1H-1,2,3-triazole-5-carboxylic acid.

Step 3: (R)-1-(2-chloro-5-fluoropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate To a mixture of 1-methyl-4-(3-methyl-2-oxo-2,3-dihydro-1H-pyrido[2,3-b][1,4]oxazin-6-yl)-1H-1,2,3-triazole-5-carboxylic acid (0.211 mmol), 1-propanephosphonic acid cyclic anhydride (50% in DMF, 0.312 mmol), and azidotrimethylsilane (0.316 mmol) acid in THF (1.05 mL) was added triethylamine (0.422 mmol) dropwise. (1R)-1-(2-chloro-5-fluoro-3-pyridyl)ethanol (0.313 mmol) was added and the reaction was heated at 70° C. for 1 hour. After completion of the reaction, the mixture was cooled and concentrated under reduced pressure. The residue was purified by reverse-phase HPLC to provide (R)-1-(2-chloro-5-fluoropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate (Compound 31). (MS (m/z) 462.0 [M+H]$^+$). $^1$H NMR (400 MHz, Methanol-d$_4$) δ 8.24 (s, 1H), 7.90 (s, 1H), 7.63 (d, J=8.0 Hz, 1H), 7.30 (s, 1H), 6.04 (q, J=6.6 Hz, 1H), 4.95-4.87 (m, 1H), 3.97 (s, 3H), 1.61 (s, 3H), 1.56 (d, J=6.9 Hz, 3H).

Example 33: Preparation of (R)-1-(2,5-difluoropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate (Compound 32)

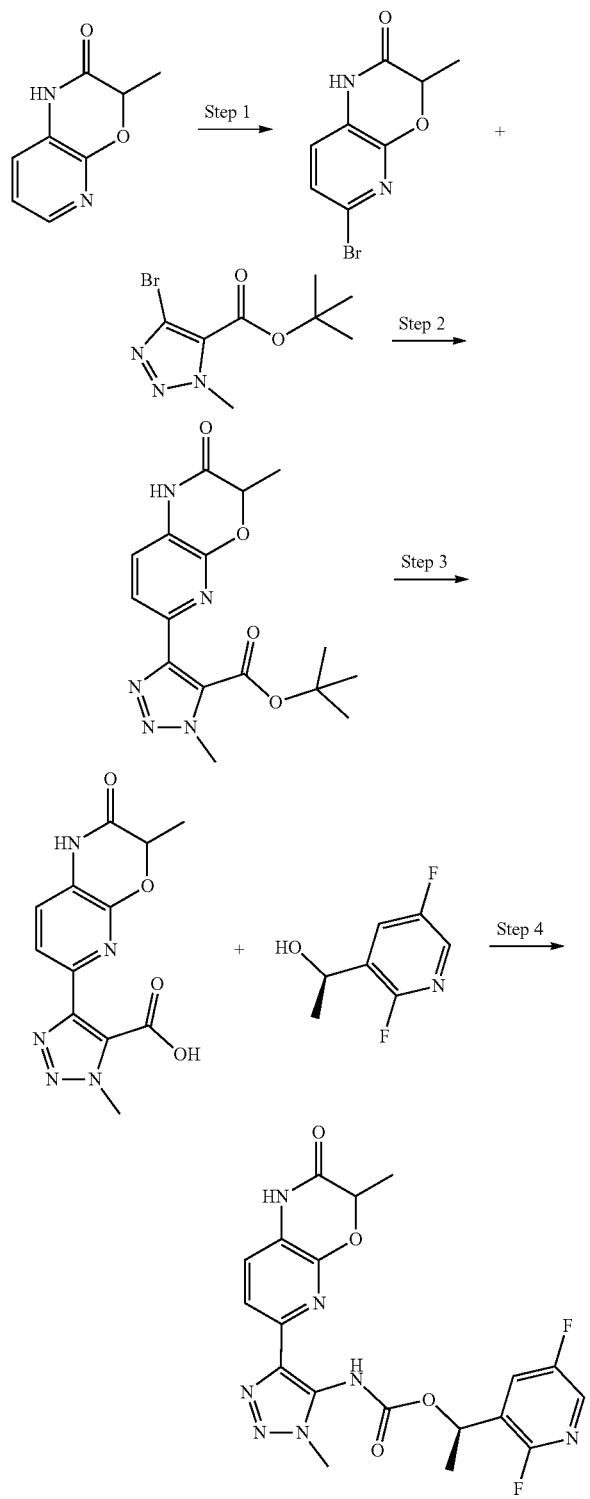

Compound 32

Step 1: 6-bromo-3-methyl-1H-pyrido[2,3-b][1,4]oxazin-2(3H)-one

To a suspension of 3-methyl-1H-pyrido[2,3-b][1,4]oxazin-2(3H)-one (6.09 mmol) in acetonitrile (60 mL) was added N-bromosuccinimide (6.70 mmol) followed by Trifluoroacetic acid (1.22 mmol). The reaction was then heated at 70° C. for 8 hours. After completion of the reaction, the mixture was diluted with water. The mixture was extracted with ethyl acetate (3×50 mL). The combined organic layers were dried over anhydrous sodium sulfate and concentrated under reduced pressure. The residue was purified by column chromatography to yield 6-bromo-3-methyl-1H-pyrido[2,3-b][1,4]oxazin-2(3H)-one.

Step 2: tert-butyl 1-methyl-4-(3-methyl-2-oxo-2,3-dihydro-1H-pyrido[2,3-b][1,4]oxazin-6-yl)-1H-1,2,3-triazole-5-carboxylate Tert-butyl 4-bromo-1-methyl-1H-1,2,3-triazole-5-carboxylate (1.53 mmol) was dissolved in 5.5 mL of tetrahydrofuran and submerged in a −78° C. bath for 15 minutes. A 1 M solution of Lithium bis(trimethylsilyl)amide in tetrahydrofuran (1.68 mmol) was dropwise over 15 minutes. A 2.5 M solution of n-butyllithium (3.05 mmol) in hexanes was added dropwise over 20 minutes and allowed to stir for an additional 1 hour. A 1.9 M solution of zinc chloride (4.73 mmol) in 2-methyl tetrahydrofuran was added dropwise over 15 minutes. The reaction mixture was warmed to ambient temperature by submerging in a water bath and allowed to stir for 30 minutes. The resulting mixture was sparged with argon gas for 10 minutes, and 6-bromo-3-methyl-1H-pyrido[2,3-b][1,4]oxazin-2(3H)-one (1.53 mmol) and [1,1'-Bis(diphenylphosphino)ferrocene]dichloropalladium(II), complex with dichloromethane (0.15 mmol) were added. The reaction was heated at 70° C. for 1 hour. After completion of the reaction, the mixture was cooled to room temperature and quenched with ammonium chloride. The mixture was extracted with ethyl acetate (3×20 mL). The combined organic layers were dried over anhydrous sodium sulfate and concentrated under reduced pressure. The residue was purified by column chromatography to yield tert-butyl 1-methyl-4-(3-methyl-2-oxo-2,3-dihydro-1H-pyrido[2,3-b][1,4]oxazin-6-yl)-1H-1,2,3-triazole-5-carboxylate.

Step 3: 1-methyl-4-(3-methyl-2-oxo-2,3-dihydro-1H-pyrido[2,3-b][1,4]oxazin-6-yl)-1H-1,2,3-triazole-5-carboxylic acid To a solution of tert-butyl 1-methyl-4-(3-methyl-2-oxo-2,3-dihydro-1H-pyrido[2,3-b][1,4]oxazin-6-yl)-1H-1,2,3-triazole-5-carboxylate (0.20 mmol) was added trifluoroacetic acid (0.98 mmol). Reaction was complete after 3 hours and concentrated under reduced pressure to yield 1-methyl-4-(3-methyl-2-oxo-2,3-dihydro-1H-pyrido[2,3-b][1,4]oxazin-6-yl)-1H-1,2,3-triazole-5-carboxylic acid. The material was carried forward without further purification.

Step 4: (R)-1-(2,5-difluoropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate To a mixture of 1-methyl-4-(3-methyl-2-oxo-2,3-dihydro-1H-pyrido[2,3-b][1,4]oxazin-6-yl)-1H-1,2,3-triazole-5-carboxylic acid (0.211 mmol), 1-propanephosphonic acid cyclic anhydride (50% in DMF, 0.313 mmol), and azidotrimethysilane (0.316 mmol) acid in THF (1.05 mL) was added triethylamine (0.422 mmol) dropwise. (1R)-1-(2,5-difluoro-3-pyridyl)ethanol (0.313 mmol) was added and the reaction was heated at 70° C. for 1 hour. After completion of the reaction, the mixture was cooled and concentrated under reduced pressure. The residue was purified by reverse-phase HPLC to provide (R)-1-(2,5-difluoropyridin-3-yl)ethyl (1-methyl-4-(3-methyl-2-oxo-2,3-dihydro-1H-pyrido[2,3-b][1,4]oxazin-6-yl)-1H-1,2,3-triazol-5-yl)carbamate (Compound 32). (MS (m/z) 446.0 [M+H]$^+$). $^1$H NMR (400 MHz, Methanol-d$_4$) δ 7.96 (d, J=44.1 Hz, 2H), 7.62 (d, J=8.0 Hz, 1H), 7.31 (d, J=8.0 Hz, 1H), 6.05-5.86 (m, 1H), 4.94-4.89 (m, 1H), 3.96 (s, 3H), 1.73-1.42 (m, 6H).

Example 34: Calcium Assay

In vitro LPAR1 activity was measured in an intracellular calcium mobilization assay.

CHO-K1 EDG2 cells (DiscoverX cat #93-0644C2) expressing human LPAR1 (NM_001401.3) were seeded in a total volume of 25 µL of Dulbecco's Modification of Eagle's Medium (DMEM) with 10% Fetal Bovine Serum, 1× PenStrepGlutamine, 300 ug/ml Hygromycin, and 800 ug/ml G418 into 384-well tissue culture plate (Grenier #781091) at 15,000 cells/well and incubated at 37° C. overnight. Prior to testing, 25 µL Calcium Loading Dye Component A (FLIPR Calcium 6 Assay Kit Molecular Device #R8190) and 2.5 mM Probenecid (Invitrogen #P36400, prepared fresh) in Hank's Balanced Salt Solution (Corning #21-023-CV), 20 mM HEPES (Corning #25-060-CI), 0.1% Bovine Serum Albumin (Sigma-Aldrich #A7906-500G) was add to the cells for 60 minutes at 37° C.

Agonist dose curves of LPA 18:2 (Avanti Polar Lipids cat #857138, 0.5 nM to 10 µM) were recorded to determine the LPA 18:2 EC$_{80}$ for subsequent antagonist assays. For agonist dose curves, cells were removed from the incubator 2 hours after dye loading and transferred to the FLIPR Tetra instrument (Molecular Devices, San Jose, CA). Calcium mobilization was monitored for 5 min and 10 µL 6× LPA in HBSS/20 mM Hepes/0.1% bovine serum albumin (BSA) was added to the cells 5 seconds into the assay.

To determine the LPAR1 antagonist activity of test compounds, cells were pre-incubated with test compound at a dose range of 0.5 nM to 10 µM, followed by LPA at EC$_{80}$ concentration (100 nM). After dye loading, cells were removed from the incubator and 0.3 µL of 200× antagonist was added. Cells were incubated for 60 minutes at 37° C. Antagonist activity was measured on a FLIPR Tetra. Calcium mobilization was monitored for 3.5 minutes and 10 µL 6× EC$_{80}$ LPA in HBSS, 20 mM HEPES, and 0.1% BSA was added to the cells 5 seconds into the assay. Signal amplitude (Maximum minus minimum) values were plotted against log$_{10}$ of antagonist concentration using Dose Response Tool (Gilead Sciences Inc.) to determine EC$_{50}$.

To assess the antagonistic potential of exemplified compounds EC$_{50}$ values were determined for Compounds 1 to 32 in the LPAR1 calcium mobilization assay. Results are shown in Table 3 (LPAR1 EC$_{50}$). The compound numbers correspond to the compound numbers in Examples 1 to 33.

TABLE 3

| Compound | LPAR1 (EC$_{50}$; [nM]) |
|---|---|
| Compound 1 | 85 |
| Compound 2 | 1,984 |
| Compound 3 | 66 |
| Compound 4 | 118 |
| Compound 5 | 100 |
| Compound 6 | 115 |
| Compound 7 | 1,234 |
| Compound 8 | 765 |
| Compound 9 | 4,606 |
| Compound 10 | N/A |
| Compound 11 | 46 |
| Compound 12 | 218 |
| Compound 13 | 38 |
| Compound 14 | 4,157 |
| Compound 15 | 565 |
| Compound 16 | 525 |
| Compound 17 | 390 |
| Compound 18 | 265 |
| Compound 19 | 265 |
| Compound 20 | 118 |
| Compound 21 | 2,280 |
| Compound 22 | 86 |
| Compound 23 | N/A |
| Compound 24 | 123 |
| Compound 25 | 140 |
| Compound 26 | 3,783 |
| Compound 27 | 135 |
| Compound 28 | 660 |
| Compound 29 | 5 |
| Compound 30 | <5 |
| Compound 31 | <5 |
| Compound 32 | 3,783 |

Unless otherwise defined, all technical and scientific terms used herein have the same meaning as commonly understood by one of ordinary skill in the art to which this disclosure belongs.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:
1. A compound selected from the group consisting of:
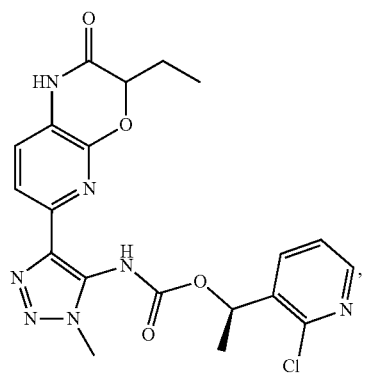
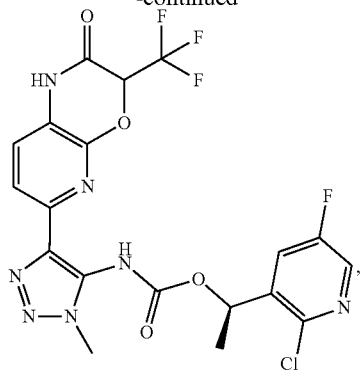

-continued

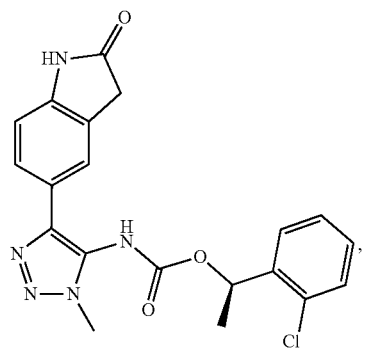

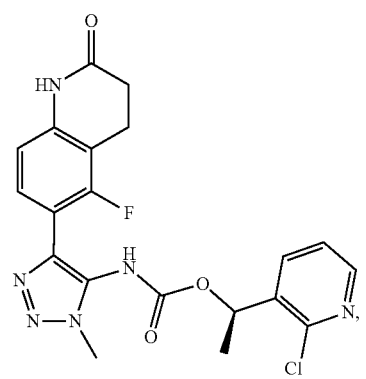

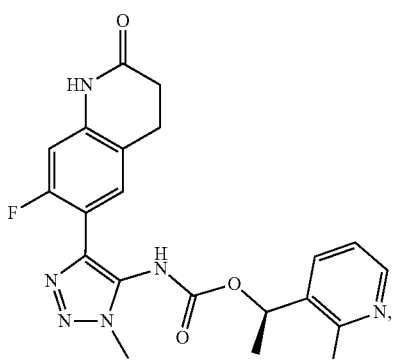

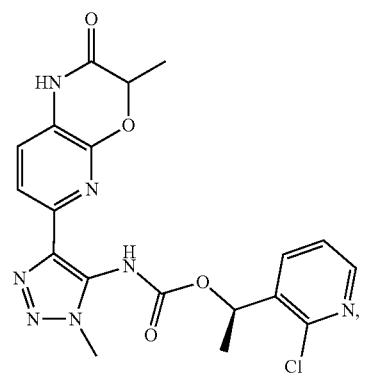

-continued

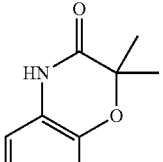

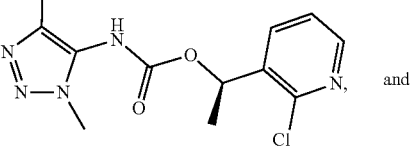 and

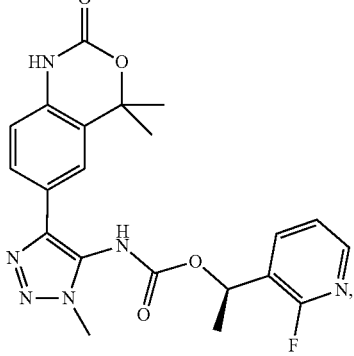

or a pharmaceutically acceptable salt thereof.

2. A The compound or pharmaceutically acceptable salt thereof of claim 1, wherein the compound is

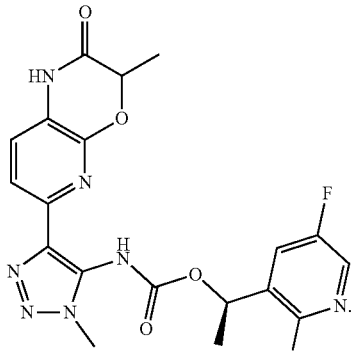

3. A pharmaceutical composition comprising a therapeutically effective amount of a compound, or pharmaceutically acceptable salt thereof, of claim 1, and a pharmaceutically acceptable excipient.

4. A method of treating, stabilizing, or lessening the severity or progression of an LPAR1 mediated disease or condition comprising administering to a patient in need thereof a therapeutically effective amount of a compound of claim 1, or a pharmaceutically acceptable salt thereof, or a pharmaceutical composition of claim 3.

* * * * *